(12) United States Patent
Nicolaou

(10) Patent No.: US 6,384,211 B1
(45) Date of Patent: May 7, 2002

(54) CARBOPEPTOIDS AND CARBO-NUCLEOTOIDS

(75) Inventor: Kyriacos C. Nicolaou, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/417,877

(22) Filed: Oct. 13, 1999

Related U.S. Application Data

(62) Division of application No. 08/913,035, filed on Nov. 20, 1997, now Pat. No. 6,204,376.

(51) Int. Cl.$^7$ .............................. C07H 5/06; C07H 17/00
(52) U.S. Cl. ................... 536/29.1; 536/18.5; 536/117; 536/123; 536/123.1
(58) Field of Search .............................. 536/29.1, 18.5, 536/117, 123, 123.1

(56) References Cited

U.S. PATENT DOCUMENTS

| | | | |
|---|---|---|---|
| 5,212,298 A | | 5/1993 | Rademacher et al. |
| 5,625,030 A | * | 4/1997 | Williams et al. ............ 528/361 |
| 5,637,683 A | * | 6/1997 | Usher et al. ................ 536/22.1 |
| 5,705,621 A | * | 1/1998 | Ravikumar ................. 536/23.1 |
| 5,756,712 A | * | 5/1998 | Sabesan ........................ 536/53 |

OTHER PUBLICATIONS

Yoshimura et al., Nippon Kagaku Kaishi, vol. 11:1958–1963, (1975).*
Yoshimura et al., Bull. Chem. Soc. Japan, vol. 49(9): 2511–2514, (1976).*
Müller et al., J. Chem. Soc., Chem. Commun., vol. 23:2425–2426, (1995).*
Franzkowiak et al., Carbohydrate Res., vol. 158: 13–35, (1986).*
Fuchs et al. (Carbohydrate Res., vol. 49, pp. 267–273, (Jul. 1976).*
Carbohydrate Res., vol. 45(1), pp. 135–141, (1975).*
Chem. Ber., vol. 108(7), pp. 2254–2260, (1975).*
Tu et al., Youji Huaxue, vol. 8(4): 321–326, (1988).*
Konig Et Al. Chem Ber. 1970, 103, 788.
Smith Et Al. J. Medicinal Chem. 1975, 18, 822.
Hagen Et Al. J. Peptide Protein Res. 1984, 23, 642.
Greene Et Al. Prot. Groups in Org. Syn., J. Wiley & Sons, 1981, 1st ed.
Thaisrivongs Et Al. J. Med. Chem. 1988, 31, 1369.
Hermann Et. Al. Phosphorus, Sulfur & Silicon, 1993, 79, 43.
Filira Et. Al. Int. J. Peptide Protein Res 1990, 36, 86.
Albercio Et. Al. Int. J. Peptide Protein Res 1987 30, 206.
Benoiton Et. Al. Int. J. Peptide Res. 1992, 40, 559.
Farmer, et al., "Speculations on the Design of Nonpeptidic Peptidomimetics", *Trends Pharmacol. Sci. 3:* 362–365 (1982).
Horwell, "Peptoids'from CCK–8", *Spec. Pub. R. Soc. Chem. 65:* 62–72 (1988).
Gallop, et al., "Applications of Combinatorial Technologies to Drug Discovery. 1. Background and Peptide Combinatorial Libraries", *J. Med. Chem. 37:* 1233–1251 (1994).
Gordon, et al., "Applications of Combinatorial Technologies to Drug Discovery. 2. Combinatorial Organic Synthesis, Library Screening Strategies, and Future Directions", *J. Med. Chem. 37:* 1385–1401 (1994).
Suhara, et al., "Peptide–Sugar Hybrids: Like Peptide, Like Oligosaccharide", *Tet. Lett. 38:* 7167–7170 (1997).
Zuckermann Et. Al. J. Am. Chem. Soc., 114, 10646–10647 (1992).
Jung Et. Al. Angewandte Chemie, 31, 367–486 (1992).
Simon Et. Al. Proc. Natl. Acad. Sci. USA, 89, 9367–9371 (1992).
Kessler Et. Al. Angewandte Chemie, 32, 543–544 (1993).
Fuchs Et. Al. Chem. Ber. 108, 2254–2260 (1975).
Giannis Et. Al. Angewandte Chemie, 32, 1244–1267 (1993).
Von Roedern Et. Al. Angewante Chemie, 31, 687–689 (1994).
Shibaev et al. Bioorg. Khim., vol. 13(7): 940–946, (1987).*

* cited by examiner

*Primary Examiner*—Ralph Gitomer
*Assistant Examiner*—Devesh Khare
(74) *Attorney, Agent, or Firm*—David G. Lewis

(57) ABSTRACT

Libraries are synthesized with oligomeric carbopeptoids and carbonucleotoids. Carbopeptoids are oligosaccharides having carbohydrate subunits linked to one another by amide bonds. Carbonucleotoids are oligosaccharides having carbohydrate subunits linked to one another by phosphodiester bonds. Carbopeptoid libraries may be fabricated using automated polypeptide synthesizers. Carbonucleotoid libraries may be fabricated using automated polynucleotide synthesizers.

4 Claims, No Drawings

CARBOPEPTOIDS AND CARBO-NUCLEOTOIDS

This Application is a Divisional of Ser. No. 08/913,035 filed Nov. 20, 1997, now U.S. Pat. No. 6,204,376.

This invention was made with government support under Contract Nos. CA46446 and GM50699 by the National Institutes of Health. The government has certain rights in the invention.

FIELD OF THE INVENTION

The invention relates to oligosaccharides and libraries incorporaiting oligosaccharide. More particularly, the invention relates to oligosaccharides and libraries of oligosaccharides which employ amide and/or phosphodiester linkages for joining adjacent carbohydrate subunits.

BACKGROUND

Carbohydrates are known to mediate many cellular recognition processes. Carbohydrates can serve directly as binding molecules and, in such instances, are essential to the recognition process. A review of the biological role of carbohydrates with respect to cellular recognition phenomena is provided by Sharon et al. (*ScientiicAmerican*, January 1993, 82). The emerging importance of glycobiology is further characterized by Mekelburger et al. (*Angew. Chem. Int. Ed. Engl.* 1992, 31, 1571) and by Dagani et al. (*Chem. Eng. News*, Feb. 1, 1993, 28).

Dysfunctional mediation of cellular recognition processes can lead to disease states. If a cellular recognition process is mediated by an oligosaccharide, then an absence or excess of such oligosaccharide can lead to a dysfunctional mediation of such process. The mediating oligosaccharide may be deficient or absent due to a deficiency of production or due to a high rate of catabolism. If rate of catabolism is excessive, then catabolically resistant analogs of the bioactive oligosaccharide may be preferred as drug candidates as compared to the native bioactive oligosaccharide.

Accordingly, what is needed is a library which includes analogs of known bioactive oligosaccharides. Such a library may be usefully employed for screening drug candidates.

Central requirements for the design of libraries of oligosaccharide analogs include the following:

(a) A need to maximize the potential of the designed oligosaccharides as ligand and drug candidates;

(b) A need to capitalize on existing highly sophisticates technology directed to the synthesis of oligopeptides and oligonucleotides in order to facilitate the rapid and efficient design and construction of oligosaccharides; and (c) A need for flexibility with respect to synthesizing either single target molecules or large libraries of target molecules simultaneously.

Methodologies for synthesizing biopolymers are well developed for peptides, nucleic acids, and saccharides. Segments of oligopeptides and of oligonucleotides can now be routinely synthesized both in solution and in the solid phase, manually and/or on automated systems. The synthesis of such structures is facilitated by the availability of efficient techniques and sophisticated instrumentation for synthesizing peptide and phosphate bonds with high yields. The synthesis of oligopeptides and oligonucleotides is also facilitated by the absence of stereocenters in these linkages. In contrast, technology for the construction of oligosaccharides is comparatively less sophisticated and efficient. Synthetic methods for constructing oligosaccharides give comparatively lower yields and are complicated by the two isomer possibilities ($\alpha$ and $\beta$) in glycoside bond formation.

Techniques and chemical methods for simultaneously synthesizing multiple oligopeptides, e.g. 100–150 completely different peptides having lengths of up to 20 amino acid residues, are reviewed by Jung, G. et al. (*Angew. Chem, Int. Ed. Engl.* 1992, 31, 367–383—incorporated therein by reference). Such techniques facilitate the construction of oligopeptide libraries.

Simon, et al. (*Proc, Natl. Acad. Sci. USA,* 1992, 89, 9367–9371) disclose oligopeptide analogs in which amino acid side chain groups are attached not to conventional peptide backbone carbons but to peptide backbone nitrogens. Such analogs are termed peptoids. Simon also discloses the construction of peptoid libraries as a modular approach to drug discovery. Simon's oligopeptoids are shown by calculation to have greater conformational freedom as compared to conventional oligopeptides. Accordingly, oligopeptoids are thought to have greater potential as pharmaceutically useful binding ligands as compared to conventional oligopeptides having close sequence homology to such oligopeptoids.

Von Roedern et al. disclose a carbohydrate amino acid (*Angew. Chem, Int. Ed. Engl.* 1994, 31, 687–689). Although von Roedern discloses that carbohydrate amino acids may be coupled to peptides, he does not disclose that they may also be polymerized so as to form oligosaccharides.

SUMMARY

A first aspect of the invention involves the molecular design and chemical synthesis of a class of carbohydrates designated as carbopeptoids (CPD's). Glycopeptoids are preferred carbopeptoids. Carbopeptoids and glcopeptoids are oligosaccharides which employ peptide-like amide bonds for linking the various carbohydrate subunits within an oligomer assembly. Amide bond formation may be achieved by employing oligopeptide synthesis technology and instrumentation. The method allows for the design and synthesis of specific compounds for biological and pharmacological investigations. The method also allows for the generation of libraries of compounds for biological and pharmacological screening. Conventional screening techniques employed with respect to peptide and peptoid libraries (Simon et al., supra) may also be employed with respect to carbopeptoid libraries. The design takes advantage of the multifunctionality of carbohydrate subunits to maximize the binding properties of the molecules. The ease and high efficiency by which the peptide-like linkages can be constructed make the synthesis of these molecules a practical proposition. Furthermore, non-carbohydrate units may be inserted into the sequence making this approach even more flexible and versatile for the generation of new libraries of organic compounds.

More particularly, the invention is directed to a oligomeric carbopeptoid or glycopeptoid compound having carbohydrate amino acid subunits (CA's) or glycoside amino acid subunits (GA's) coupled to one another via an amide linkage. The amide linkage may be represented by the formula $CA_1$-(CA—NH)-$CA_2$. The amide linkage (CO—NH) includes a carbonyl carbon and an amido nitrogen. A first carbohydrate amino acid subunit $CA_1$ or glycoside amino acid subunit $GA_1$ has an anomeric carbon bonded to the carbonyl carbon of the amide linkage. The anomeric carbon of the first carbohydrate amino acid subunit $CA_1$ forms a C-glycosidic bond with the carbonyl carbon of the amide linkage and maintains the carbohydrate in a closed ring configuration. A second carbohydrate amino acid subunit $CA_2$ has a non-anomezic carbon bonded to the amido nitrogen of the amide linkage. The second carbohydrate amino acid subunit $CA_2$, like the first amino acid subunit $CA_1$, may include an anomeric carbon bonded to the carbonyl carbon of a second amide linkage linking the second carbohydrate amino acid subunit $CA_2$ to a third carbohydrate amino acid subunit $CA_3$, etc. In this instance, the anomeric carbon of the second carbohydrate amino acid subunit $CA_2$ forms a C-glycosidic bond with the carbonyl carbon of the amide linkage and maintains the carbohydrate in a closed ring a configuration. On the other hand, if the second carbohydrate amino acid subunit $CA_2$ is a terminal subunit, then its anomeric carbon may form a hemiacetal, a hemiketal, or a glycoside.

The invention is also directed to a process for synthesizing the above oligomeric carbopeptoid or glycopeptoid compound. The synthetic process involves the coupling of two or more carbohydrate amino acid subunits (CA's) or glycoside amino acid subunits (GA's) to one another by means of amide linkages.

The invention is also directed to libraries of oligomeric carbopiaptoid or glycopeptoid compounds. Such libraries are employable for drug screening. Each oligomeric carbopeptoid or glydopeptoid compound includes at least two carbohydrate amino acid subunits (CA's) or glycoside amino acid subunits (GA's) coupled to one another via an amide linkage as indicated above. The invention is also directed to an improved process for synthesizing the above library of oligomers. The process employs an elongation step for coupling the subunits to one another to produce the oligomers. In the elongation step, two carbohydrate amino acid subunits (CA's) or glycoside amino acid subunits (GA's) are coupled to one another via an amide linkage as indicated above.

The invention is also directed to chemical intermediates for producing oligomeric carbopeptoids. A first chemical intermediate is a derived carbohydrate amino acid having an anomeric carbon and non-anomeric carbons. The anomeric carbon is substituted with a carboxyl radical. Each of the non-anomeric carbons is substituted with a radical selected from the group consisting of blocked hydroxyl, blocked amino, differentially protected amino, and hydrogen, with the proviso that at least one radical is a differentially protected amino. A second chemical intermediate is a derived carbohydrate amino acid similar to the first except that the non-anomeric carbons are substituted with a radical selected from the group consisting of blocked hydroxyl, blocked amino, unprotected amino, and hydrogen, with the proviso that at least one radical is an unprotected amino and at least one radical is a blocked hydroxyl or amino.

A second aspect of the invention involves the molecular design and chemical synthesis of a class of carbohydrates designated as carbonucleotoids (CND's). Carbonucleotoids are oligosaccharides which employ oligonucleotide-like phosphate bonds for linking the various carbohydrate subunits within an oligomer assembly. Phosphate bond formation may be achieved by employing technology and instrumentation developed for oligonucleotide synthesis. The phosphate bonds employed within carbonucleotoids are convenient linkages for coupling these units. The ease and high efficiency by which the oligonucleotide-like linkages can be constructed make the synthesis of these molecules a practical proposition.

The disclosed methods are characterized by their versatility and practicality. The methods may exploit conventional solid phase and automated synthesis techniques for producing carbopeptoids and carbonucleotoids in large scale.

More particularly, the second aspect of the invention is directed to an oligomeric carbonucleotoid molecule comprising carbohydrate C-glycoside subunits (CG's) coupled to one another via a phosphodiester linkage. The phosphodiester linkage may be represented by the structure: $CG_1$-$C_1$'-(O—PO(OH)—O)-$CG_2$. The first carbohydrate C-glycoside subunit ($CG_1$-$C_1$') has an anomeric carbon forming a C-glycosidic bond with a carbon $C_1$'. In turn the carbon $C_1$' is bonded to the phosphodiester linkage. The second carbohydrate C-glycoside subunit $CG_2$ has a non-anomeric carbon bonded to the phosphodiester linkage. The invention is also directed a process for synthesizing the oligomeric carbonucleotoid molecule. The process employs a coupling step wherein two or more carbohydrate C-glycoside subunits (CG's) are coupled by means of a phosphodiester linkage as indicated above.

The second aspect of the invention is also directed to libraries of oligomeric carbonucleotoid molecules. The libraries are employable for drug screening. Each oligomeric carbonucleotoid molecule including at least two carbohydrate C-glycoside subunits (CG's) coupled to one another by means of a phosphodiester linkage as indicated above. The invention is also directed to an improved process for synthesizing a library of oligomers. The process employs an elongation step wherein subunits are coupled to one another to produce the oligomers. The improvement is directed to the use of phosphodiester linkage linkages for linking the C-glycoside subunits as indicated above.

The second aspect of the invention is also directed to derived carbohydrate C-glycosides having an anomeric carbon and non-anomeric carbons. The anomeric carbon forms a C-glycosidic bond with carbon $C_1$'. In turn, the carbon $C_1$' is bonded to an phosphoramidite. Each of the non-anomeric carbons is substituted with a radical selected from the group consisting of blocked hydroxyl, differentially protected hydroxyl, and hydrogen, with the proviso that at least one radical is a differentially protected hydroxyl. An alternative derived carbohydrate C-glycoside is similar to the above except that each of the non-anomeric carbons is substituted with a radical selected from the group consisting of blocked hydroxyl, unprotected hydroxyl, and hydrogen, with the proviso that at least one radical is an unprotected hydroxyl and at least one radical is a blocked hydroxyl.

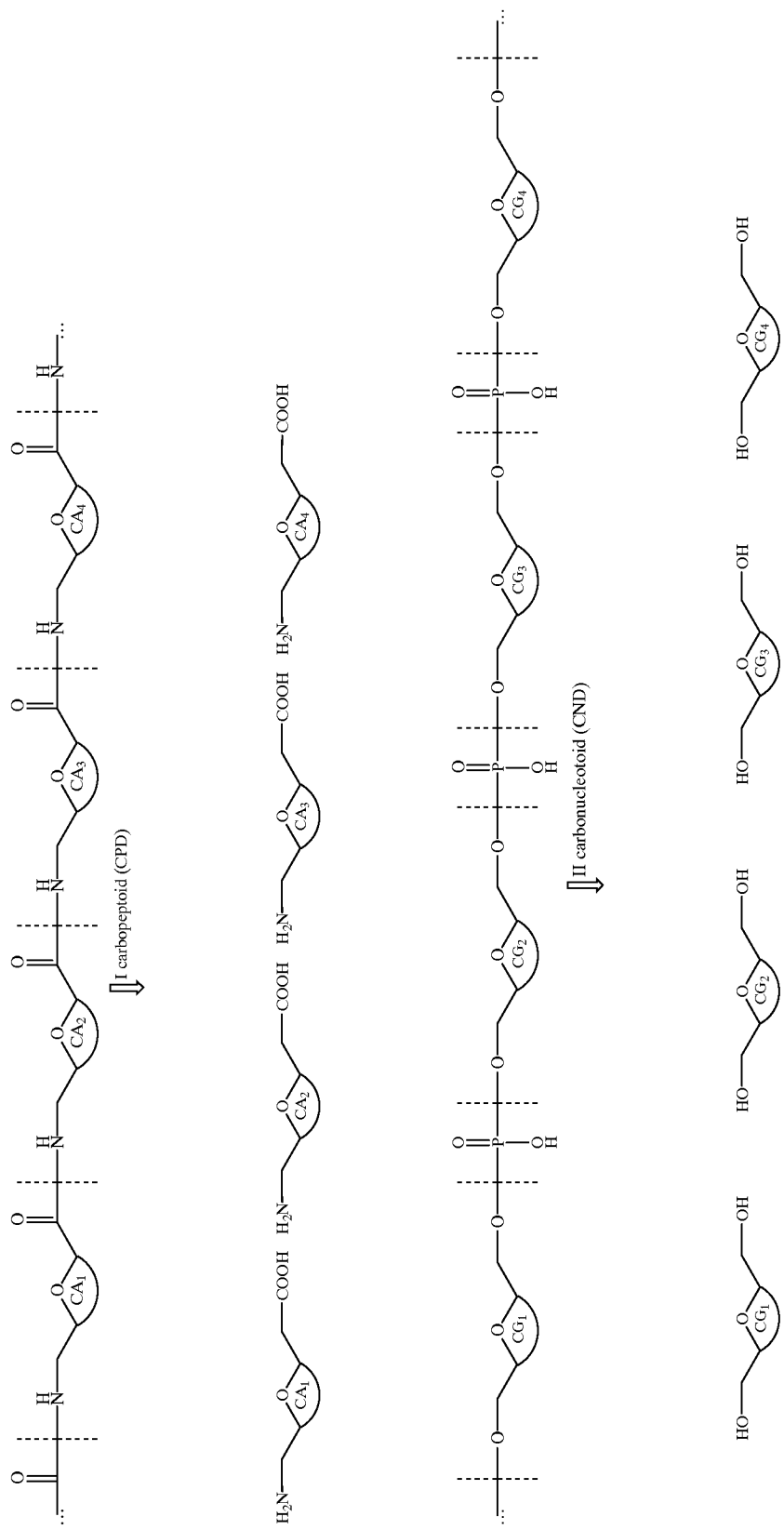

DETAILED DESCRIPTION

Retrosynthetic schemes for carbopeptoids (compound I) and carbonucleotoids (compound II) are illustrated in Scheme 1.

The carbopeptoids (CPD's) are oligomers having repeating carbohydrate subunits linked to one another by means of amide linkage units. More particularly, the carbonyl carbon of each amide linkage unit is bonded to the anomeric carbon of a carbohydrate subunit. Similarly, the amide nitrogen of the amide linkage unit is bonded to a non-anomeric carbon. The retrosynthetic scheme suggests that the amide bond may be split and that the preferred starting materials are carbohydrate amino acids.

Carbonucleotoids (CND's) are oligosaccharides in which carbohydrate C-glycoside subunits (CG's) are linked to one another by means of phosphodiester bonds. More particularly, the retrosynthetic scheme suggests that the phosphate group may be eliminated, yielding hydroxylated starting material.

Scheme 2 illustrates representative carbohydrate amino acid subunits (CA's) and carbohydrate C-glycoside subunits (CG's). Preferred carbohydrate amino acid subunits (CA's) include the following:

- D-glucose having an unprotected carboxyl at the anomeric C(1) position, an unprotected amino group at the C(6) position, and blocked hydroxyls at the C(2), C(3), and C(4) positions;
- D-mannose having an unprotected carboxyl at the anomeric C(1) position, an unprotected amino group at the C(6) position, and blocked hydroxyls at the C(2), C(3), and C(4) positions;
- D-galactose having an unprotected carboxyl at the anomeric C(1) position, an unprotected amino group at the C(6) position, and blocked hydroxyls at the C(2), C(3), and C(4) positions;

Scheme 2
Structures of carbohydrate aminoacids (CA's) and C-glycosides (CG's)

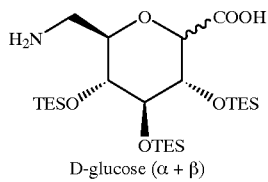
D-glucose (α + β)

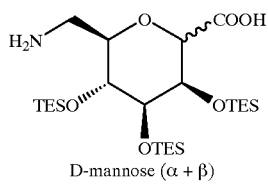
D-mannose (α + β)

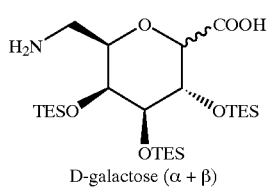
D-galactose (α + β)

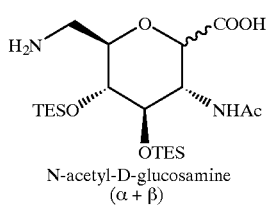
N-acetyl-D-glucosamine (α + β)

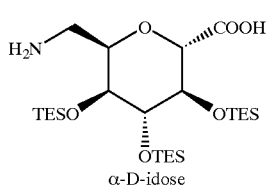
α-D-idose

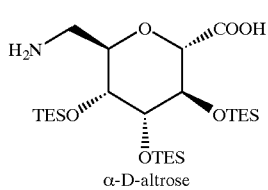
α-D-altrose

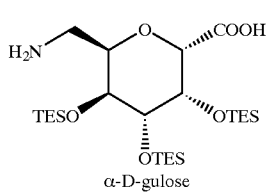
α-D-gulose

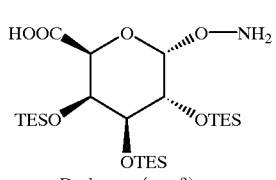
D-glucose (α + β)

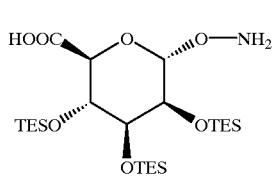
D-mannose (α + β)

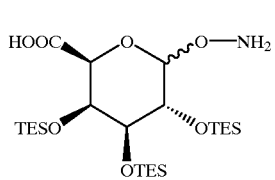
D-galactose (α + β)

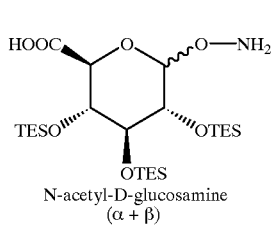
N-acetyl-D-glucosamine (α + β)

-continued

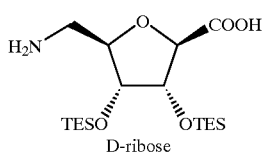
24
D-ribose

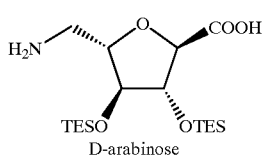
26
D-arabinose

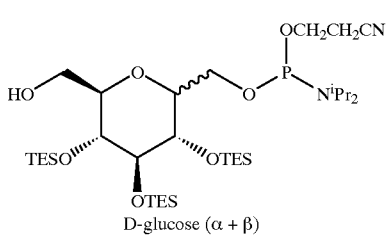
28
D-glucose (α + β)

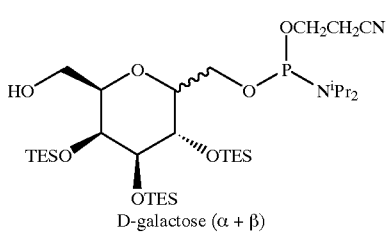
32
D-galactose (α + β)

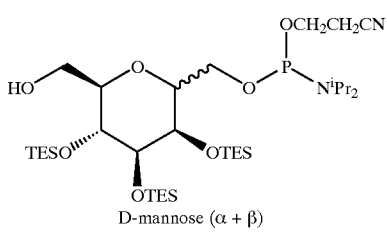
30
D-mannose (α + β)

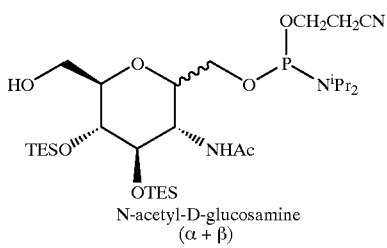
34
N-acetyl-D-glucosamine (α + β)

N-acetyl-D)-glucosamine having an unprotected carboxyl at the anomeric C(1) position, an unprotected amino group at the C(6) position, a blocked amino group at the C(2) position, and blocked hydroxyls at the C(3) and C(4) positions;

α-D-idose having an unprotected carboxyl at the anomeric C(1) position, an unprotected amino group at the C(6) position, and blocked hydroxyls at the C(2), C(3), and C(4) positions;

α-D-altrose having an unprotected carboxyl at the anomeric C(1) position, an unprotected amino group at the C(6) position, and blocked hydroxyls at the C(2), C(3), and C(4) positions;

α-D-gulose having an unprotected carboxyl at the anomeric C(1) position, an unprotected amino group at the C(6) position, and blocked hydroxyls at the C(2), C(3), and C(4) positions;

α-D-glucose having an unprotected O-glycosidic amino at the anomeric C(1) position, an unprotected carboxyl as the C(6) position, and blocked hydroxyls at the C(2), C(3), and C(4) positions;

D-mannose having an unprotected O-glycosidic amino at the anomeric C(1) position, an unprotected carboxyl as the C(6) position, and blocked hydroxyls at the C(2), C(3), and C(4) positions;

D-galactcse having an unprotected O-glycosidic amino at the anomeric C(1) position, an unprotected carboxyl as the C(6) position, and blocked hydroxyls at the C(2), C(3), and C(4) positions;

N-acetyl-D-glucosamine having an unprotected O-glycosidic amino at the anomeric C(1) position, an unprotected carboxyl as the C(6) position, a blocked amino group at the C(2) position and blocked hydroxyls at the C(3) and C(4) positions;

D-ribose having an unprotected carboxyl at the anomeric C(1) position, an unprotected amino group at the C(5) position, and blocked hydroxyls at the C(2) and C(3) positions; and D-arabinose having an unprotected carboxyl at the anomeric C(1) position, an unprotected amino group at the C(5) position, and blocked hydroxyls at the C(2) and C(3) positions.

Preferred carbohydrate amino acid subunits (CA's) include the following:

D-glucose having a C(1) $C_{1'}$-glycosidic carbon bonded to a phosphoramidite, an unprotected hydroxyl at the C(6) position and blocked hydroxyls at the C(2), C(3), and C(4) positions;

D-mannose having a C(1) $C_{1'}$-glycosidic carbon bonded to a phosphoramidite, an unprotected hydroxyl at the C(6) position and blocked hydroxyls at the C(2), C(3), and C(4) positions;

D-galactose having a C(1) $C_{1'}$-glycosidic carbon bonded to a phosphoramidite, an unprotected hydroxyl at the C(6) position and blocked hydroxyls at the C(2), C(3), and C(4) positions; and N-acetyl-D-glucosamine having a C(1) $C_{1'}$-glycosidic carbon bonded to a phosphoramidite, an unprotected hydroxyl at the C(6) position, a blocked amino at the C(2) position, and blocked hydroxyls at the C(3) and C(4) positions.

Scheme 3 outlines a preferred synthesis of suitably protected carbohydrate amino acid subunits (CA's) from D-glucose, i.e. compound 46.

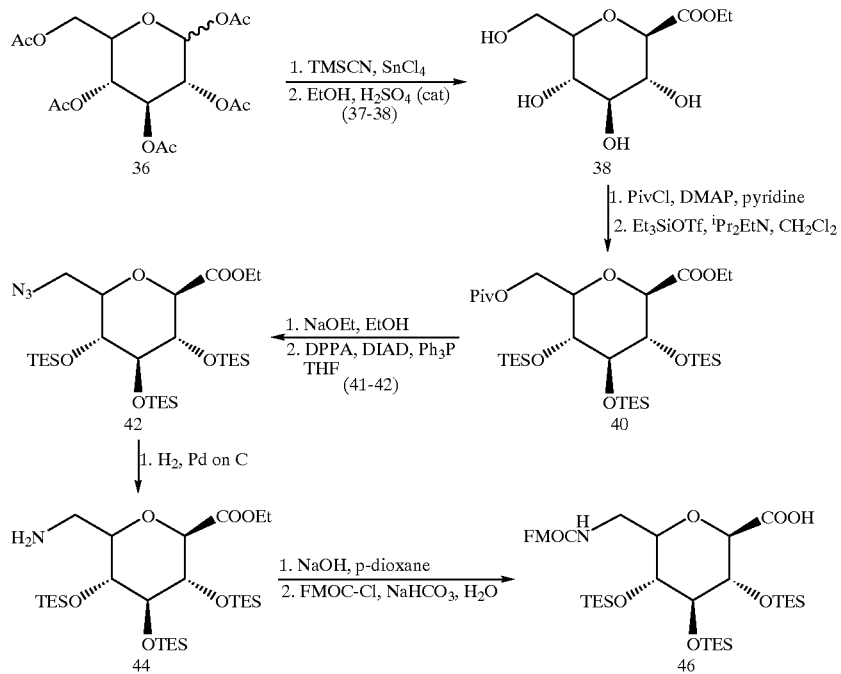
Scheme 4 outlines the synthesis of suitably protected carbohydrate amino acid subunits (CA's) from N-acetyl-D-glucosamine, i.e. compound 62.
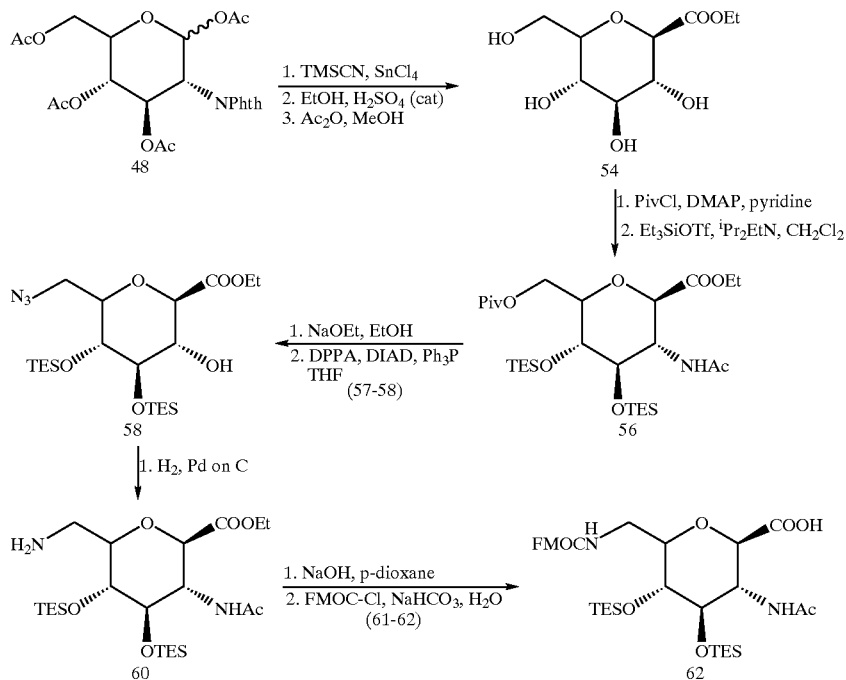

Scheme 5 summarizes the synthesis of hexamer 74, i.e glucose-glucosamine hetero carbopeptoid (CPD).
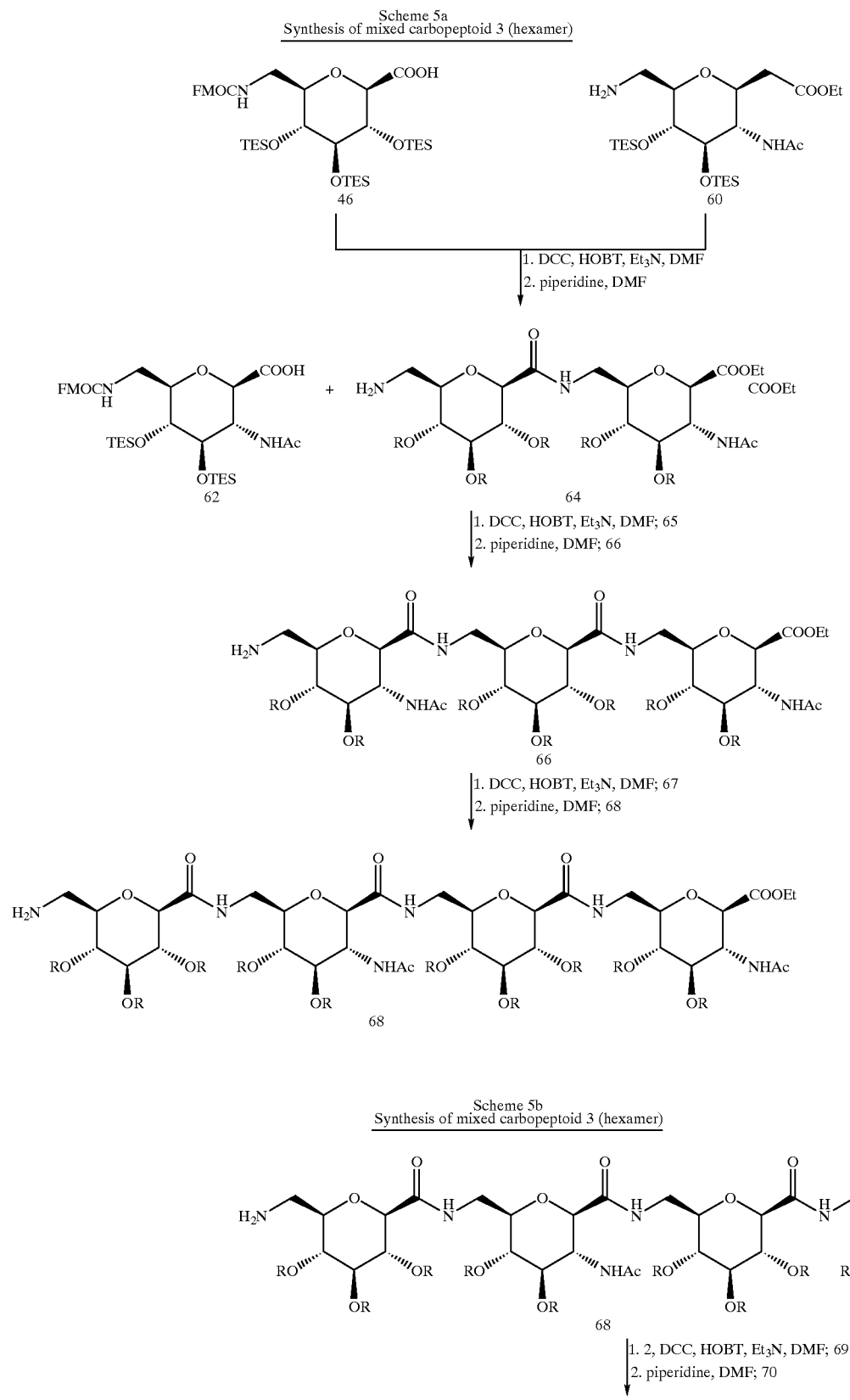

-continued
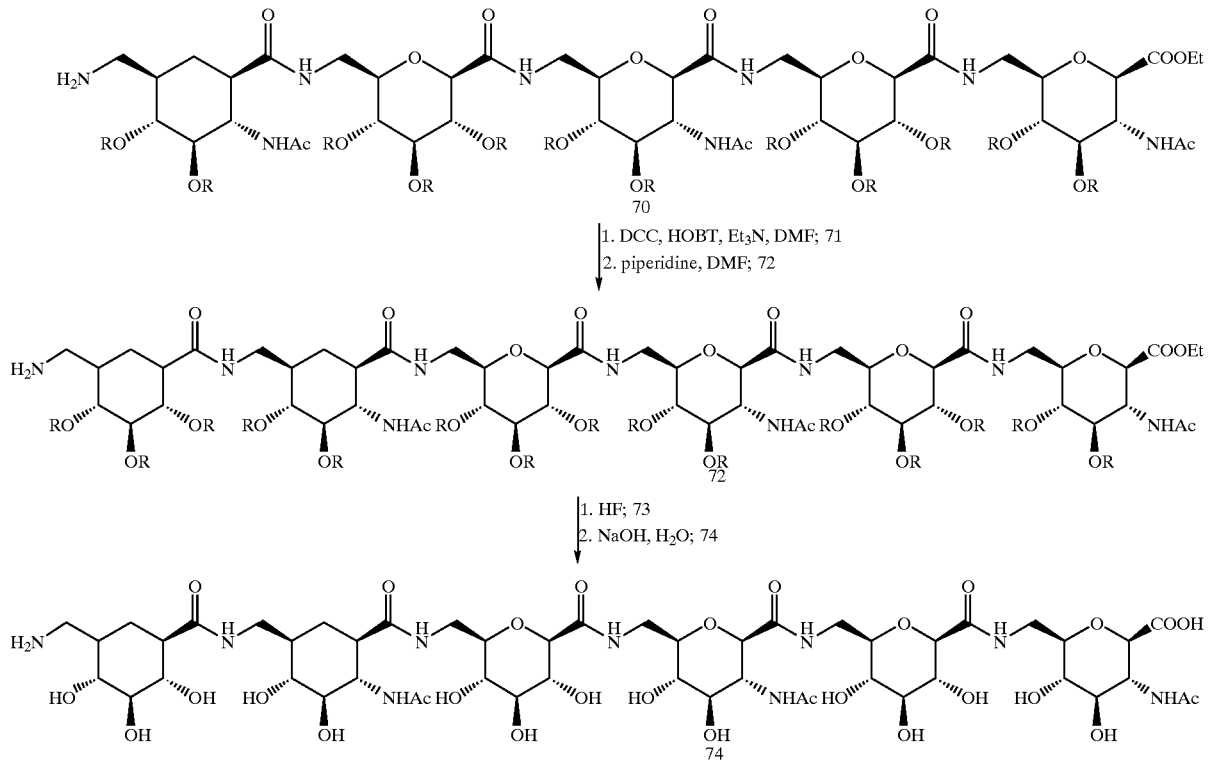
Scheme 6 illustrates the construction of suitably protected and activated C-glycoside subunits (CG's) corresponding to glucose.
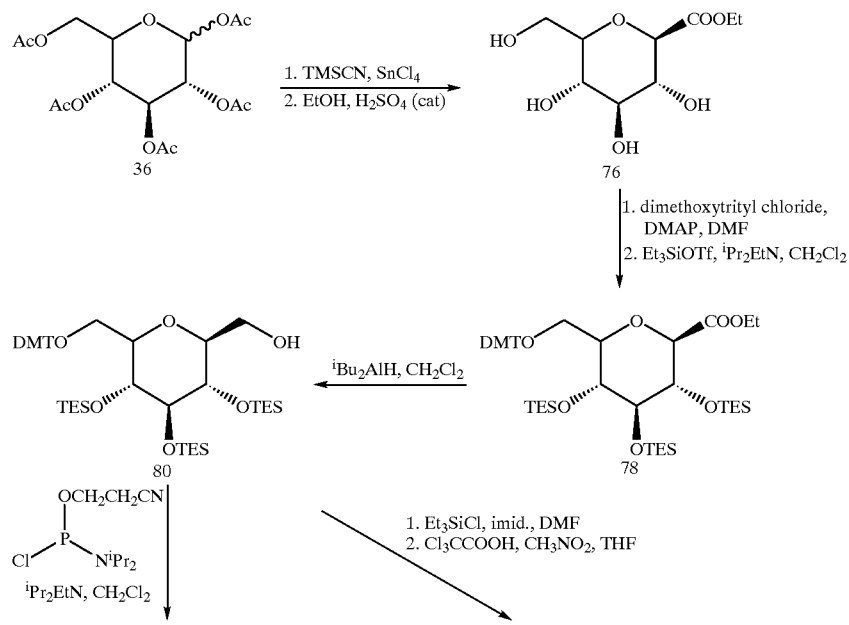

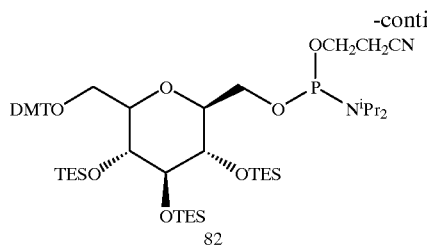
82
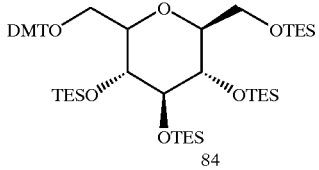
84
Scheme 7 illustrates the construction of suitably protected and activated C-glycoside subunits (CG's) corresponding to glucosamine.
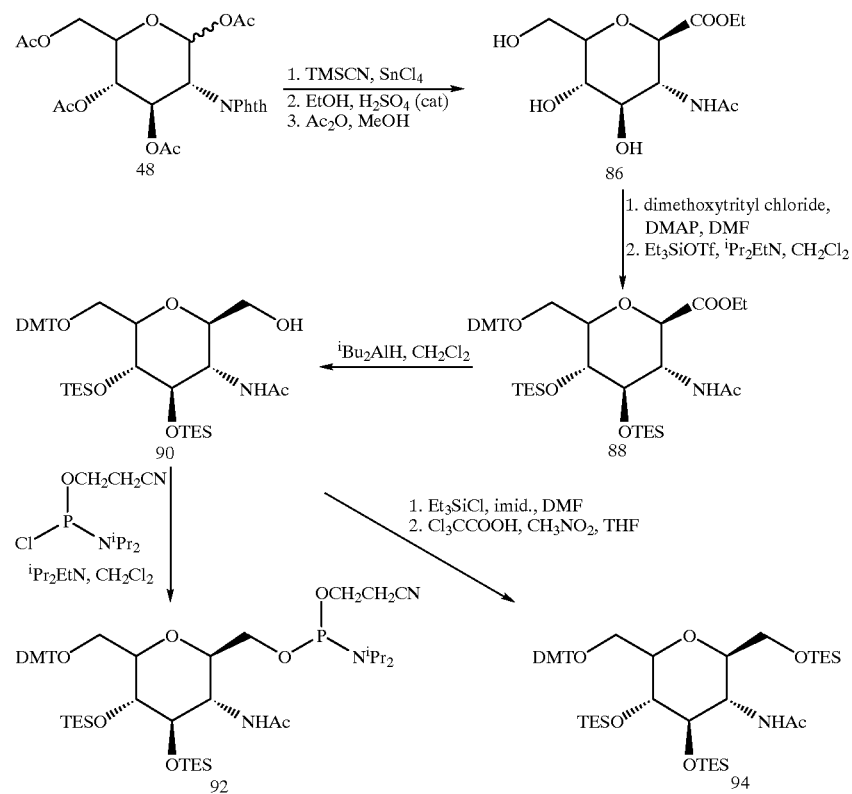
Scheme 8 summarizes the synthesis of hexamer 116, i.e. glucose-glucosamine hetero carbonucleotoid (CND).
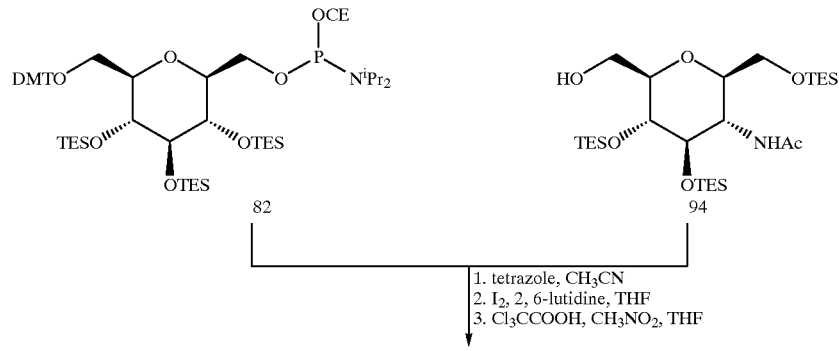

-continued
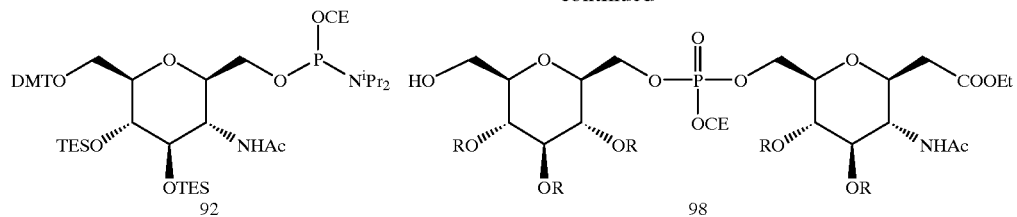
1. tetrazole, CH₃CN
2. I₂, 2,6-lutidine, THF
3. Cl₃CCOOH, CH₃NO₂, THF
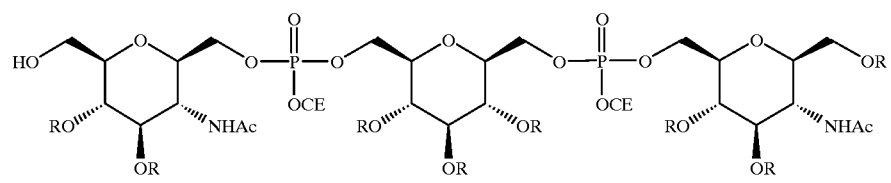
1. tetrazole, CH₃CN
2. I₂, 2,6-lutidine, THF
3. Cl₃CCOOH, CH₃NO₂, THF
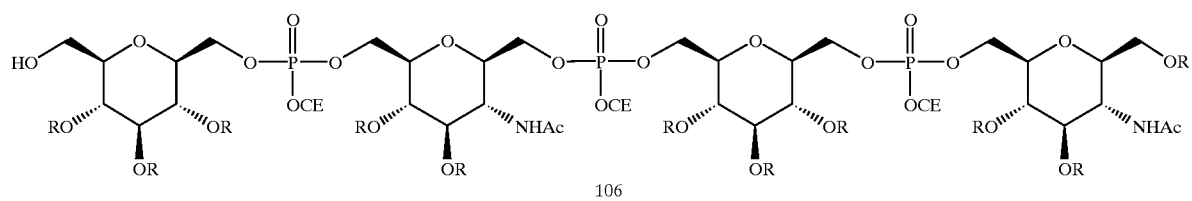

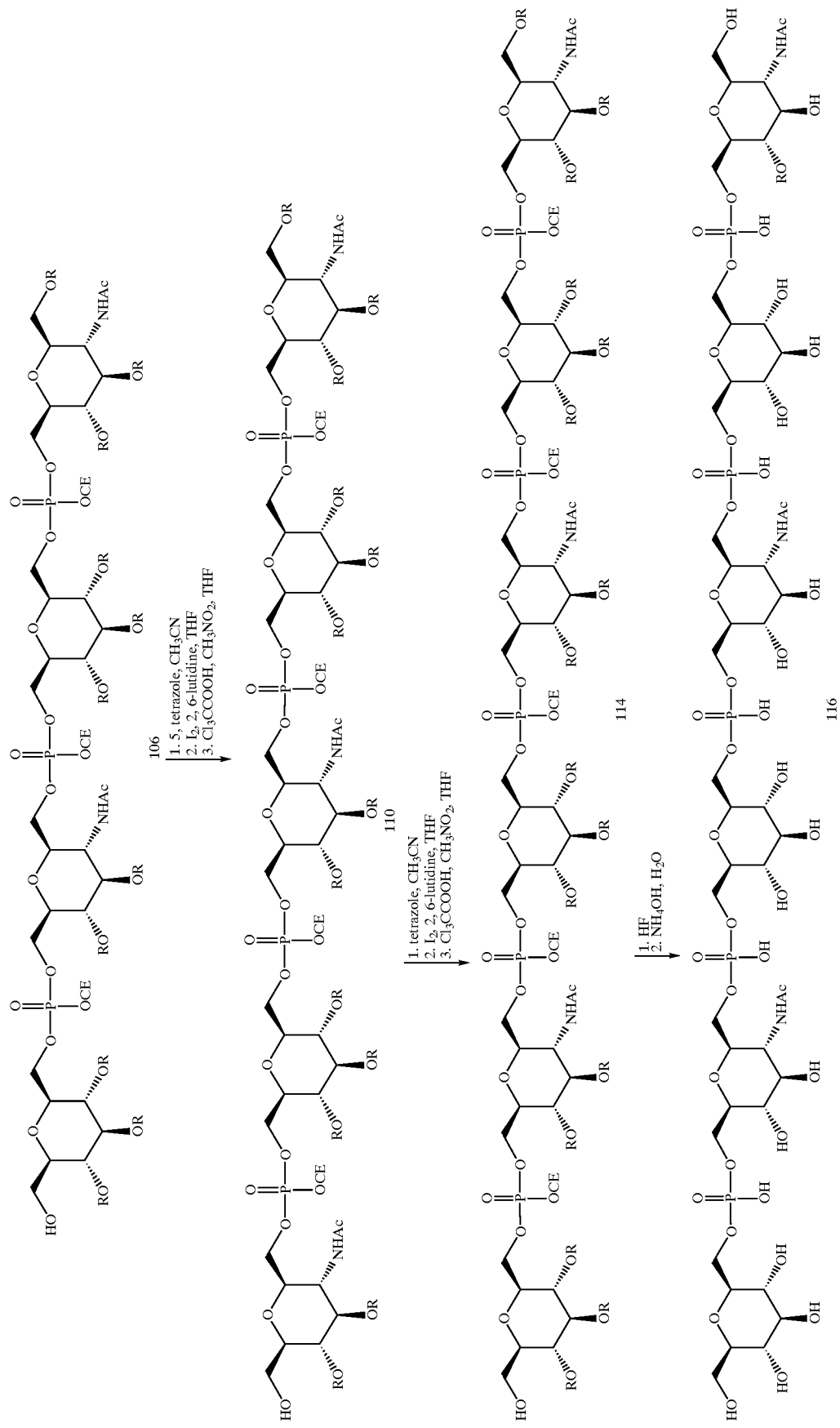

The chemistries illustrated in Schemes 5 and 8 for synthesizing heterohexamer CPD 74 and heterohexamer CND 116 can also be employed for synthesizing homohexamer CPD's 118 (glucose) and 120 (glucosamine) and homohexamer CND's 122 (glucose) and 124 (glucosamine).

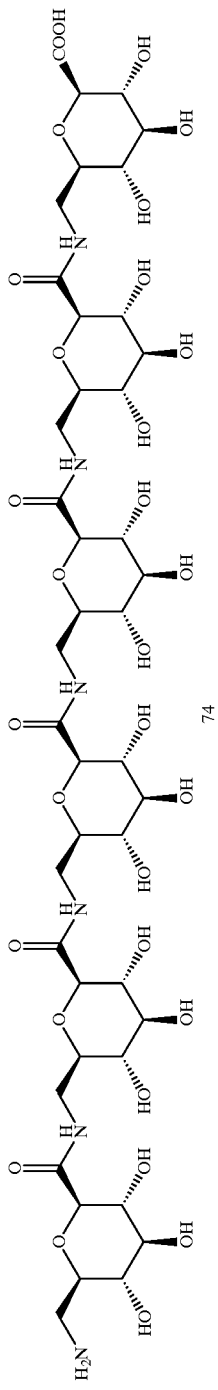
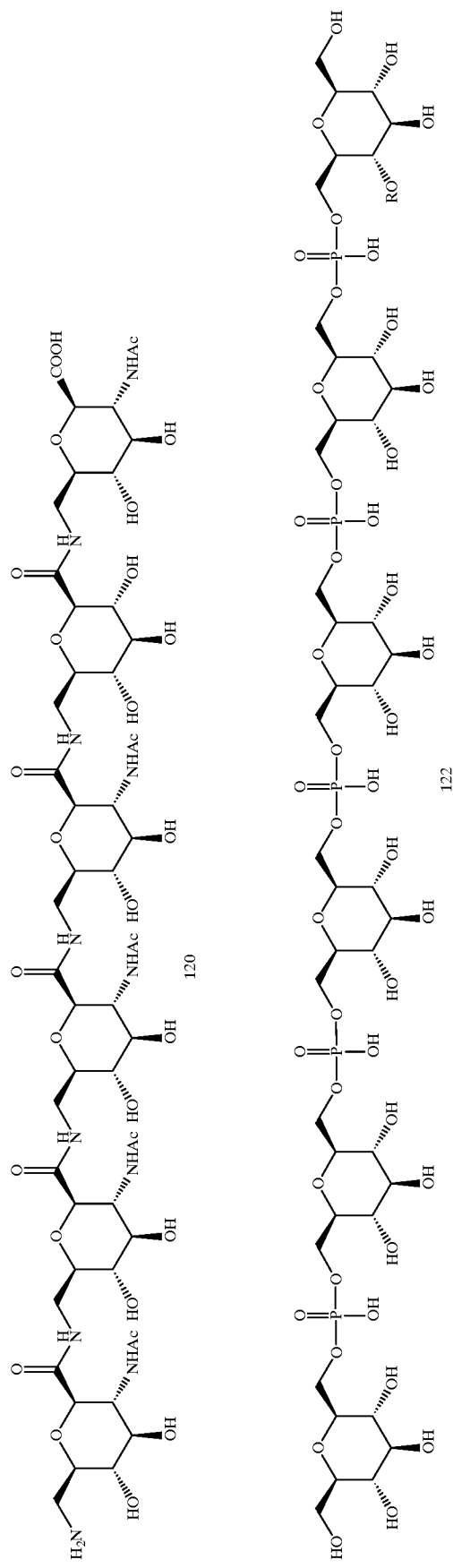
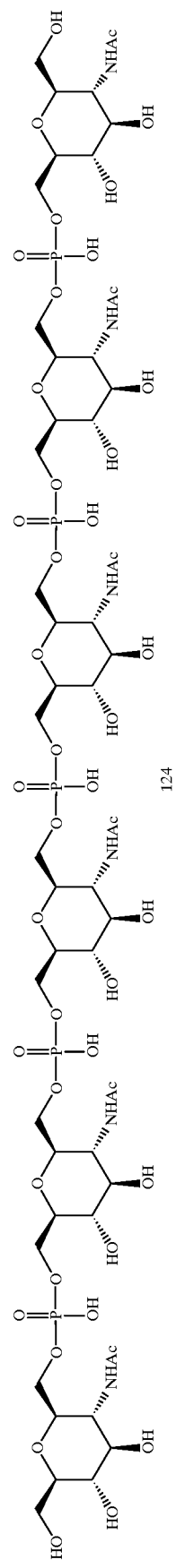

In analogy with the construction of oligopeptide and oligonucleotide libraries, a oligosaccharide carbopeptoid (CPD) library may be constructed by performing using a split synthesis method of oligomerization as illustrated in Scheme 500 for carbopeptoids and Scheme 550 for carbonucleotoids. For example, the split synthesis may employ beads upon which to build the oligomers. Beads are aliquoted into each of a several reaction vessels, each reaction vessel containing a different core molecule. The core molecules are then allowed to attach to the beads. The beads are washed, mixed with one another, and then re-aliquoted (split) into a second set of reaction vessels for addition of a second core molecule to the first added core molecule. The process is then reiterated until the oligomerization process is complete. The resultant library of oligosaccharides may then be screened using conventional methods developed for oligopeptide and oligonucleotide libraries. Screening an oligosaccharide library can lead to the identification of individual oligosaccharide components within the library having binding activity and/or bioactivity.

The above oligosaccharide libraries (CPD and CND) may be enlarged by introducing additional functionalities into the basic CA's and CG's.

The above oligosaccharide libraries (CPD and CND) may be further enlarged by enlarging the pool of free functional grouts on the CA's and CG's and employed this enlarged pools of CA's and CG's during the respective split synthesis processes.

Scheme 20 illustrate a protocol published by Fuchs, E. F. et al. (J. Chem Ber. 1975, 108, 2254) for the synthesis of CA 45 and 46 from glucose pentaacetate. Additionally, Scheme 20 illustrates a synthetic route for CG 82, also starting from glucose pentaacetate. The reagents and conditions for synthesizing CG 82 are provided as follows:

Steps (a)–(d): according to Fuchs (supra).
Step (e): (1) DMTCl, DMAP, Pyridine; room temperature.
    (2) TESfl; 0° C.
Step (f): DIBAL-H, $CH_2Cl_2$; −78° C.; and
Step (g): $(NCCH_2CH_2)$ $(NiPr_2)PCl$, tetrazole, $CH_2Cl_2$.

The reagents and conditions for synthesizing CA 46 from CA 45 are provided in Step M as follows:

Step (m): FMOC-Cl, $K_2CO_3$, THF, $H_2O$; 0° C.

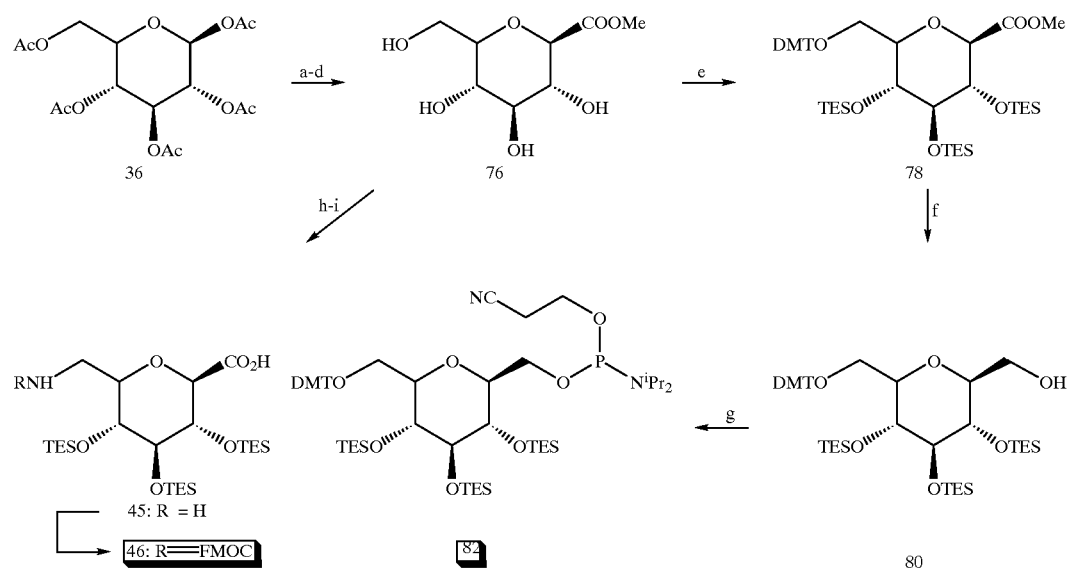

Scheme 20
Conventional route to CAs and a variation for the synthesis of CG

*Reagents and conditions:*
(a) - (d) corresp. Lit.:
(e) (1) DMTCl, DMAP, Py; RT.
    (2) TESfl; 0° C.
(f) DIBAL-H, $CH_2Cl_2$; -78° C.
(g) $(NCCH_2CH_2)(NiPr_2)PCl$, tetrazole $CH_2Cl_2$.
(m) FMOC—Cl, $K_2CO_3$, THF, $H_{20}$; 0° C.

A synthetic route for producing C-glycosides (CG's) with β-configuration at the former anomer center is illustrated in Scheme 21. The starting material (compound 36) is commercially available. The reagents and conditions for synthesizing CG 181 and CG 185 are as follows:

Step (a): $Co_2(CO)_8$, $HSiEt_2Me$, CO.
Step (b): (1) AcOH, $H_2O$, THF;
    (2) $RuCl_3$, $NaIO_4$, $CH_3CN$, $H_2O$, $CCL_4$, room temperature;

Step (c): NaOMe, MeOH;
Step (d): (1) DMTCl, DMAP, Pyridine, room temperature;
(2) TESOTf;
Step (e): BH₃-THF;
Step (f) (NCCH₂CH₂) (NiPr₂)PCl, tetrazole, Ch₂Cl₂;

Step (g): (1) 1 equiv TsCl. base;
(2) TESOTf;
Step (h): NaN₃;
Step (i): H₂, Pd(OH)₂—C;
Step (j): FMOC-Cl, base.

Scheme 21
Synthesis of C-glycosides with β-configuration at the former anomeric center

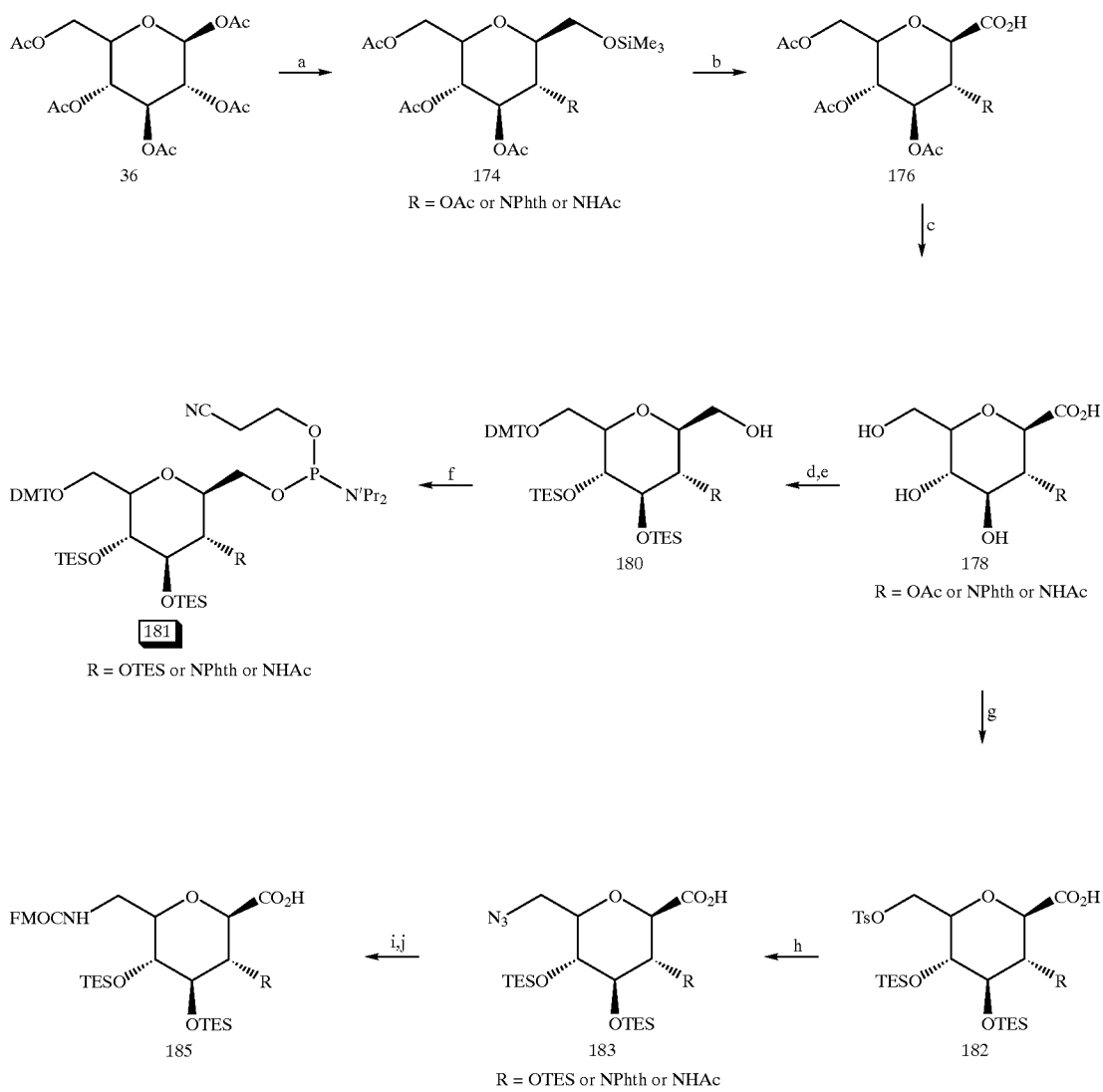

Reagents and conditions:
(a) Co₂(CO)₈, HSiEt₂Me, CO.
(b) (1) AcOH, H₂O, THF;
  (2) RuCl₃, NaIO₄, CH₃CN, H₂O, CCl₄, RT.
(c) NaOMe, MeOH.
(d) (1) DMTCl, DMAP, Py, RT:
  (2) TESOTF.
(e) BH₃-THF.
(f) (NCCH₂CH₃)(NiPr₂)PCl, tetrazole, CHCl₂.
(g) (1) 1 equiv TsCl, base:
  (2) TESOTf.
(H) NaN₃.
(i) H₂, Pd(OH)₂-C.
(j) FMOC-Cl, base.

Scheme 22
Synthesis of C-glycosides with α-configuration at the former anomeric center

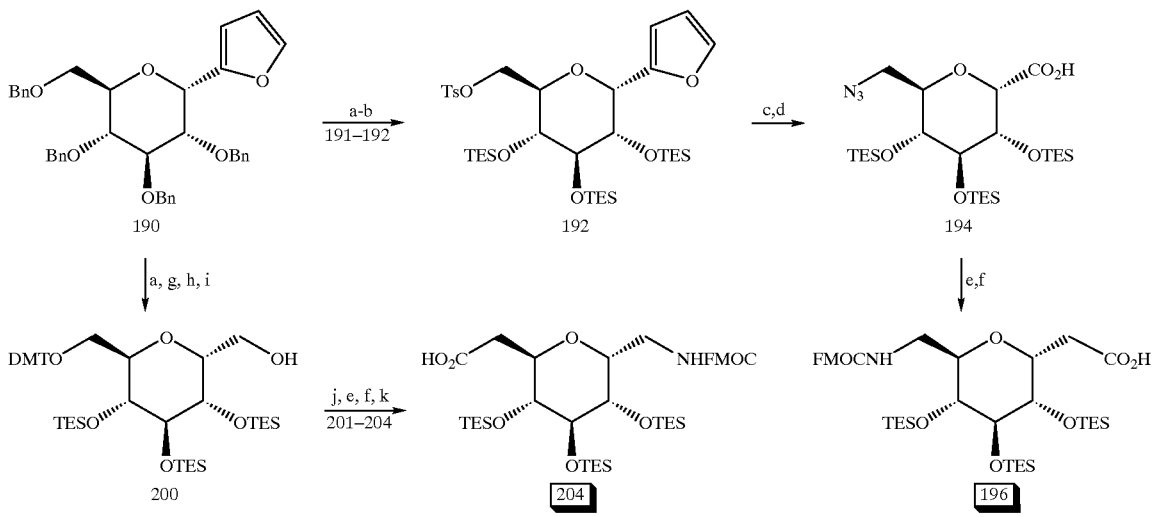

Reagents and conditions:
(a) reductive debenzylation.
(b) (1) 1 equiv TsCl, base;
    (2) TESOTf.
(c) NaN$_3$.
(d) RuCl$_3$, NaIO$_4$, CH$_3$CN, H$_2$O, CCl$_4$.
(e) H$_2$, Pd-C.
(f) FMOC-Cl, base.
(g) (1) DMTCl, DMAP, Py, RT;
    (2) TESOTf.
(h) (1) RuCl$_3$, NaIO$_4$, CH$_3$CN, H$_2$O, CCl$_4$;
    (2) CH$_2$N$_2$.
(i) DIBAL-H.
(j) PPh$_3$, DIAD, diphenyl phosphoryl azide (DPPA), THF.
(k) KMnO$_4$, t-BuOH, buffer.

Synthetic routes for producing with C-glycosides with α-configurations at the former anomeric center, i.e. CG 196 and CG 1204, are illustrated in Scheme 22. The common starting material for these synthetic routes (compound 190) is disclosed by Schmidt, R. R. et al. (*Liebigs Ann. Chem.* 1987, 825). The reagents and conditions for the reactions leading to CG 196 and CG 204 are as follows:

Step (a): reductive debenzylation;

Step (b): (1) equiv TsCl. base;
(2) TESOTf.

Step (c): NaN$_3$.

Step (d): RuCl$_3$, NaIO$_4$, CH$_3$CN, H$_2$O, CCl$_4$.

Step (e): H$_2$, Pd—C.

Step (f): FMOC-Cl, base.

Step (g): (1) DMTCl, DMAP, Pyridine, room temperature;
(2) TESOTf.

Step (h): (1) RuCl$_3$, NaIO$_4$, CH$_3$CN, H$_2$O, CCl$_4$;
(2) CH$_2$N$_2$.

Step (i): DIBAL-H.

Step (j): PPh$_3$, DIAD, diphenyl phosphoryl azide (DPPA), THF.

Step (k): KMnO$_4$, t-BuOH, buffer.

Reactions for the development of the galactose derived C-glycoside 138 into protected CA's and diols is illustrate in Scheme 23. The common starting material for these synthetic routes (compound 138) is disclosed by Petrus, L. et al. (*Chem. zvesti.* 1982, 36, 103). The reagents and conditions required for the synthesis of compound 209, compound 214, compound 220, and compound 224 are indicated below:

Step (a): (1) 1.1 equivalent DMTCl, DMAP, Pyridine, 12 hour, 20° C.;
(2) TesOTf, CH$_2$, 0° C., 1 hour, 83%.

Step (b): (1) LAH, ether, reflux, 2 hour;
(2) FMOC-Cl, K$_2$CO$_3$, THF, H$_2$O, 0° C., 1 hour, 55%;

Step (c): 10% HCOOH in CH$_2$Cl$_2$, 0° C., 2 minutes, 100%.

Step (d): RuCl$_3$, NaIO$_4$, CH$_3$CN, H$_2$O, CCl$_4$, 20° C., 10 minutes, 54%.

Step (e): (1) 1 equiv. TsCl, base;
(2) TESOTf.

Step (f): NaN$_3$.

Step (g): oxidative NEF.

Step (h): Pd—C, H$_2$.

Step (i): FMOC-Cl, base.

Step (j): (1) 1 equiv. PivCl, base;
(2) TESOTf.

Step (k): (1) oxidative Nef; (2) CH$_2$N$_2$.

Step (l): DIBAL-H.

Step (m): DMTCl, DMAP, Pyridine.

Step (n): LAH.

Step (o): Nef reaction

Step (p): LAH.

Scheme 23
Development of the galactose derived C-glycoside 138 to protected CAs and diols

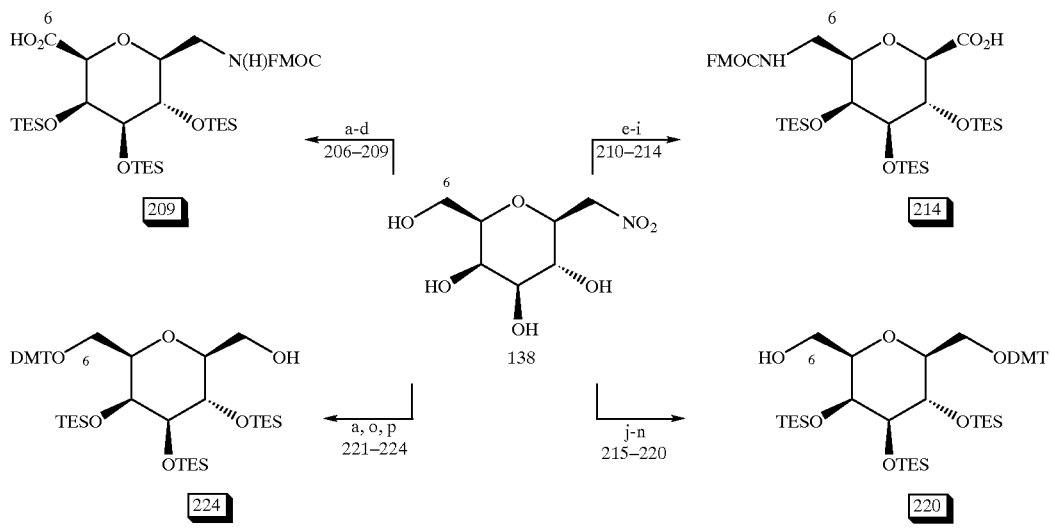

Reagents and conditions:
(a) (1) 1.1 equiv DMTCl, DMAP, Py, 12h, 20° C.;
   (2) TesOTf, CH$_2$Cl$_2$, 0° C., 1h, 83%.
(b) (1) LAH, ether, reflux, 2h;
   (2) FMOC-Cl, K$_2$CO$_3$, THF, H$_2$O, 0° C., 1h, 55%.
(c) 10% HCOOH in CH$_2$Cl$_2$, 0° C., 2 min, 100%.
(d) RuCl$_3$, NaIO$_4$, CH$_3$CN, H$_2$O, CCl$_4$, 20° C., 10 min, 54%.
(e) (1) 1 equiv TsCl, base;
   (2) TESOTf.
(f) NaN$_3$.
(g) oxidative Nef.
(h) Pd-C, H$_2$.
(i) FMOC-Cl, base.
(j) (1) 1 equiv PivCl, base;
   (2) TESOTf.
(k) (1) oxidate Nef;
   (2) CH$_2$N$_2$.
(l) DIBAL-H.
(m) DMTCl, DMAP, Py.
(n) LAH.
(o) Nef reaction.
(p) LAH An exemplary protocol for synthesizing a hexamer carbopeptoid (CPD 234) starting from galactose derived CA 214, glucosamine derived CA 62, and glucose derived CA, using standard methods for solid phase peptide synthesis is illustrated in Scheme 24. The reagents and condition for these reactions are as follows:
Step 1: DCC, HOBT, Et$_3$, DMF;
Step 2: Piperidine, DMF

Scheme 24a
Synthesis of a CPF (exemplified on a hexamer) using standard methods for solid phase peptide synthesis

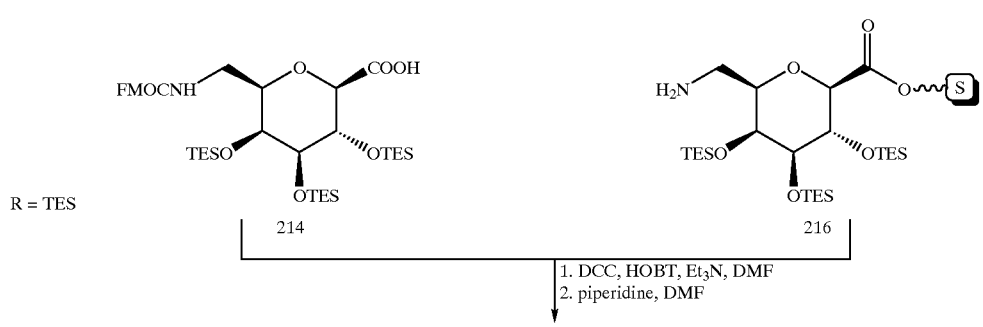

-continued
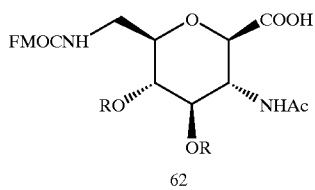
62
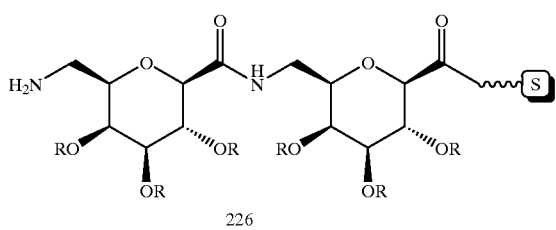
226
1. DCC, HOBT, Et₃N, DMF
2. piperidine, DMF
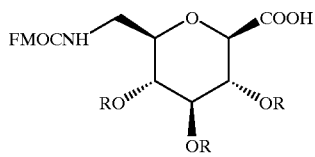
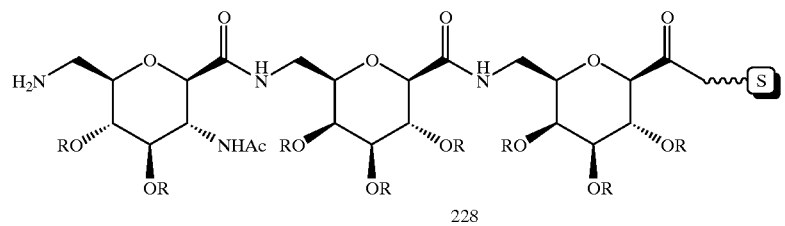
228
Scheme 24b
Synthesis of a CPF (exemplified on a hexamer) using standard methods for solid phase peptide synthesis
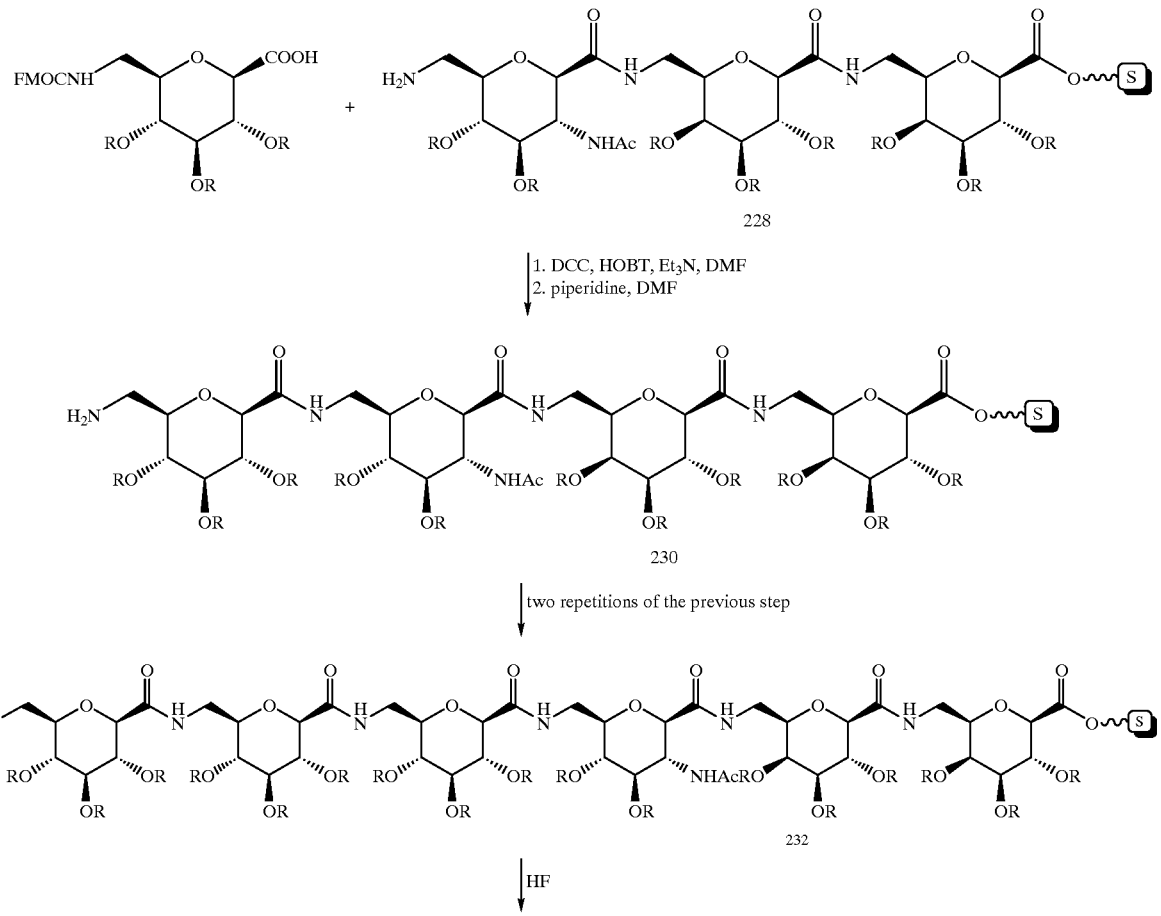

-continued

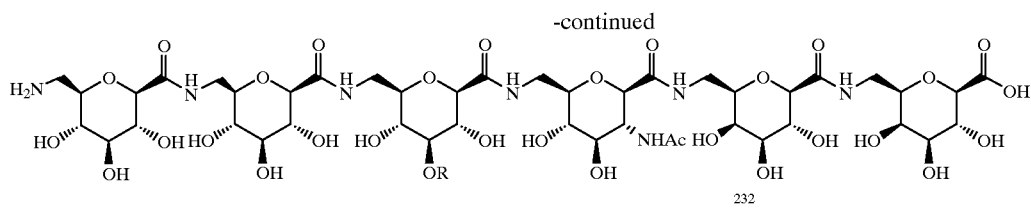

232

SYNTHETIC METHODS

Preparation of 37

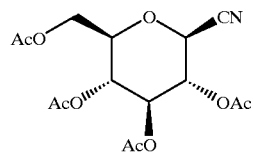

To a solution of β-D-Glucose pentaacetate 36 in nitromethane from Aldrich company (0.13 Molar), is added trimethylsilyl cyanide (3.0 equivalents) and then $SnCl_4$ (0.02 equivalents). The mixture is stirred for one hour and then an aqueous solution of sodium acetate was added to hydrolyze the remaining trimethylsilyl cyanide. The mixture is evaporated and the remaining oil is resuspended in dichloromethane and washed with sodium acetate solution (1x), water (1x), brine (1x) and then dried over magnesium sulphate and concentrated. The crude solid is then recrystallized from methanol to yield 37 as a white solid (47%). scheme 3 step 1; scheme 9, step a.

Preparation of 38

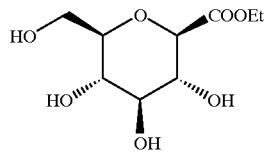

The crude product 37 is next dissolved in ethanol (0.15 M) and then concentrated $H_2SO_4$ (0.01 equivalents-catalytic) is added. The reaction mixture is heated to 85° C. for eight hours. The solution is next concentrated in vacuo and purification by flash column chromatography affords compound 38. scheme 3 step 2

Preparation of 39

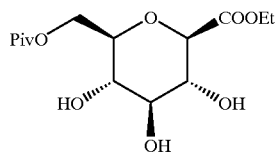

To a solution of 38 (1.0 equivalents) in pyridine (0.10 Molar), is added trimethylacetyl chloride (pivaloyl chloride) (2.5 equivalents) at 0° C. The reaction is stirred for 2 hours and then diluted with diethylether and washed with ammonium chloride (2x), copper sulfate (2x), brine (1x), dried over $MgSO_4$ and concentrated. Purification by flash column chromatography affords compound 39. scheme 3 step 1

Preparation of 40

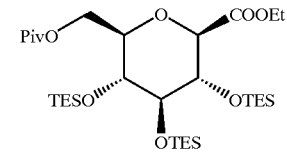

To a solution of 39 (1.0 equivalents) in methylene chloride (0.10 Molar), is added diisopropylethylamine (3.3 equivalents) at 0° C. Subsequent addition of triethylsilyl trifluoromethanesulfonate (3.3 equivalents) is followed by stirring for 2 hours and then the reaction is diluted with diethylether and washed with ammonium chloride (2x), brine (1x) and then dried ($MgSO_4$) and concentrated. Purification by flash column chromatography affords compound 40. scheme 3 step 2

Preparation of 41

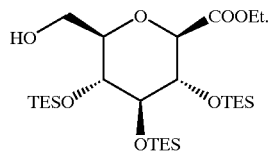

To a solution of 40 in ethanol (0.13 Molar), is added sodium ethoxide (0.3 equivalents) and the reaction mixture is stirred for two hours at room temperature. The solution is then concentrated in vacuo and purification by flash column to chromatography affords compound 41. scheme 3 step 1

Preparation of 42

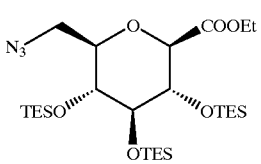

A solution of 41 (1.0 equivalents) in tetrahydrofuran (0.18 M) is treated with DPPA (diphenylphosphorylazide, 2.0 equivalents), triphenylphosphine (1.3 equivalents) and DIAD (diisopropyl-azo-dicarboxylate, 1.3 equivalents). The reaction is heated to 80° C. for 3 hours and then diluted with ether (2x) and washed with 0.5 M aqueous NaOH (2x). The organic layer is dried over $MgSO_4$ and evaporated. Purification by flash column chromatography affords compound 42. scheme 3 step 2

Preparation of 44

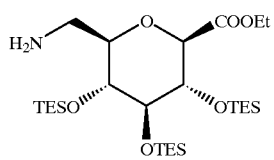
44

A solution of 42 (1.0 equivalents) is dissolved in ethanol (0.01 M total) at 25° C. The mixture is next exposed to 10% Pd/C (0.1 equivalents) and is then subsequently capped with a hydrogen balloon at 1 atmosphere. The reaction is stirred for 72 hours and is then filtered through celite. The crude mixture is subsequently diluted with ether and washed with NaHCO$_3$ (3×), brine (1×) and dried (MgSO$_4$) and concentrated. Purification by flash column chromatography affords compound 44. scheme 3 step 1

Preparation of 45

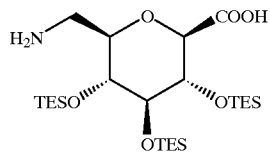
45

A solution of 44 (1.0 equivalents) is dissolved in p-dioxanes (0.1 M) and then exposed to a solution 3.0 Molar solution of sodium hydroxide (1.5 equivalents). The reaction is then stirred for 2 hours at 50° C. and is subsequently diluted with ether and washed with a solution of NH$_4$Cl (3×), brine (1×) and dried (MgSO$_{44}$) and concentrated. Purification by flash column chromatography affords compound 45. scheme 3 step 1

Preparation of 46

To a solution of 45 (1.0 equivalents) in methylene chloride (0.10 Molar), is added sodium bicarbonate (2.0 equivalents) at 0° C. Subsequent addition of 9-fluorenylmethyl chloroformate (FMOC-Cl, 1.2 equivalents) is followed by stirring for 2 hours and then the reaction is diluted with diethylether and washed with ammonium chloride (2×), brine (1×) and then dried (MgSO$_4$) and concentrated. Purification by flash column chromatography affords compound 46. scheme 3 step 2

Preparation of 48

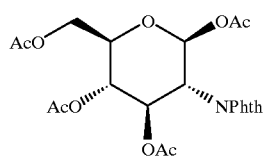

Procedure as described in Methods in Carbohydrate chemistry, Whistler, R., II, 1963, p. 327. A mixture of 80 g anhydrous D-glucosamine hydrochloride or D-galactosamine hydrochloride from Aldrich chemical company, in 200 mL. methanol and 20 g Dowex 50 (H+) acidic resin, is stirred at the boiling point in a round bottom flask. After 24-hr. reaction time, the resin is removed by filtration and ished three times with 20 ml. of methanol. The filrate and ishings are combined and concentrated to about 125 ml by rotovap. The concentrate is allowed to cool to room temperature and the product crystallizes overnight.

To a solution of free amine, in chloroform (0.5 M), is added phthalic anhydride (1.5 equiv.) and the reaction mixture is allowed to reflux at 70° C. for 4 h. The product is then crystallized and carried onto the next step.

To a solution of triol in methylene chloride (0.5 M), is added acetic anhydride (3.5 equiv.) and triethyl amine (3.5 equiv.) and the reaction mixture is allowed to stir at 0° C. for 4 h. The product 48, is then crystallized or purified by flash column chromatography and carried onto the next step.

Preparation of 50

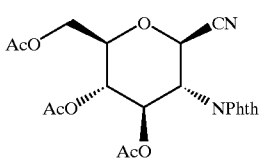
50

To a solution of N-phthalamido-D-Glucosamine tetraacetae 48 in nitromethane (0.13 Molar), is added trimethylsilyl cyanide (3.0 equivalents) and then SnCl$_4$ (0.02 equivalents). The mixture is stirred for one hour and then an aqueous solution of sodium acetate was added to hydrolyze the remaining trimethylsilyl cyanide. The mixture is evaporated and the remaining oil is resuspended in dichloromethane and washed with sodium acetate solution (1×), water (1×), brine (1×) and then dried over magnesium sulphate and concentrated. The crude solid is then recrystallized from methanol to yield 50 as a white solid (47%). scheme 4

Preparation of 52

The crude product 50 is next dissolved in ethanol (0.15 M) and then concentrated H$_2$SO$_4$ (0.01 equivalents-catalytic) is added. The reaction mixture is heated to 85° C. for eight hours. The solution is next concentrated in vacuo and purification by flash column chromatography affords compound 52. scheme 4

Preparation of 54

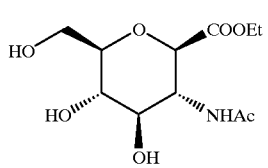
54

A solution of 52 (1.0 equivalents) is dissolved in methanol (0.1 M total). The reaction is then charged with acetic anhydride (1.1 equivalents) and is subsequently stirred for 2 hours at 30° C. The reaction is next diluted with ether and washed with NaHCO$_3$ (3×), brine (1×) and dried (MgSO$_4$) and concentrated. Purification by flash column chromatography affords compound 54. scheme 4

Preparation of 55

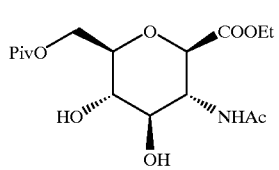
55

To a solution of 54 (1.0 equivalents) in pyridine (0.10 Molar), is added trimethylacetylchloride (pivaloyl chloride) (2.5 equivalents) at 0° C. The stirred is stirred for 2 hours Preparation of 56

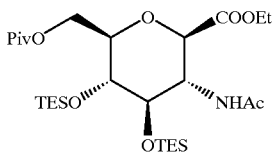

To a solution of 55 (1.0 equivalents) in methylene chloride (0.10 Molar), is added diisopropylethylamine (2.2 equivalents) at 0° C. Subsequent addition of triethylsilyl trifluoromethanesulfonate (2.2 equivalents) is followed by stirring for 2 hours and then the reaction is diluted with diethylether and washed with ammonium chloride (2×), brine (1×) and then dried (MgSO$_4$) and concentrated. Purification by flash column chromatography affords compound 56. scheme 4

Preparation of 57

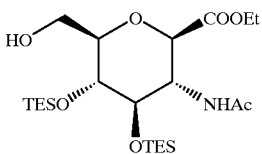

To a solution of 56 in ethanol (0.13 Molar), is added sodium ethoxide (0.3 equivalents) and the reaction mixture is stirred for two hours at room temperature. The solution is then concentrated in vacuo and purification by flash column chromatography affords compound 57. scheme 4

Preparation of 58

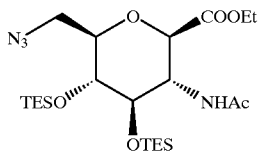

A solution of 57 (1.0 equivalents) in tetrahydrofuran (0.18 M) is treated with DPPA (diphenylphosphorylazide, 2.0 equivalents), triphenylphosphine (1.3 equivalents) and DIAD (diisopropyl-azo-dicarboxylate, 1.3 equivalents). The reaction is heated to 80° C. for 3 hours and then diluted with ether (2×) and washed with 0.5 M aqueous NaOH (2×). The organic layer is dried over MgSO$_4$ and evaporated. Purification by flash column chromatography affords compound 58. scheme 4

Preparation of 60

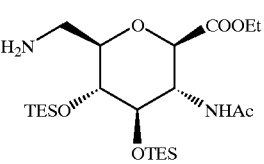

A solution of 58 (1.0 equivalents) is dissolved in ethanol (0.01 M total) at 25° C. The mixture is next exposed to 10% Pd/C (0.1 equivalents) and is then subsequently capped with a hydrogen balloon at 1 atm. The reaction is stirred for 72 hours and is then filtered through celite. The crude mixture is subsequently diluted with ether and washed with NaHCO$_3$ (3×), brine (1×) and dried (MgSO$_4$) and concentrated. Purification by flash column chromatography affords compound 60. scheme 4

Preparation of 61

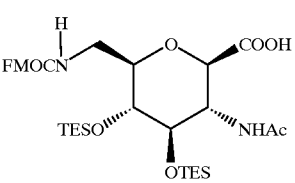

A solution of 60 (1.0 equivalents) is dissolved in p-dioxanes (0.1 M) and then exposed to a solution 3.0 Molar solution of sodium hydroxide (1.5 equivalents). The reaction is then stirred for 2 hours at 50° C. and is subsequently diluted with ether and washed with a solution of NH$_4$Cl (3×), brine (1×) and dried (MgSO$_4$) and concentrated. Purification by flash column chromatography affords compound 61. scheme 4

Preparation of 62

To a solution of 61 (1.0 equivalents) in methylene chloride (0.1 O Molar), is added sodium bicarbonate (2.0 equivalents) at 0° C.

Subsequent addition of 9-fluorenylmethyl chloroformate (FMOC-Cl, 1.2 equivalents) is followed by stirring for 2 hours and then the reaction is diluted with diethylether and washed with ammonium chloride (2×), brine (1×) and then dried (MgSO$_4$) and concentrated. Purification by flash column chromatography affords compound 62. scheme 4

Preparation of 63

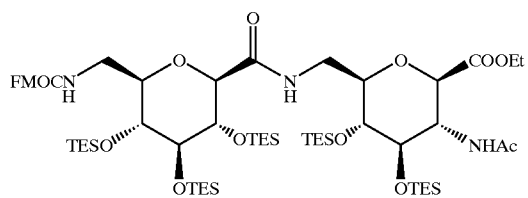

To a stirred solution of the acid 46 (1.0 equivalents) and the amine 60 (1.1 equivalents) in dimethylformamide (0.10 Molar) at 25° C. is added 1-hydroxybenzotriazole (HOBT; 1.1 equivalents). Next dicyclohexylcarbodiimide (1.2 equivalents) is added and the reaction is stirred for 14 hours. The mixture is diluted with ether, filtered and the filtrate is washed with aqueous NaHCO$_3$ (2×), water (2×), and brine (2×). The organic phase is dried over MgSO$_4$ and then concentrated. Purification by flash column chromatography affords compound 63. scheme 5 step 1

Preparation of 64

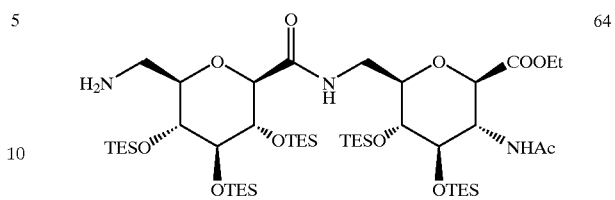

To a stirred solution of 63 (1.0 equivalents) in dimethylformamide (0.10 Molar) at 25° C., is added piperidine (1.1 equivalents). The reaction is stirred for 1 hour and is then diluted with ether, and washed with aqueous CuSO$_4$ (2×), water (2×), and brine (2×). The organic phase is dried over MgSO$_4$ and then concentrated. Purification by flash column chromatography affords compound 64. scheme 5 step 2

Preparation of 65

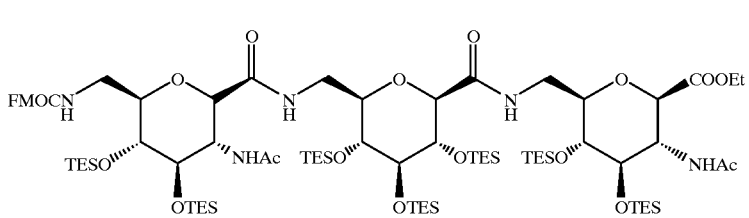

To a stirred solution of the acid 62 (1.0 equivalents) and the amine 64 (1.1 equivalents) in dimethylformamide (0.10 Molar) at 25° C., is added 1-hydroxybenzotriazole (HOBT; 1.1 equivalents). Note: numerous iterations can be performed using the acid 62 or intermixing with other acids including for example acid 46 to form successive oligomers where n=2 to infinity (a hexamer is shown in scheme 5) to obtain large carbopeptoid libraries. Next dicyclohexylcarbodiimide (1.2 equivalents) is added and the reaction is stirred for 14 hours. The mixture is diluted with ether, filtered and the filtrate is washed with aqueous NaHCO$_3$ (2×), water (2×), and brine (2×). The organic phase is dried over MgSO$_4$ and then concentrated. Purification by flash column chromatography affords compound 65. scheme 5 step 1

Preparation of 66

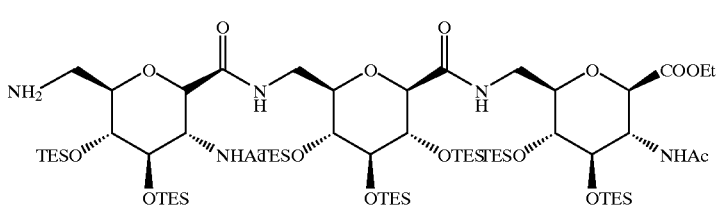

To a stirred solution of 65 (1.0 equivalents) in dimethylformamide (0.10 Molar) at 25° C., is added piperidine (1.1 equivalents). The reaction is stirred for 1 hour and is then diluted with ether, and washed with aqueous CuSO$_4$ (2×), water (2×), and brine (2×). The organic phase is dried over MgSO$_4$ and then concentrated. Purification by flash column chromatography affords compound 66. Note: numerous iterations can be performed using variable length oligomers of 66 to form peptoid oligomers where n=2 to infinity (a hexamer is shown in scheme 5). scheme 5 step 2

Preparation of 67

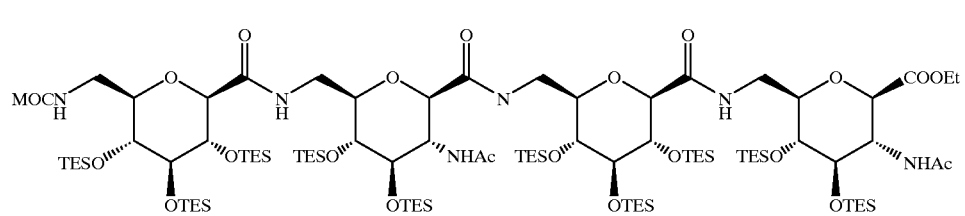

67

To a stirred solution of the acid 46 (1.0 equivalents) and the amine 66 (1.1 equivalents) in dimethylformamide (0.10 Molar) at 25° C., is added 1-hydroxybenzotriazole (HOBT; 1.1 equivalents). Note: numerous iteration can be performed using the acid 46 or intermixing with other acids including for example acid 62, to form successive oligomers where n=2 to infinity (a hexamer is shown in scheme 5) to obtain large carbopeptoid libraries. Next dicyclohexylcarbodiimide (1.2 equivalents) is added and the reaction is stirred for 14 hours. The mixture is diluted with ether, filtered and the filtrate is washed with aqueous $NaHCO_3$ (2×), water (2×), and brine (2×). The organic phase is dried over $MgSO_4$ and then concentrated. Purification by flash column chromatography affords compound 67. scheme 5 step 1

Preparation of 68

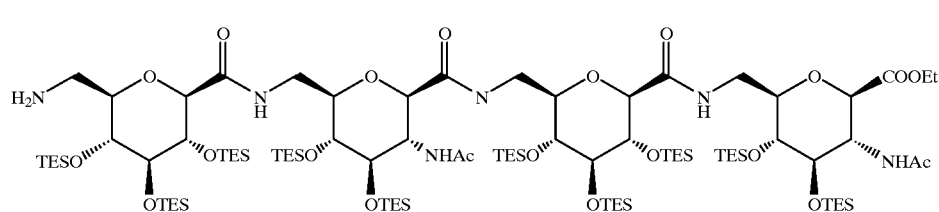

68

To a stirred solution of 67 (1.0 equivalents) in dimethylformamide (0.10 Molar) at 25° C., is added piperidine (1.1 equivalents). The reaction is stirred for 1 hour and is then diluted with ether, and washed with aqueous $CuSO_4$ (2×), water (2×), and brine (2×). The organic phase is dried over $MgSO_4$ and then concentrated. Purification by flash column chromatography affords compound 68. Note: numerous iterations can be performed using variable length oligomers of 68 to form peptoid oligomers where n=2 to infinity (a hexamer is shown in scheme 5). scheme 5 step 2

Preparation of 69

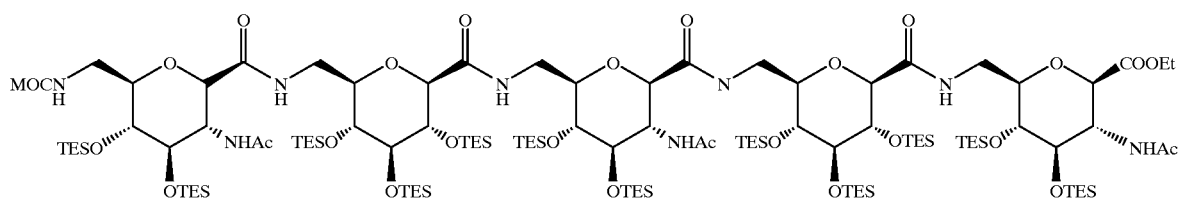

69

To a stirred solution of the acid 62 (1.0 equivalents) and the amine 68 (1.1 equivalents) in dimethylformamide (0.10 Molar) at 25° C., is added 1-hydroxybenzotriazole (HOBT; 1.1 equivalents). Note: numerous iterations can be performed using the acid 62, or intermixing with other acids including for example acid 46, to form successive oligomers where n=2 to infinity (a hexamer is shown in scheme 5) to obtain large carbopeptoid libraries. Next dicyclohexylcarbodiimide (1.2 equivalents) is added and the reaction is stirred for 14 hours. The mixture is diluted with ether, filtered and the filtrate is washed with aqueous NaHCO₃ (2×), water (2×), and brine (2×). The organic phase is dried over MgSO₄ and then concentrated. Purification by flash column chromatography affords compound 69. scheme 5 step 1

Preparation of 70

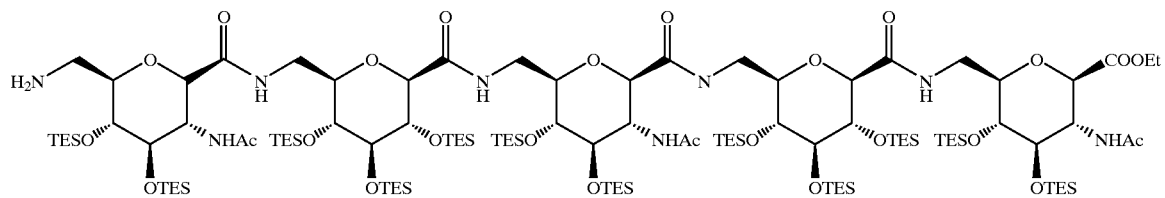

To a stirred solution of 69 (1.0 equivalents) in dimethylformamide (0.10 Molar) at 25° C., is added piperidine (1.1 equivalents). The reaction is stirred for 1 hour and is then diluted with ether, and washed with aqueous CuSO₄ (2×), water (2×), and brine (2×). The organic phase is dried over MgSO₄ and then concentrated. Purification by flash column chromatography affords compound 70. Note: numerous iterations can be performed using variable length oligomers of 70 to form peptoid oligomers where n=2 to infinity (a hexamer is shown in scheme 5). scheme 5 step 2

Preparation of 71

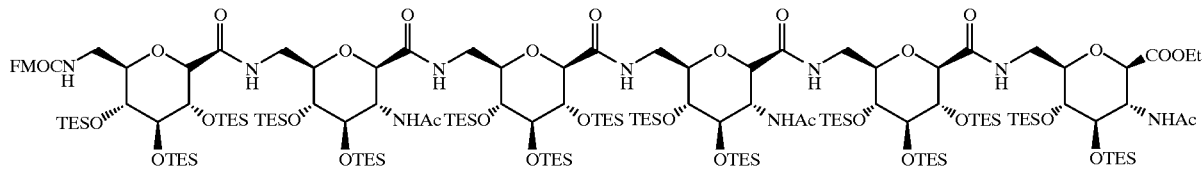

To a stirred solution of the acid 46 (1.0 equivalents) and the amine 70 (1.1 equivalents) in dimethylformamide (0.10 Molar) at 25° C., is added 1-hydroxybenzotriazole (HOBT; 1.1 equivalents). Note: numerous iterations can be performed using the acid 46 or intermixing with other acids including for example acid 62, to form successive oligomers where n=2 to infinity (a hexamer is shown in scheme 5) to obtain large carbopeptoid libraries. Next dicyclohexylcarbodiimide (1.2 equivalents) is added and the reaction is stirred for 14 hours. The mixture is diluted with ether, filtered and the filtrate is washed with aqueous NaHCO₃ (2×), water (2×), and brine (2×). The organic phase is dried over MgSO₄ and then concentrated. Purification by flash column chromatography affords compound 71. scheme 5 step 1

Preparation of 72

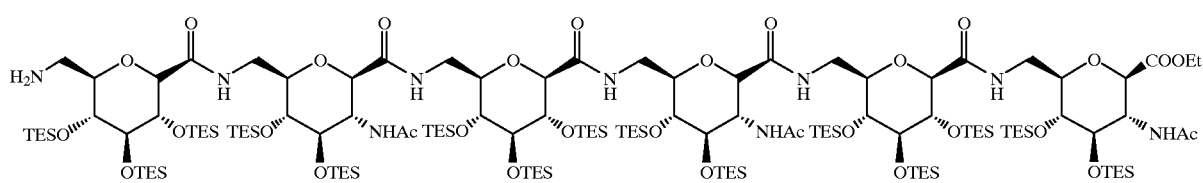

To a stirred solution of 71 (1.0 equivalents) in dimethylformamide (0.10 Molar) at 25° C., is added piperidine (1.1 equivalents). The reaction is stirred for 1 hour and is then diluted with ether, and washed with aqueous CuSO$_4$ (2×), water (2×), and brine (2×). The organic phase is dried over MgSO$_4$ and then concentrated. Purification by flash column chromatography affords compound 72. Note: numerous iterations can be performed using variable length oligomers of 72 to form peptoid oligomers where n=2 to infinity (a hexamer is shown in scheme 5). scheme 5 step 2

Preparation of 74

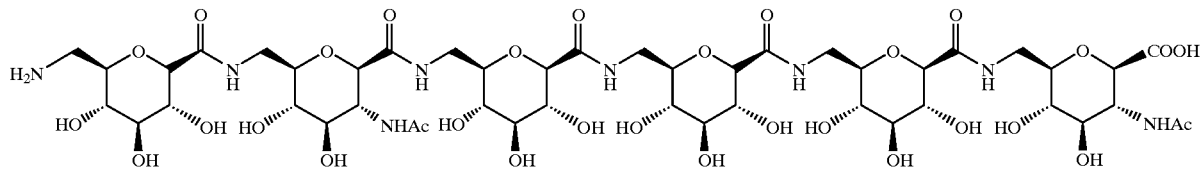

To a stirred solution of 72 (1.0 equivalents) in acetonitrile (0.50 Molar) is added an HF pyridine solution (0.50 M) from Aldrich chemical company. The reaction is allowed to stir for five hours and is then condensed. The crude 73 oligomer is then resuspended in p-dioxane (0.50 Molar) to which is added a 3.0 Molar solution of NaOH (3.0 equivalents). The reaction is stirred for 1 hour at 50° C. and is then quenched with aqueous NH$_4$Cl (2×) and subsequently lyophilized. Purification by HPLC chromatography affords compound 74. scheme 5

Preparation of 76

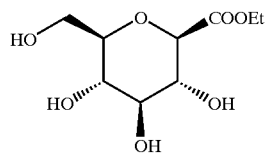

To a solution of β-D-Glucose pentaacetate 36 in nitromethane from Aldrich company (0.13 Molar), is added trimethylsilylcyanide (3.0 equivalents) and then tin tetrachloride (0.02 equivalents). Note: other pyranose sugars such as β-P-Mannose, β-D-Galactose pentaacetate and other lewis acids such as BF$_3$OEt$_2$ may be used for alternative derivatives. The mixture is stirred for one hour and then an aqueous solution of sodium acetate was added to hydrolyze the remaining trimethylsilylcyanide. The mixture is evaporated and the remaining oil is resuspended in dichloromethane and washed with sodium acetate solution (1×), water (1×), brine (1×) and then dried over magnesium sulphate and concentrated. The crude product is next dissolved in ethanol (or methanol if the O-methyl glycoside is desired as in scheme 20), (0.15 M) and then concentrated H$_2$SO$_4$ (0.01 equivalents) is added. The reaction mixture is heated to 85° C. for eight hours. The solution is next concentrated in vacuo and purification by flash column chromatography affords compound 76. scheme 6; 76, scheme 20 (as the O-methyl glycoside).

Preparation of 78

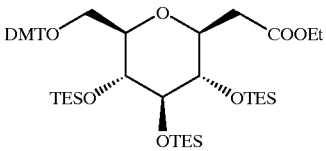

To Tetrol 76 (1.0 equivalents) in pyridine (0.10 Molar), is added dimethyoxytritylchloride (DMT chloride) (2.5 equivalents) at 0°°C. The reaction is stirred for 2 hours and then diluted with diethylether and washed with ammonium chloride (2×), copper sulfate (2×), brine (1×), dried over MgSO$_4$ and concentrated. Next a solution of the crude intermediate (1.0 equivalents) is dissolved in methylene chloride (0.10 Molar) and diisopropylethylamine (4.4 equivalents) is added at 0° C. Subsequent addition of triethylsilyl trifluoromethanesulfonate (4.4 equivalents) is followed by stirring for 2 hours and then the reaction is diluted with diethylether and washed with ammonium chloride (2×), brine (1×) and then dried (MgSO$_4$) and concentrated. Purification by flash column chromatography affords compound 78, scheme 6; 78, scheme 20 (as the O-methyl glycoside).

Preparation of 80

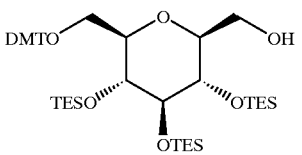

To a solution of 78 (1.0 equivalents) in methylene chloride (0.10 Molar) is added a 1.0 M solution of DIBALH in methylene chloride from Aldrich chemical company (1.2 equivalents) at 0° C. Subsequent stirring for 2 hours is followed by dilution with diethylether and washing with sodium-potassium tartrate (2×), brine (1×) and then MgSO$_4$. The solution is then concentrated and purification by flash column chromatography affords compound 80. scheme 6

Preparation of 82

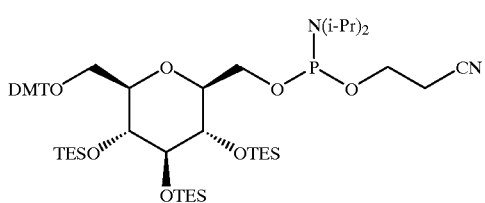

To a solution of 80 (1.0 equivalents) in methylene chloride (0.10 M), is added diisopropylethylamine (4.0 equivalents) at 25° C. The reaction is stirred for 5 minutes and then 2-cyanoethyl-N,N-diisopropyl-chlorophosphoramidite (1.5 equivalents) is added, as prepared from the procedures of Sinha et al. *Nucl. Acids Res.* 1984, 12, 4539. After 15 minutes the reaction is complete and is next diluted with ether and next washed with brine (1×) and is then dried (MgSO$_4$) and concentrated. Purification by flash column chromatography (silica, 30% ethyl acetate in petroleum ether) affords compound 82 (66% yield). scheme 6

Preparation of 84

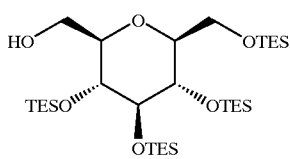

To 80 (1.0 equivalents) in methylene chloride (0.10 Molar) at 0° C., is added diisopropylethylamine (1.1 equivalents). Subsequent addition of triethylsilyl trifluoromethanesulfonate (1.1 equivalents) is followed by stirring for 2 hours and then the reaction is diluted with diethylether and washed with ammonium chloride (2×), brine (1×) and then dried (MgSO$_4$) and concentrated. The crude is then resuspended in nitromethane and exposed to 10% Cl$_3$COOH (1.1 equivalents) in THF (0.10 Molar). The reaction is stirred at 0° C. for 2 hours and is then diluted with ether and washed with sodium bicarbonate (2×), brine (1×) and then dried (MgSO$_4$) and concentrated. Purification by flash column chromatography affords compound 84. scheme 6

Preparation of 86

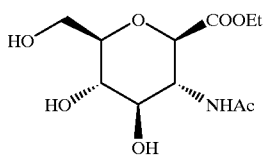

To a solution of N-phthalamido-D-Glucosamine tetraacetate 48 in nitromethane (0.13 Molar), is added trimethylsilyl cyanide (3.0 equivalents) and then SnCl$_4$(0.02 equivalents). The mixture is stirred for one hour and then an aqueous solution of sodium acetate was added to hydrolyze the remaining trimethylsilyl cyanide. The mixture is evaporated and the remaining oil is resuspended in dichloromethane and washed with sodium acetate solution (1×) water (1×), brine (1×) and then dried over magnesium sulphate and concentrated. The crude product is next dissolved in ethanol (0.15 M) and then concentrated H$_2$SO$_4$ (0.04 equivalents) is added. The reaction mixture is heated to 85° C. for eight hours. The solution is next concentrated in vacuo and is then resuspended in methanol (0.10 M) and acetic anhydride (1.1 equivalents) from Aldrich company is added in one step. After 2 hours, condensation and purification by flash column chromatography affords compound 86. scheme 7

Preparation of 88

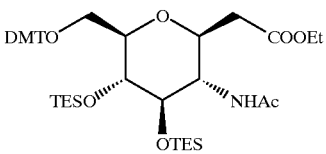

To Triol 86 (1.0 equivalents) in pyridine (0.10 Molar), is added dimethyoxytritylchloride (DMT chloride) (2.5 equivalents) at 0° C. The reaction is stirred for 2 hours and then diluted with diethylether and washed with ammonium chloride (2×), copper sulfate (2×), brine (1×), dried over MgSO$_4$ and concentrated. Next a solution of the crude intermediate (1.0 equivalents) is dissolved in methylene chloride (0.10 Molar) and diisopropylethylamine (3.3 equivalents) is added at 0° C. Subsequent addition of triethylsilyl trifluoromethanesulfonate (3.3 equivalents) is followed by stirring for 2 hours and then the reaction is diluted with diethylether and washed with ammonium chloride (2×), brine (1×) and then dried (MgSO$_4$) and concentrated. Purification by flash column chromatography affords compound 88. scheme 7

Preparation of 90

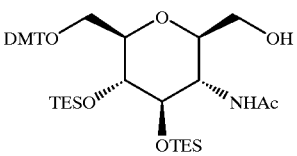

To a solution of 88 (1.0 equivalents) in methylene chloride (0.10 Molar) is added a 1.0 M solution of DIBALH in methylene chloride from Aldrich chemical company (1.2 equivalents) at 0° C. Subsequent stirring for 2 hours is followed by dilution with diethylether and washing with sodium-potassium tartrate (2×), brine (1×) and then MgSO$_4$. The solution is then concentrated and purification by flash column chromatography affords compound 90. scheme 7

Preparation of 92

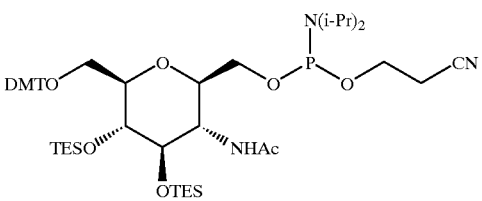

To a solution of 90 (1.0 equivalents) in methylene chloride (0.10 M) is added diisopropylethylamine (4.0 equivalents) at 25° C. The reaction is stirred for 5 minutes and then 2-cyanoethyl-N,N-diisopropylchlorophosphoramidite (1.5 equivalents) is added, as prepare from the procedures of Sinha et al. *Nucl. Acids Res.* 1984, 12, 4539. After 15 minutes the reaction is complete and is next diluted with ether and next washed with brine (1×) and is then dried (MgSO$_4$) and concentrated. Purification by flash column chromatography (silica, 30% ethyl acetate in petroleum ether) affords compound 92 (66% yield). scheme 7
Preparation of 94

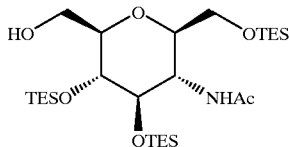

94

To 90 (1.0 equivalents) in methylene chloride (0.10 Molar) at 0° C., is added diisopropylethylamine (1.1 equivalents). Subsequent addition of triethylsilyl trifluoromethanesulfonate (1.1 equivalents) is followed by stirring for 2 hours and then the reaction is diluted with diethylether and washed with ammonium chloride (2×), brine (1×) and then dried (MgSO$_4$) and concentrated. The crude is then resuspended in nitromethane and exposed to 10% Cl$_3$COOH (1.1 equivalents) in THF (0.10 Molar). The reaction is stirred at 0° C. for 2 hours and is then diluted with ether and washed with sodium bicarbonate (2×), brine (1×) and then dried (MgSO$_4$) and concentrated. Purification by flash column chromatography affords compound 94. scheme 7
Preparation of 98 (Homodimer Scheme 8)

To a solution of 94 (1.0 equivalents) in methylene chloride (0.10 M), is added 1-H-tetrazole from Aldrich company (10.0 equivalents) at 25° C. Next, a solution of 82 (3.0 equivalents) in methylene chloride (1.0 M), is added dropwise with stirring at 25° C. After 25 minutes, the mixture is cooled to 0° C. and I$_2$ (4.0 equivalents), 2,6 lutidine (4.0 equivalents) in THF (1.0 M) is added to oxidize the phosphoamidate to the phosphate (Alternatively m-chloroperoxybenzoic acid (4.5 equivalents) is added). The reaction is next stirred for an additional 5 minutes and is next diluted with ether and washed with brine (1×) and dried (MgSO$_4$) and concentrated. Purification by flash column chromatography and then the product is suspended in acetic acid-tetrahydrofuran-water (3:1:1), (0.01 M) and stirred for 18 hours at 25° C. The reaction is then diluted with ether and washed with NaHCO$_3$ (3×), brine (1×) and dried (MgSO$_4$) and concentrated. Purification by flash column chromatography affords compound 98 (scheme 8).
Preparation of 102 (Heterotrimer Scheme 8)

To a solution of 98 (1.0 equivalents) in methylene chloride (0.10 M), is added 1-H-tetrazole from Aldrich company (10.0 equivalents) at 25° C. Next, a solution of 92 (3.0 equivalents) in methylene chloride (1.0 M), is added dropwise with stirring at 25° C. After 25 minutes, the mixture is cooled to 0° C. and I$_2$ (4.0 equivalents), 2,6 lutidine (4.0 equivalents) in THF (1.0 M) is added to oxidize the phosphoamidate to the phosphate (Alternatively m-chloroperoxybenzoic acid (4.5 equivalents) is added). The reaction is next stirred for an additional 5 minutes and is next diluted with ether and washed with brine (1×) and dried (MgSO$_4$) and concentrated. Purification by flash column chromatography affords compound 102 (scheme 8).
Preparation of 106 (Heterotetramer Scheme 8)

To a solution of 102 (1.0 equivalents) in methylene chloride (0.10 M), is added 1-H-tetrazole from Aldrich company (10.0 equivalents) at 25° C. Next, a solution of 82 (3.0 equivalents) in methylene chloride (1.0 M), is added dropwise with stirring at 25° C. After 25 minutes, the mixture is cooled to 0° C. and I$_2$ (4.0 equivalents), 2,6 lutidine (4.0 equivalents) in THF (1.0 M) is added to oxidize the phosphoamidate to the phosphate (Alternatively m-chloroperoxybenzoic acid (4.5 equivalents) is added). The reaction is next stirred for an additional 5 minutes and is next diluted with ether and washed with brine (1×) and dried (MgSO$_4$) and concentrated. Purification by flash column chromatography and then the product is suspended in acetic acid-tetrahydrofuran-water (3:1:1), (0.01 M) and stirred for 18 hours at 25° C. The reaction is then diluted with ether and washed with NaHCO$_3$ (3×), brine (1×) and dried (MgSO$_4$) and concentrated. Purification by flash column chromatography affords compound 106 (scheme 8).
Preparation of 110 (Heteropentamer Scheme 8)

To a solution of 106 (1.0 equivalents) in methylene chloride (0.10 M), is added 1-H-tetrazole from Aldrich company (10.0 equivalents) at 25° C. Next, a solution of 92 (3.0 equivalents) in methylene chloride (1.0 M), is added dropwise with stirring at 25° C. After 25 minutes the mixture is cooled to 0° C. and I$_2$ (4.0 equivalents), 2,6 lutidine (4.0 equivalents) in THF (1.0 M) is added to oxidize the phosphoamidate to the phosphate (Alternatively m-chloroperoxybenzoic acid (4.5 equivalents) is added). The reaction is next stirred for an additional 5 minutes and is next diluted with ether and washed with brine (1×) and dried (MgSO$_4$) and concentrated. Purification by flash column chromatography and then the product is suspended in acetic acid-tetrahydrofuran-water (3:1:1), (0.01 M) and stirred for 18 hours at 25° C. The reaction is then diluted with ether and washed with NaHCO$_3$ (3×), brine (1×) and dried (MgSO$_4$) and concentrated. Purification by flash column chromatography affords compound 110 (scheme 8).
Preparation of 114 (Heterohexamer Scheme 8)

To a solution of 110 (1.0 equivalents) in methylene chloride (0.10 M), is added 1-H-tetrazole from Aldrich company (10.0 equivalents at 25° C. Next, a solution of 82 (3.0 equivalents) in methylene chloride (1.0 M), is added dropwise with stirring at 25° C. After 25 minutes, the mixture is cooled to 0° C. and I$_2$ (4.0 equivalents), 2,6 lutidine (4.0 equivalents) in THF (1.0 M) is added to oxidize the phosphoamidate to the phosphate (Alternatively m-chloroperoxybenzoic acid (4.5 equivalents) is added). The reaction is next stirred for an additional 5 minutes and is next diluted with ether and washed with brine (1×) and dried (MgSO$_4$) and concentrated. Purification by flash column chromatography and then the product is suspended in acetic acid-tetrahydrofuran-water (3:1:1), (0.01 M) and stirred for 18 hours at 25° C. The reaction is then diluted with ether and washed with NaHCO$_3$ (3×), brine (1×) and dried (MgSO$_4$) and concentrated. Purification by flash column chromatography affords compound 114 (scheme 8).
Preparation of 116 (Heterohexamer scheme 8)

To a solution of 114 (1.0 equivalents) in methylene chloride (0.10 M), is added a solution of HF-pyridine (1.0 M) at 0° C. The reaction is next stirred for an additional 30 minutes and is next diluted with ether and washed with a saturated solution of sodium bicarbonate (3×), copper sulfate solution to remove the pyridine (2×) brine (1×), dried (MgSO$_4$) and concentrated. Purification by flash column chromatography and then the product is resuspended in concentrated aqueous ammonium hydroxide and acetonitrile (1:1), (0.01 M total). The reaction is then stirred for 2 hours at 50° C. and is subsequently diluted with ether and washed with NaHCO$_3$ (3×), brine (1×) and dried (MgSO$_4$) and concentrated. Purification by flash column chromatography affords compound 116 scheme 8.

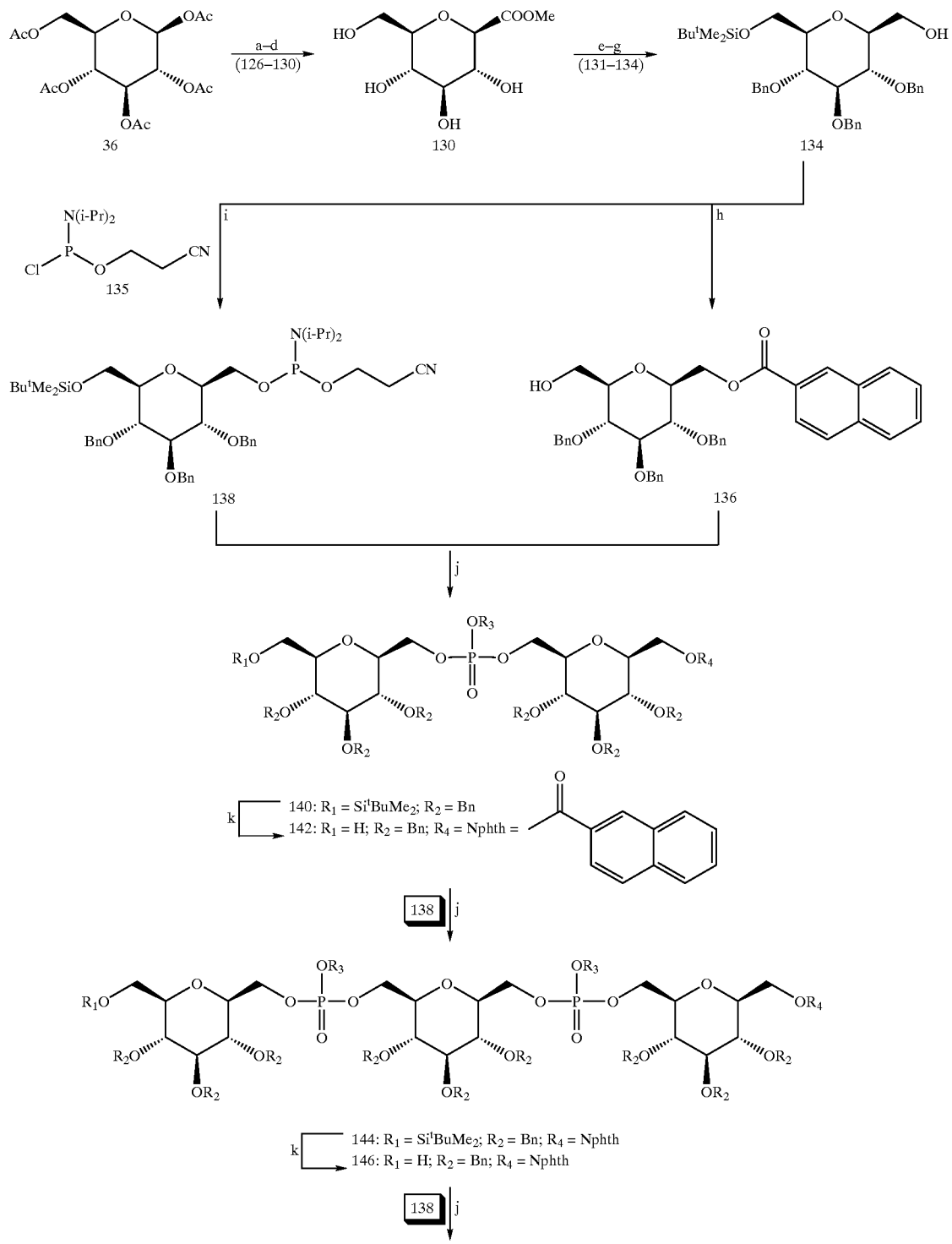

Scheme 9
Synthesis of a Carbonucleotoid

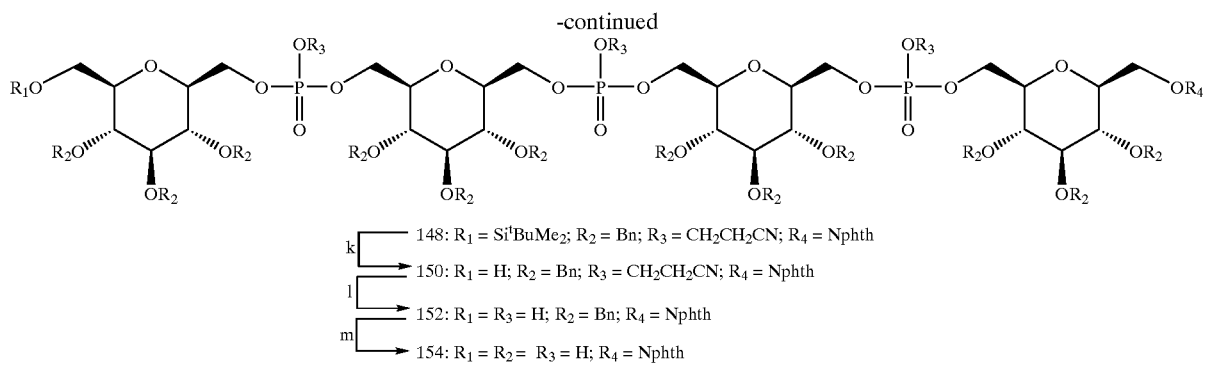

k ⤓ 148: $R_1$ = Si$^t$BuMe$_2$; $R_2$ = Bn; $R_3$ = CH$_2$CH$_2$CN; $R_4$ = Nphth
l ⤓ 150: $R_1$ = H; $R_2$ = Bn; $R_3$ = CH$_2$CH$_2$CN; $R_4$ = Nphth
   ⤓ 152: $R_1$ = $R_3$ = H; $R_2$ = Bn; $R_4$ = Nphth
m ⤓ 154: $R_1$ = $R_2$ = $R_3$ = H; $R_4$ = Nphth Preparation of 125

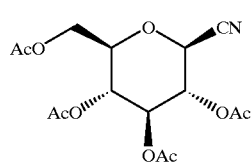

To a solution of β-D-Glucose pentaacetate in nitromethane from Aldrich company (0.13 Molar), is added trimethylsilylcyanide (3.0 equivalents) and then borontrifluoride etherate (0.02 equivalents). Note: other pyranose sugars such as β-D-Mannose, β-D-Galactose pentaacetate and other lewis acids such as SnCl$_4$, may be used for alternative derivatives. The mixture is stirred for one hour and then an aqueous solution of sodium acetate was added to hydrolyze the remaining trimethylsilylcyanide. The mixture is evaporated and the remaining oil is resuspended in dichloromethane and washed with sodium acetate solution (1×), water (1×), brine (1×) and then dried over magnesium sulphate and concentrated. The crude solid is then recrystallized from methanol to yield 125(also 37) as a white solid (47%). scheme 9 step a Preparation of 126

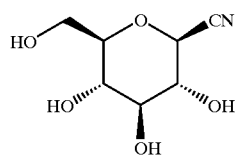

To a solution of 125 in methanol (0.13 Molar), is added sodium methoxide (0.3 equivalents) and the reaction mixture is stirred for two hours at room temperature. The dark brown solution is then concentrated in vacuo to give a dark brown syrup of compound 126 which is carried on without purification as a crude oil for the next step. scheme 9 step b Preparation of 127

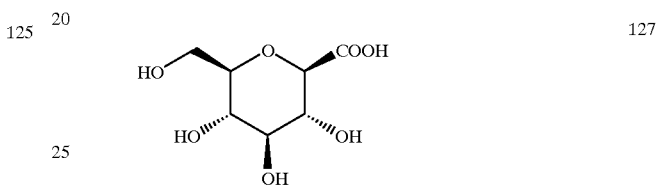

The crude product 126 is dissolved in 25% NaOH (0.5 M) and heated at reflux for 18 hours (vigorous reflux is necessary). Next, the solution is diluted with an addition of water (0.1 M) and to this solution is added Amberlite 112120 resin (H$^+$-form) and is then stirred. The supernatant is then decanted and the resin is washed until the eluate is colorless. The eluate is then collected, condensed and azeotroped with MeOH which yields 127 as a crude, pale yellow syrup (47%).

Preparation of 130

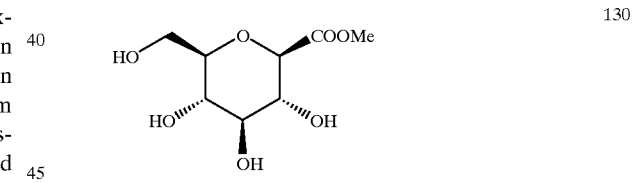

The crude product 127 is next dissolved in methanol (0.15 M) and then concentrated HCl (0.01 equivalents) is added. The reaction mixture is heated to 85° C. for eight hours. The solution is next concentrated in vacuo and purification by flash column chromatography (silica, 20% methanol in ethyl acetate), affords compound 130 as a white solid (60% yield). scheme 9 step d Preparation of 131

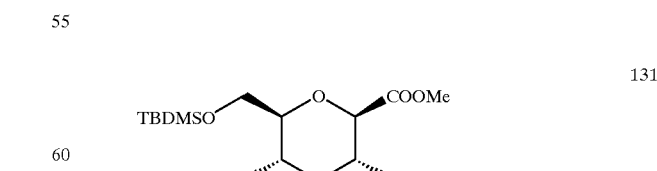

To a solution of 130 (1.0 equivalents) in dimethylformamide (0.23 Molar), is added imidazole (2.5 equivalents) at 0° C. Subsequent addition of tert-Butyl-dimethylsilyichloride (2.5 equivalents) is followed by stirring for 2 hours and then the reaction is diluted with diethylether and washed with ammonium chloride (2x), brine (1x) and then dried (MgSO$_4$) and concentrated. Purification by flash column chromatography (silica, 50% ethyl acetate) affords compound 131 as a white solid (93% yield). scheme 9 step e Note: the molecule can be protected with other primary directing protecting groups such as DMT (dimethoxytrityl), and TBDPS tert-butyldiphenlysilyl, etc.

Preparation of 132

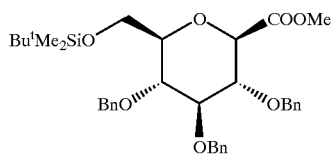

132

To a solution of 131 (1.0 equivalents) in dimethylformamide (0.23 M), is added Ag$_2$O (6.0 equivalents) at 25° C. Benzyl bromide (9.0 equivalents) is next added and the reaction is allowed to stir for 20 hours. The reaction is diluted with diethylether and washed with ammonium chloride (2x), brine (1x) and then dried (MgSO$_4$) and concentrated. Purification by flash column chromatography (silica, 20% ethyl acetate) affords compound 132 (83% yield). scheme 9 step f Note: the choice of the protecting group is relative and the molecule can be protected with other protecting groups at C2, C3, C4, such as PMB (paramethoxybenzyl), TES (triethylsilyl), TBS (tertbutyldimethylsilyl), etc.

Preparation of 134

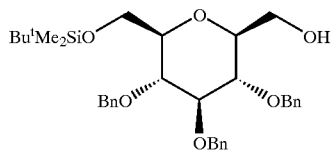

134

To a solution of 132 (1.0 equivalents) in tetrahydrofuran (0.08 M), is added diisobutylaluminumhydride (DIBALH) (3.0 equivalents) at 0° C. The reaction is stirred for 1 hour and then quenched with methanol and diluted with ether. The reaction is next worked-up with ammonium chloride (2x), brine (1x) and is then dried (MgSO$_4$) and concentrated. Purification by flash column chromatography (silica, 20% ethyl acetate) affords compound 134 (66% yield). scheme 9 step g Preparation of 136

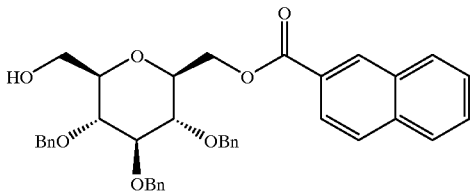

136

To a solution of 134 (1.0 equivalents) in pyridine (10.0 equivalents), is added naphthoyl chloride (3.0 equivalents) from Aldrich company (3.0 equivalents) at 25° C. The reaction is stirred for 45 minutes and then diluted with ether and worked-up with a saturated solution of CuSO$_4$ (2x), brine (1x) and is then dried (MgSO$_4$) and concentrated. The crude product is then exposed to acetic acid/tetrahydrofuran/water (3:1:1) at 25° C. and allowed to stir for 15 hours. The reaction is then diluted with ether and worked-up with brine (2x) and is then dried (MgSO$_4$) and concentrated. Purification by flash column chromatography (silica, 20% ethyl acetate) affords compound 136 (95% yield). Note: alternatively, one could originally protect the C7 position as a DMT (dimethoxytrityl) functionality and protect the C1 position as a TES (triethyl silyl) group. Subsequent mild acid hydrolysis of the DMT group leads to the above compound with the TES group at the C1 position and a free hydroxyl at the (C7 position. scheme 9 step h Preparation of 138

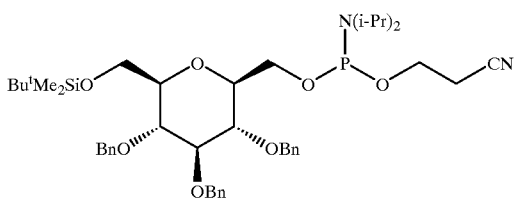

138

To a solution of 134 (1.0 equivalents) in methylene chloride (0.10 M), is added diisopropylethylamine (4.0 equivalents) at 25° C. The reaction is stirred for 5 minutes and then 2-cyanoethyl-N N-diisopropyl-chlorophosphoramidite (1.5 equivalents) is added, as prepared from the procedures of Sinha et al. *Nucl. Acids Res.* 1984, 12, 4539. After 15 minutes the reaction is complete and is next diluted with ether and next washed with brine (1x) and is then dried (MgSO$_4$) and concentrated. Purification by flash column chromatography (silica, 30% ethyl acetate in petroleum ether) affords compound 138 (66% yield). scheme 9 step i It should be noted that the oligomerization process as shown below in scheme 9, uses the same C-glycoside 138 in an iterative fashion. The process can be extended however to include a pool of random or ordered C-glycosides as depicted in scheme 8.

Preparation of 140

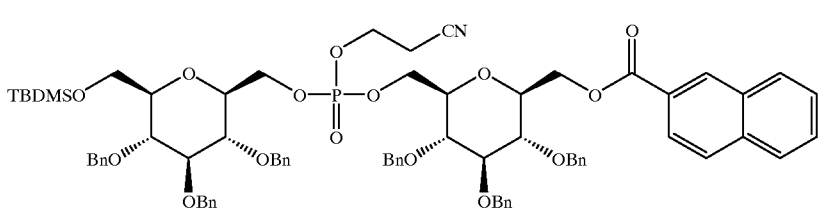

140

To a solution of 136 (1.0 equivalents) in methylene chloride (0.10 M), is added 1-H-tetrazole from Aldrich company (10.0 equivalents) at 25° C. Next, a solution of 138 (3.0 equivalents) in methylene chloride (1.0 M), is added dropwise with stirring at 25° C. After 25 minutes, the mixture is cooled to 0° C. and m-chloroperoxybenzoic acid (4.5 equivalents) is added. The reaction is stirred for an additional 5 minutes and is next diluted with ether and washed with brine (1×) and dried (MgSO$_4$) and concentrated. Purification by flash column chromatography (silica, 50% ethyl acetate in petroleum ether) affords compound 140 (97% yield). scheme 9 step j Note the process can iterate as many times as possible to build large carbonucleotide libraries.

Preparation of 142

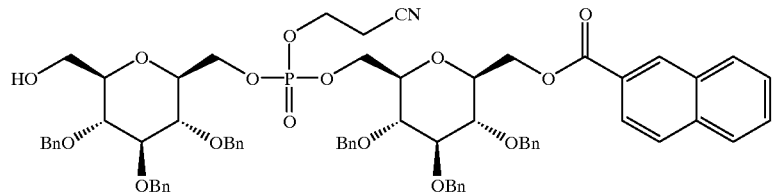

142

A solution of 140 (1.0 equivalents) in acetic acid-tetrahydrofuran-water (3:1:1), (0.01 M) is stirred for 18 hours at 25° C. The reaction is then diluted with ether and washed with NaHCO$_3$ (3×), brine (1×) and dried (MgSO$_4$) and concentrated. Purification by flash column chromatography (silica, 60% ethyl acetate in petroleum ether) affords compound 142 (95% yield). scheme 9 step k Note the process can iterate as many times as possible to build large carbonucleotide libraries.

Preparation of 144

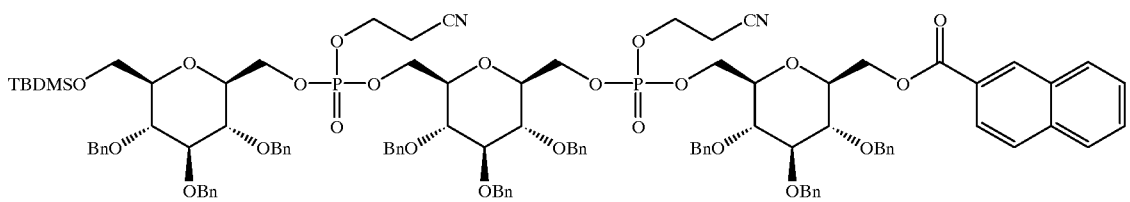

144

To a solution of 138 (1.0 equivalents) in methylene chloride (0.10 M), is added 1-H-tetrazole from Aldrich company (10.0 equivalents) at 25° C. Next, a solution of 142 (3.0 equivalents) in methylene chloride (1.0 M), is added dropwise with stirring at 25° C. After 25 minutes, the mixture is cooled to 0° C. and m-chloroperoxybenzoic acid (4.5 equivalents) is added. The reaction is stirred for an additional 5 minutes and is next diluted with ether and washed with brine (1×) and dried (MgSO$_4$) and concentrated. Purification by flash column chromatography (silica, 50% ethyl acetate in petroleum ether) affords compound 144 (97% yield). scheme 9 step j Note the process can iterate as many times as possible to build large carbonucleotide libraries.

Preparation of 146

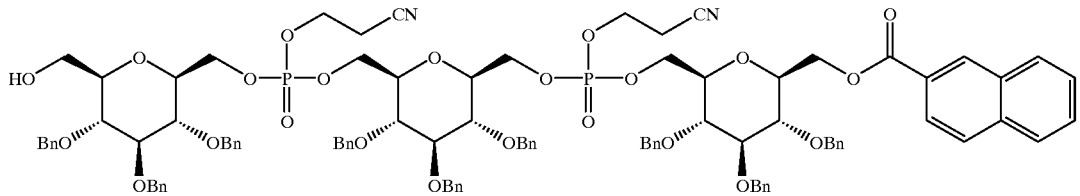

146

A solution of 144 (1.0 equivalents) in acetic acid-tetrahydrofuran-water (3:1:1), (0.01 M total) is stirred for 18 hours at 25° C. The reaction is then diluted with ether and washed with NaHCO₃ (3×), brine (1×) and dried (MgSO₄) and concentrated. Purification by flash column chromatography (silica, 60% ethyl acetate in petroleum ether) affords compound 146 (95% yield). scheme 9 step k Note the process can iterate as many times as possible to build large carbonucleotide libraries.

Preparation of 148

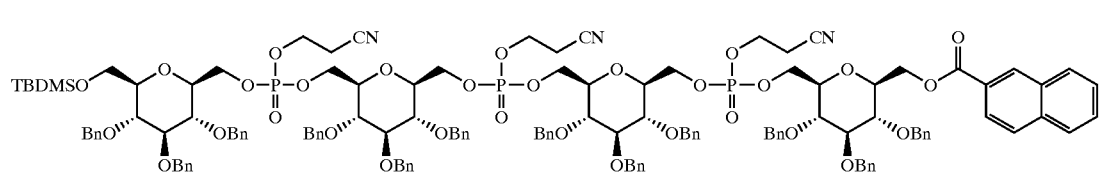

To a solution of 138 (1.0 equivalents) in methylene chloride (0.10 M), is added 1-H-tetrazole from Aldrich company (10.0 equivalents) at 25° C. Next, a solution of 146 (3.0 equivalents) in methylene chloride (1.0 M), is added dropwise with stirring at 25° C. After 25 minutes, the mixture is cooled to 0° C. and m-chloroperoxybenzoic acid (4.5 equivalents) is added. The reaction is stirred for an additional 5 minutes and is next diluted with ether and washed with brine (1×) and dried (MgSO₄) and concentrated. Purification by flash column chromatography (silica, 50% ethyl acetate in petroleum ether) affords compound 148 (97% yield). scheme 9 step j Note the process can iterate as many times as possible to build large carbonucleotide libraries.

Preparation of 150

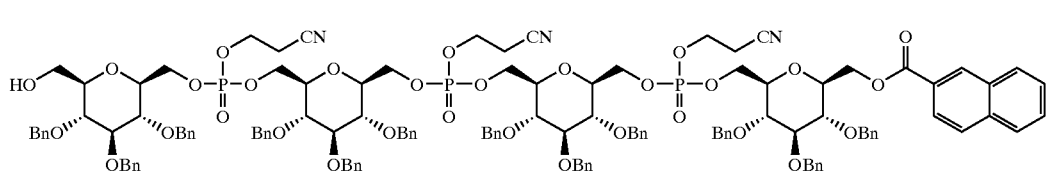

A solution of 148 (1.0 equivalents) in acetic acid-tetrahydrofuran-water (3:1:1), (0.01 M total) is stirred for 18 hours at 25° C. The reaction is then diluted with ether and washed with NaHCO₃ (3×), brine (1×) and dried (MgSO₄) and concentrated. Purification by flash column chromatography (silica, 60% ethyl acetate in petroleum ether) affords compound 150 (95% yield). scheme 9 step k Note the process can iterate as many times as possible to build large carbonucleotide libraries.

Preparation of 152

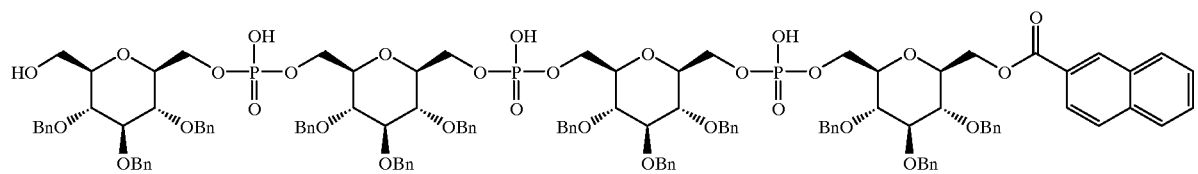

A solution of 150 (1.0 equivalents) is dissolved in concentrated aqueous ammonium hydroxide and acetonitrile (1:1), (0.01 M total). The reaction is then stirred for 2 hours at 50° C. and is subsequently diluted with ether and washed with NaHCO$_3$ (3×), brine (1×) and dried (MgSO$_4$) and concentrated. Purification by flash column chromatography (silica, 80% ethyl acetate in petroleum ether) affords compound 152 (88% yield). scheme 9 step L Preparation of 154

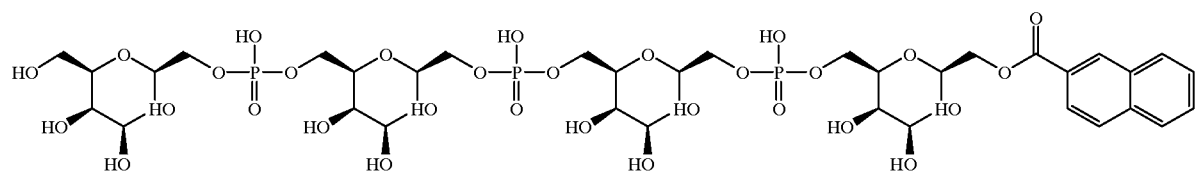

154

A solution of 152 (1.0 equivalents) is dissolved in a mixture of ethanol-tetrahydrofuran-acetic acid (2:1:1), (0.01 M total) at 25° C. The mixture is next exposed to 10% Pd/C (1.0 equivalents) and is then subsequently capped with a hydrogen balloon at 1 atmosphere. The reaction is stirred for 72 hours and is then filtered through celite. The crude mixture is subsequently diluted with ether and washed with NaHCO$_3$ (3×), brine (1×) and dried (MgSO$_4$) and concentrated. Purification by flash column chromatography (silica, 100% ethyl acetate in petroleum ether) affords compound 154 (78% yield). scheme 9 step m Preparation of 174 (R Group=OTES, NPhth or NHAc)

To a solution of tetraacetate derived from 36 or 48 (glucose or glucosamine derived) in methylene chloride (0.01 molar) is added a 1.0 molar solution of Co$_2$(CO)$_8$ (1.5 equivalents) in methylene chloride and diethylmethylsilane (1.5 equivalents) at 0° C. To the stirring reaction mixture, a stream of carbon monoxide is bubbled at 1 ml per 10 seconds for 30 minutes. The reaction mixture is then quenched with water (1.5 equivalents), diluted with ether, washed with sodium bicarbonate (2×), brine (1×) and dried over magnesium sulfate. The crude is purified by column chromatography and affords product 174.

Preparation of 176 (R Group=OTES, NPhth or NHAc)

To a solution of compound 174 in acetonitrile/water (1:1 ratio, 0.1 molar combined), is added RuCl$_3$ (0.03 equiv.) and NaIO$_4$ (4.0 equiv.) at 25° C. and the muddy black mixture is allowed to stir for 1.5 h. The mixture is then diluted with ether (25 mL), washed with water (2×5.0 mL) and brine (1×5 mL). The aqueous layer is back extracted (2×), recombined, and the organic layer was then dried MgSO$_4$ and evaporated. Purification by flash column chromatography yields the desired product 176.

Preparation of 178 (R Group=OTES, NPhth or NHAc)

A solution of triacetate 176 (1.0 equiv.) in methanol (0.5 M), is treated with NaOMe (0.4 equiv.) and allowed to stir at 25° C. for 24 h. The reaction mixture is then condensed and purified by flash column chromatography to afford compound 178.

Preparation of 180 (R Group=OTES, NPhth or NHAc)

To triol 178 (1.0 equivalents) in pyridine (0.10 Molar), is added dimethyoxytritylchloride (DMT chloride) (1.5 equivalents) at 0° C. The reaction is stirred for 2 hours and then diluted with diethylether and washed with ammonium chloride (2×), copper sulfate (2×), brine (1×), dried over MgSO$_4$ and concentrated. Next a solution of the crude intermediate (1.0 equivalents) is dissolved in methylene chloride (0.10 Molar) and diisopropylethylamine (3.3 equivalents) is added at 0° C. Subsequent addition of triethylsilyl trifluoromethanesulfonate (3.3 equivalents) is followed by stirring for 2 hours and then the reaction is diluted with diethylether and washed with ammonium chloride (2×), brine (1×) and then dried (MgSO$_4$) and concentrated. Purification by flash column chromatography affords the intermediate acid, which is then resuspended in THF (1.0 M) and exposed to a 1.0 M solution of BH$_3$-THF (1.5 equivalents) at 0° C. for 1 hour. The reaction is then quenched with methanol for an additional hour and the crude is then diluted with diethylether and washed with ammonium chloride (2×), brine (1×) and then dried (MgSO$_4$) and concentrated. Purification by flash column chromatography affords the desired tetraprotected alcohol 180.

Preparation of 181 (R Group=OTES, NPhth or NHAc)

To a solution of 180 (1.0 equivalents) in methylene chloride (0.10 M), is added tetrazole (4.0 equivalents) at 25° C. The reaction is stirred for 5 minutes and then 2-cyanoethyl-N,N-diisopropyl-chlorophosphoramidite (1.5 equiv.) is added, as prepared from the procedures of Sinha et al. *Nucl. Acids Res.* 1984, 12, 4539. After 15 minutes the reaction is complete and is next diluted with ether and next washed with brine (1×) and is then dried (MgSO$_4$) and concentrated. Purification by flash column chromatography (silica, 30% ethyl acetate in petroleum ether) affords compound 181 (66% yield). scheme 21

Preparation of 182 (R Group=OTES, NPhth or NHAc)

To a solution of triol 178 (0.0 equiv.) in CH$_2$Cl$_2$ (0.5 M) at 0° C. was added triethylamine (1.2 equiv.), 4-DMAP (0.10 equiv.) and then TOSCl (1.1 equiv.). The reaction is stirred for 1 h and then is quenched with saturated ammonium chloride (1.5 mL), diluted with ethyl acetate (25 mL), washed with water (2×5 mL), brine (1×5 mL), back-extracted (2×), recombined, dried (MgSO$_4$) and evaporated. The compound is purified by flash column chromatography and then a solution of the crude intermediate (1.0 equivalents) is dissolved in methylene chloride (0.10 Molar) and diisopropylethylamine (2.2 equivalents) is added at 0° C. Subsequent addition of triethylsilyl trifluoromethanesulfonate (2.2 equivalents) is followed by stirring for 2 hours and then the reaction is diluted with diethylether and washed with ammonium chloride (2×), brine (1×) and then dried (MgSO$_4$) and concentrated. Purification by flash column chromatography affords the protected tosylatelacid 182.

Preparation of 183 (R Group=OTES, NPhth or NHAc)

To a solution of triol 182 (0.0 equiv.) in CH$_2$Cl$_2$ (0.5 M) at 0° C., is added sodium-azide (1.2 equiv.) from Aldrich chemical company at 0° C. The reaction is stirred for 1 h and then is quenched with saturated ammonium chloride (1.5 mL), diluted with ethyl acetate (25 mL), washed with water (2×5 mL), brine (1×5 mL), back-extracted (2×), recombined, dried (MgSO$_4$) and evaporated. The compound is purified by flash column chromatography and affords compound 183.

Preparation of 185 (R Group=OTES, NPhth or NHAc)

A solution of 183 (1.0 equivalents) in ethanol (0.01 M total) at 25° C. is exposed to 10% Pd(OH)$_2$—C (0.1 equivalents) and is then subsequently capped with a hydrogen balloon at 1 atmosphere. The reaction is stirred for 72 hours and is then filtered through celite. The crude mixture is subsequently diluted with ether and washed with NaHCO$_3$ (3×), brine (1×) and dried (MgSO$_4$) and concentrated. Purification by flash column chromatography affords compound 185 scheme 21.

Preparation of 191

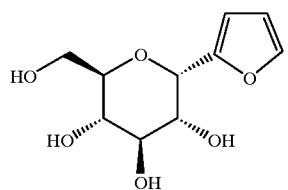

191

A solution of starting material 190 as disclosed by Schmidt, R. R. et al. (*Liebigs Ann. Chem.* 1987, 825), (1.0 equivalents) is dissolved in a mixture of ethanol-tetrahydrofuran-acetic acid (2:1:1), (0.01 M total) at 25° C. The mixture is next exposed to 10% Pd/C (1.0 equivalents) and is then subsequently capped with a hydrogen balloon at 1 atmosphere. The reaction is stirred for 72 hours and is then filtered through celite. The crude mixture is subsequently diluted with ether and washed with NaHCO$_3$ (3×), brine (1×) and dried (MgSO$_4$) and concentrated. Purification by flash column chromatography (silica, 100% ethyl acetate in petroleum ether) affords compound 191. scheme 22 step a Preparation of 192

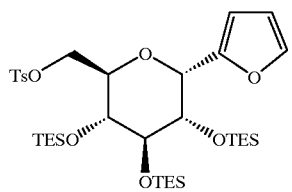

192

To a solution of 191 (1.0 equivalents) in methylene chloride (0.10 Molar) is added tosylchloride (1.2 equivalents) at 0° C. Subsequent addition of triethylamine (1.5 equivalents) is followed by stirring for 2 hours and then the reaction is diluted with diethylether and washed with ammonium chloride (2×), brine (1×) and then dried (MgSO$_4$) and concentrated to afford the crude tosylate. Next a solution of the crude intermediate (1.0 equivalents) is dissolved in methylene chloride (0.10 Molar) and diisopropylethylamine (3.3 equivalents) is added at 0° C. Subsequent addition of triethylsilyl trifluoromethanesulfonate (3.3 equivalents) is followed by stirring for 2 hours and then the reaction is diluted with diethylether and washed with ammonium chloride (2×), brine (1×) and then dried (MgSO$_4$) and concentrated. Purification by flash column chromatography affords compound 192. scheme 22 step b Preparation of 193

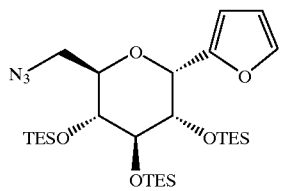

193

To a solution of 192 (1.0 equivalents) in methylene chloride (0.10 Molar) is added sodium azide from Aldrich chemical company (1.2 equivalents) at 0° C. Subsequent stirring for 2 hours is followed by dilution with diethylether and washing with ammonium chloride (2×), brine (1×) and then MgSO$_4$. The solution is then concentrated and purification by flash column chromatography affords compound 193. scheme 22 step c Preparation 194

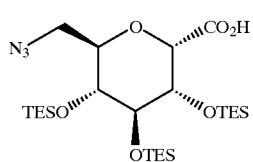

194

To solution of 193 in CCl$_4$ (0.33 M), CH$_3$CN (0.33 M) and water (0.22 M) at 0° C. is added RuCl$_3$ (0.03 equiv.) and NaIO$_4$ (4.0 equiv.) and the muddy black mixture is allowed to stir for 1.5 h. The mixture is then diluted with ether (25 mL), washed with water (2×5.0 mL) and brine (1×5 mL). The aqueous layer is back extracted (2×), recombined, and the organic layer is then dried MgSO$_4$ and evaporated. Purification by flash column chromatography affords the compound 194. scheme 22 step d Preparation of 196

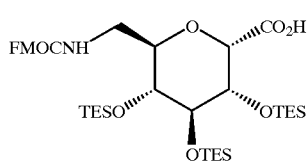

196

A solution of 194 (1.0 equivalents) is dissolved in ethanol (0.01 M total) at 25° C. The mixture is next exposed to 10% Pd/C (0.01 equivalents) and is then subsequently capped with a hydrogen balloon at 1 atmosphere. The reaction is stirred for 72 hours and is then filtered through celite. The crude mixture is subsequently diluted with ether and washed with NaHCO$_3$ (3×), brine (1×) and Cried (MgSO$_4$) and concentrated. Next, to a solution of crude amine (1.0 equivalents) in methylene chloride (0.10 Molar), is added sodium bicarbonate (2.0 equivalents) at 0° C. Subsequent addition of 9-fluorenylmethyl chloroformate (FMOC-Cl, 1.2 equivalents) is followed by stirring for 2 hours and then the reaction is diluted with diethylether and washed with ammonium chloride (2×), brine (1×) and then dried (MgSO$_4$) and concentrated. Purification by flash column chromatography affords compound 196. scheme 22 steps e–f Preparation of 197

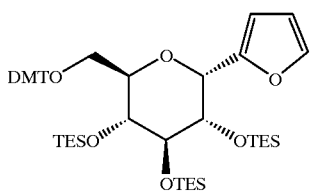

To Tetrol 191 (1.0 equivalents) in pyridine (0.10 Molar), is added dimethyoxytritylchloride (DMT chloride) (2.5 equivalents) at 0° C. The reaction is stirred for 2 hours and then diluted with diethylether and washed with ammonium chloride (2x), copper sulfate (2x), brine (1x), dried over MgSO₄ and concentrated. Next a solution of the crude intermediate (1.0 equivalents) is dissolved in methylene chloride (0.10 Molar) and diisopropylethylamine (3.3 equivalents) is added at 0° C. Subsequent addition of triethylsilyl trifluoromethanesulfonate (3.3 equivalents) is followed by stirring for 2 hours and then the reaction is diluted with diethylether and washed with ammonium chloride (2x), brine (1x) and then dried (MgSO₄) and concentrated. Purification by flash column chromatography affords compound 197. scheme 22 step g Preparation of 198

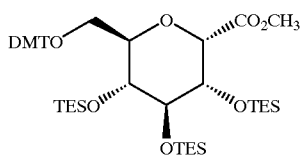

To solution of 197 in CCl₄ (0.33 M), CH₃CN (0.33 M) and water (0.22 M) at 0° C. is added RuCl₃ (0.03 equiv.) and NaIO₄ (4.0 equiv.) and the muddy black mixture is allowed to stir for 1.5 h. The mixture is then diluted with ether (25 mL), washed with water (2×5.0 mL,) and brine (1×5 mL). The crude is then resuspended in a mixture of methylene chloride/water (1:1, 0.1 M total) and diazomethane (1.2 equivalents) is gradually dropped into the flask via an addition funnel at the rate of 1 drop/10 seconds. After complete addition the mixture is diluted. with ether, washed with brine (2x) and the aqueous layer is back extracted (2x) recombined, and the organic layer is then dried MgSO₄ and evaporated. Purification by flash column chromatography affords the compound 198. scheme 22 step h Preparation of 200

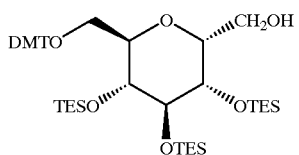

To a solution of 198 (1.0 equivalents) in methylene chloride (0.10 Molar) is added a 1.0 M solution of DIBALH in methylene chloride from Aldrich chemical company (1.2 equivalents) at 0° C. Subsequent stirring for 2 hours is followed by dilution with diethylether and washing with sodium-potassium tartrate (2x), brine (1x) and then MgSO₄. The solution is then concentrated and purification by flash column chromatography affords compound 200. scheme 22 step i Preparation of 201

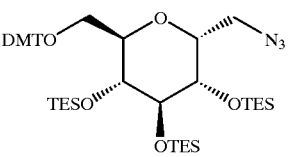

A solution of 200 (1.0 equivalents) in tetrahydrofuran (0.18 M) is treated with DPPA (diphenylphosphorylazide, 2.0 equivalents), triphenylphosphine (1.3 equivalents) and DIAD (diisopropyl-azo-dicarboxylate, 1.3 equivalents). The reaction is heated to 80° C. for 3 hours and then diluted with ether (2x) and washed with 0.5 M aqueous NaOH (2x). The organic layer is dried over MgSO₄ and evaporated. Purification by flash column chromatography affords compound 201. scheme 22 step j Preparation of 202

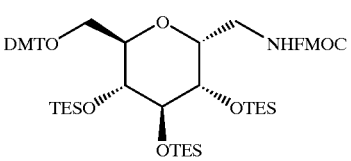

A solution of 201 (1.0 equivalents) is dissolved in ethanol (0.01 M total) at 25° C. The mixture is next exposed to 10% Pd/C (0.01 equivalents) and is then subsequently capped with a hydrogen balloon at 1 atmosphere. The reaction is stirred for 72 hours and is then filtered through celite. The crude mixture is subsequently diluted with ether and washed with NaHCO₃ (3x), brine (1x) and dried (MgSO₄) and concentrated. Next, to a solution of crude amine (1.0 equivalents) in methylene chloride (0.10 Molar), is added sodium bicarbonate (2.0 equivalents) at 0° C. Subsequent addition of 9-fluorenylmethyl chloroformate (FMOC-Cl, 1.2 equivalents) is followed by stirring for 2 hours and then the reaction is diluted with diethylether and washed with ammonium chloride (2x), brine (1x) and then dried (MgSO₄) and concentrated. Purification by flash column chromatography affords compound 202. scheme 22 step e Preparation of 204

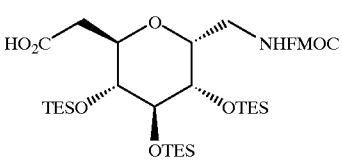

To a solution of 202 (1.0 equivalents) in methylene chloride (0.10 Molar) is added 10% HCOOH from Aldrich chemical company (1.2 equivalents) at 0° C. Subsequent stirring for 2 hours is followed by dilution with diethylether and washing with sodium bicarbonate (2x), brine (1x) and then MgSO₄. The solution is then resuspended in t-BuOH (0.10 M) and pH 7 buffer (0.10 M) and is then exposed to KMnO₄ (1.2 equivalents) for 2 hours at 0° C. The reaction mixture is next washed with sodium bicarbonate (2x), brine (1x) and then MgSO₄. The organic layer is then concentrated and purified by flash column chromatography to afford compound 204. scheme 22 step k Preparation of 206

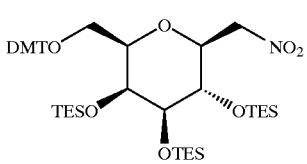

To Tetrol 205 (1.0 equivalents) (as disclosed by Petrus, L. et al. Chem. zvesti. 1982, 36, 103) in pyridine (0.10 Molar), is added dimethyoxytritylchloride (DMT chloride) (2.5 equivalents) at 0° C. The reaction is stirred for 2 hours and then diluted with diethylether and washed with ammonium chloride (2×), copper sulfate (2×), brine (1×), dried over $MgSO_4$ and concentrated. Next a solution of the crude intermediate (1.0 equivalents) is dissolved in methylene chloride (0.10 Molar) and diisopropylethylamine (3.3 equivalents) is added at 0° C. Subsequent addition of triethylsilyl trifluoromethanesulfonate (3.3 equivalents) is followed by stirring for 2 hours and then the reaction is diluted with diethylether and washed with ammonium chloride (2×), brine (1×) and then dried ($MgSO_4$) and concentrated. Purification by flash column chromatography affords compound 206. scheme 23 step a Preparation of 207

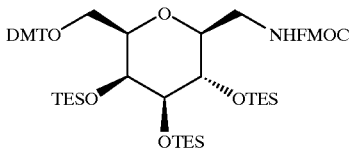

To a solution of 206 (1.0 equivalents) in diethylether (0.08 M), is added lithiumaluminumhydride (LAH) (1.5 equivalents) at 30° C. The reaction is refluxed for 2 hours and then quenched with methanol and diluted with ether. The reaction is next worked-up with sodium potassium tartrate (2×), brine (1×) and is then dried ($MgSO_4$) and concentrated. The crude mixture is resuspended in methylene chloride (0.10 Molar) and to it is added sodium bicarbonate (2.0 equivalents) at 0° C. Subsequent addition of 9-fluorenylmethyl chloroformate (FMOC-Cl, 1.2 equivalents) is followed by stirring for 2 hours and then the reaction is diluted with diethylether and washed with ammonium chloride (2×), brine (1×) and then dried ($MgSO_4$) and concentrated. Purification by flash column chromatography affords compound 207. scheme 23 step b Preparation of 208

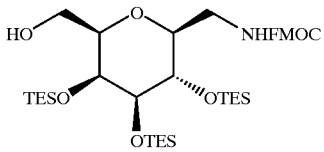

To a solution of 207 (1.0 equivalents) in methylene chloride (0.10 Molar) is added 10% HCOOH (1.1 equivalents). The reaction is stirred at 0° C. for 2 minutes and is then diluted with ether and washed with sodium bicarbonate (2×), brine (1×) and then dried ($MgSO_4$) and concentrated. Purification by flash column chromatography affords compound 208. scheme 23 step c Preparation of 209

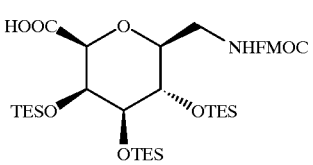

To solution of 208 in $CCl_4$ (0.33 M), $CH_3CN$ (0.33 M) and water (0.22 M) at 20° C. is added $RuCl_3$ (0.03 equiv.) and $NaIO_4$ (4.0 equiv.) and the muddy black mixture is allowed to stir for 10 min. The mixture is then diluted with ether (25 mL), washed with water (2×5.0 mL) and brine (1×5 mL). The aqueous layer is back extracted (2×), recombined, and the organic layer iss then dried $MgSO_4$ and evaporated. Purification by flash column chromatography affords the compound 209. scheme 23 step d Preparation of 210

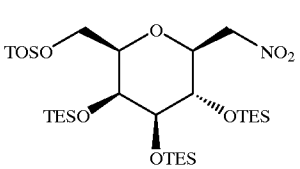

To a solution of 205 (1.0 equivalents) in methylene chloride (0.10 Molar) is added tosylchloride (1.2 equivalents) at 0° C. Subsequent addition of triethylamine (1.5 equivalents) is followed by stirring for 2 hours and then the reaction is diluted with diethylether and washed with ammonium chloride (2×), brine (1×) and then dried ($MgSO_4$) and concentrated to afford the crude tosylate. Next a solution of the crude intermediate (1.0 equivalents) is dissolved in methylene chloride (0.10 Molar) and diisopropylethylamine (3.3 equivalents) is added at 0° C. Subsequent addition of triethylsilyl trifluoromethanesulfonate (3.3 equivalents) is followed by stirring for 2 hours and then the reaction is diluted with diethylether and washed with ammonium chloride (2×), brine (1×) and then dried ($MgSO_4$) and concentrated. Purification by flash column chromatography affords compound 210. scheme 23 step e Preparation of 211

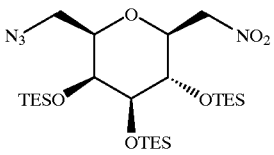

To a solution of 210 (1.0 equivalents) in methylene chloride (0.10 Molar) is added sodium azide from Aldrich chemical company (1.2 equivalents) at 0° C. Subsequent stirring for 2 hours is followed by dilution with diethylether and washing with ammonium chloride (2×), brine (1×) and then $MgSO_4$. The solution is then concentrated and purification by flash column chromatography affords compound 211. scheme 23 step f

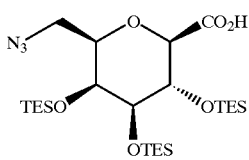

212

To solution of 211 in CCl$_4$ (0.33 M), CH$_3$CN (0.33 M) and water (0.22 M) at: 20° C. is added RuCl$_3$ (0.03 equiv.) and NaIO$_4$ (4.0 equiv.) and the muddy black mixture is allowed to stir for 10 min. The mixture is then diluted with ether (25 mL), washed with water (2×5.0 mL) and brine (1×5 mL). The aqueous layer is back extracted (2×), recombined, and the organic layer iss then dried MgSO$_4$ and evaporated. Purification by flash column chromatography affords the compound 212. scheme 23 step g Preparation of 213

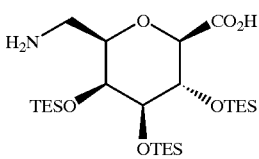

213

A solution of 212 (1.0 equivalents) in ethanol (0.01 M total) at 25° C. is exposed to 10% Pd/C (0.1 equivalents) and is then subsequently capped with a hydrogen balloon at 1 atmosphere. The reaction is stirred for 72 hours and is then filtered through celite. The crude mixture is subsequently diluted with ether and washed with NaHCO$_3$ (3×), brine (1×) and dried (MgSO$_4$) and concentrated. Purification by flash column chromatography affords compound 213. scheme 23 step h Preparation of 214

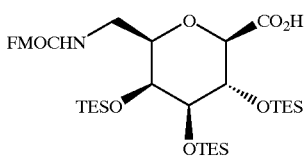

214

Compound 213 is suspended in methylene chloride (0.10 Molar) and to it is added sodium bicarbonate (2.0 equivalents) at 0° C. Subsequent addition of 9-fluorenylmethyl chloroformate (FMOC-Cl, 1.2 equivalents) is followed by stirring for 2 hours and then the reaction is diluted with diethylether and washed with ammonium chloride (2×), brine (1×) and then dried (MgSO$_4$) and concentrated. Purification by flash column chromatography affords compound 214. scheme 23 step i Preparation of 215

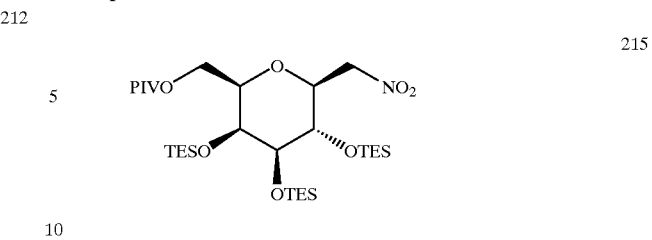

215

To a solution of 205 (1.0 equivalents) in pyridine (0.10 Molar), is added trimethylacetyl chloride (pivaloyl chloride) (2.5 equivalents) at 0° C. The reaction is stirred for 2 hours and then diluted with diethylether and washed with ammonium chloride (2×), copper sulfate (2×), brine (1×), dried over MgSO$_4$ and concentrated. Next a solution of the crude intermediate (1.0 equivalents) is dissolved in methylene chloride (0.10 Molar) and diisopropylethylamine (3.3 equivalents) is added at 0° C. Subsequent addition of triethylsilyl trifluoromethanesulfonate (3.3 equivalents) is followed by stirring for 2 hours and then the reaction is diluted with diethylether and washed with ammonium chloride (2×), brine (1×) and then dried (MgSO$_4$) and concentrated. Purification by flash column chromatography affords compound 215. scheme 23 step j Preparation of 216

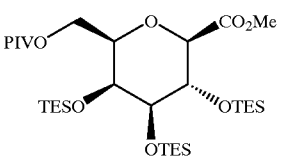

216

To solution of 215 in CCl$_4$ (0.33 M), CH$_3$CN (0.33 M) and water (0.22 M) at 20° C. is added RuCl$_3$ (0.03 equiv.) and NaIO$_4$ (4.0 equiv.) and the muddy black mixture is allowed to stir for 10 min. The mixture is then diluted with ether (25 mL), washed with water (2×5.0 mL) and brine (1×5 mL). The aqueous layer is back extracted (2×), recombined, and the organic layer is then dried MgSO$_4$ and evaporated. The crude is then resuspended in a mixture of methylene chloride/water (1:1, 0.1 M total) and diazomethane (1.2 equivalents) is gradually dropped into the flask via an addition funnel at the rate of 1 drop/10 seconds. After complete addition the mixture is diluted with ether, washed with brine (2×) and the aqueous layer is back extracted (2×) recombined, and the organic layer is then dried MgSO$_4$ and evaporated. Purification by flash column chromatography affords the compound 216. scheme 23 step k Preparation of 217

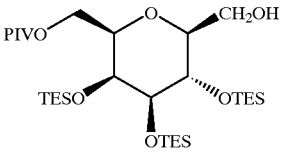

217

To a solution of 216 (1.0 equivalents) in methylene chloride (0.10 Molar) is added a 1.0 M solution of DIBALH in methylene chloride from Aldrich chemical company (1.2 equivalents) at 0° C. Subsequent stirring for 2 hours is followed by dilution with diethylether and washing with sodium-potassium tartrate (2×), brine (1×) and then MgSO₄. The solution is then concentrated and purification by flash column chromatography affords compound 217. scheme 23 step l Preparation of 218

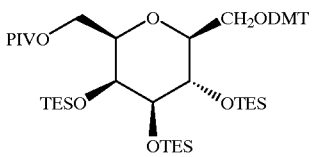

To 217 (1.0 equivalents) in pyridine (0.10 Molar), is added dimethyoxytritylchloride (DMT chloride) (1.1 equivalents) at 0° C. The reaction is stirred for 2 hours and then diluted with diethylether and washed with ammonium chloride (2×), copper sulfate (2×), brine (1×), dried over MgSO₄ and concentrated. Purification by flash column chromatography affords compound 218. scheme 23 step m Preparation of 220

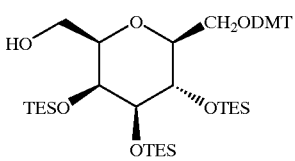

To a solution of 218 (1.0 equivalents) in diethylether (0.08 M), is added lithiumaluminumhydride (LAH) (1.5 equivalents) at 30° C. The reaction is refluxed for 2 hours and then quenched with methanol and diluted with ether. The reaction is next worked-up with sodium potassium tartrate (2×), brine (1×) and is then dried (MgSO₄) and concentrated. Purification by flash column chromatography affords compound 220. scheme 23 step n Preparation of 221

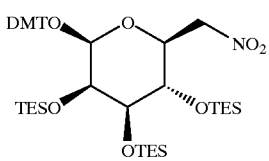

To Tetrol 205 (1.0 equivalents) in pyridine (0.10 Molar), is added dimethyoxytritylchloride (DMT chloride) (2.5 equivalents) at 0° C. The reaction is stirred for 2 hours and then diluted with diethylether and washed with ammonium chloride (2×), copper sulfate (2×), brine (1×), dried over MgSO₄ and concentrated. Next a solution of the crude intermediate (1.0 equivalents) is disolved in methylene chloride (0.10 Molar) and diisopropylethylamine (3.3 equivalents) is added at 0° C. Subsequent addition of triethylsilyl trifluoromethanesulfonate (3.3 equivalents) is followed by stirring for 2 hours and then the reaction is diluted with diethylether and washed with ammonium chloride (2×), brine (1×) and then dried (MgSO₄) and concentrated. Purification by flash column chromatography affords compound 221. scheme 23 step a Preparation of 222

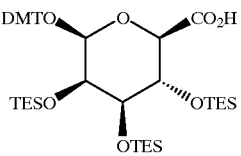

To solution of 221 in CCl₄ (0.33 M), CH₃CN (0.33 M) and water (0.22 M) at 20° C. is added RuCl₃ (0.03 equiv.) and NaIO₄ (4.0 equiv.) and the muddy black mixture is allowed to stir for 10 min. The mixture is then diluted with ether (25 mL), washed with water (2×5.0 mL) and brine (1×5 mL). The aqueous layer is back extracted (2×), recombined, and the organic layer iss then dried MgSO₄ and evaporated. Purification by flash column chromatography affords the compound 222. scheme 23. step o.

Preparation of 224

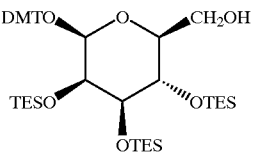

To a solution of 222 (1.0 equivalents) in diethylether (0.08 M), is added lithiumaluminumhydride (LAH) (1.5 equivalents) at 30° C. The reaction is refluxed for 2 hours and then quenched with methanol and diluted with ether. The reaction is next worked-up with sodium potassium tartrate (2×), brine (1×) and is then dried (MgSO₄) and concentrated. Purification by flash column chromatography affords compound 224. scheme 23 step p Preparation of 216

To a stirred solution of the acid 214 (1.0 equivalents) in dimethylformamide (0.10 Molar) at 25° C., is added 1-hydroxybenzotriazole (HOBT; 1.1 equivalents). Next dicyclohexylcarbodiimide (1.2 equivalents) is added and the reaction is stirred for 1 hour in the presence of an appropriately substituted solid support (N-(2-Aminoethyl)-3-amino-propyl glass; aminopolystyrene resin; aminopropyl glass; isothiocyanato glass, all with or without a linker extending from the amino group on the support etc. from Sigma Company). The mixture is then diluted with ether, filtered and the filtrate is washed with aqueous NaHCO₃ (2×), water (2×), and brine (2×). The organic phase is dried over MgSO₄ and then concentrated.

Preparation of 226; 228; 230 or 232

To a stirred solution of the acid 214; 62; 215 or 62 (1.0 equivalents) and the amine 216; 226; 228 or 230 (1.1 equivalents) in dimethylformamide (0.10 Molar) at 25° C., is added 1-hydroxybenzotriazole (HOBT; 1.1 equivalents). Next dicyclohexylcarbodiimide (1.2 equivalents) is added and the reaction is stirred for 14 hours. The mixture is diluted with ether, filtered and the filtrate is washed with aqueous NaHCO₃ (2×), water (2×), and brine (2×). The organic phase is dried over MgSO₄ and then concentrated. Purification by flash column chromatography and then reex posure of the intermediate compound (1.0 equivalents) in dimethyl-formamide (0.10 Molar) at 25° C., is added piperidine (1.1 equivalents). The reaction is stirred for 1 hour and is then diluted with ether, and washed with aqueous $CuSO_4$ (2×), water (2×), and brine (2×). The organic phase is dried over $MgSO_4$ and then concentrated. Purification by flash column chromatography affords compound 226; 228; 230 or 232, respectively. scheme 24

Preparation of 234

To a stirred solution of 232 (1.0 equivalents) in acetonitrile (0.50 Molar) is added an HF pyridine solution (0.50 M) from Aldrich chemical company. The reaction is allowed to stir for five hours and is then condensed. The crude 234 oligomer is then resuspended in p-dioxane (0.50 Molar) to which is added a 3.0 Molar solution of NaOH (3.0 equivalents). The reaction is stirred for 1 hour at 50° C. and is then quenched with aqueous $NH_4Cl$ (2×) and subsequently lyophilized. Purification by HPLC chromatography affords compound 234. scheme 24

Preparation of Peptoid Combinatorial Libraries (Scheme 500)

A depiction of the generation of a combinatorial library for oligopeptoid compounds is shown in scheme 500. The example uses an alphabet of eight D-aldose hexose sugars (other sugars groups such as the D/L ketoses and L-configurations of aldose hexoses, may be used) and carries the synthesis to a degree of three or 512 compounds. (The process can repeat itself to afford the library of desired size). Standard chemistry is shown and follows the reaction conditions as described above herein for peptoid synthesis. The solid support used is the standard N-(2-Aminoethyl)-3-amino-propyl glass support; amino-polystyrene resin; aminopropyl glass; isothiocyanato glass and others as purchased from Sigma company. All supports may be with or without a linker extending from the amino group on the support (eg. succinate linkage, amide, ether, alkyl chain with terminal carbon activated as free alcohol, bromide etc.).

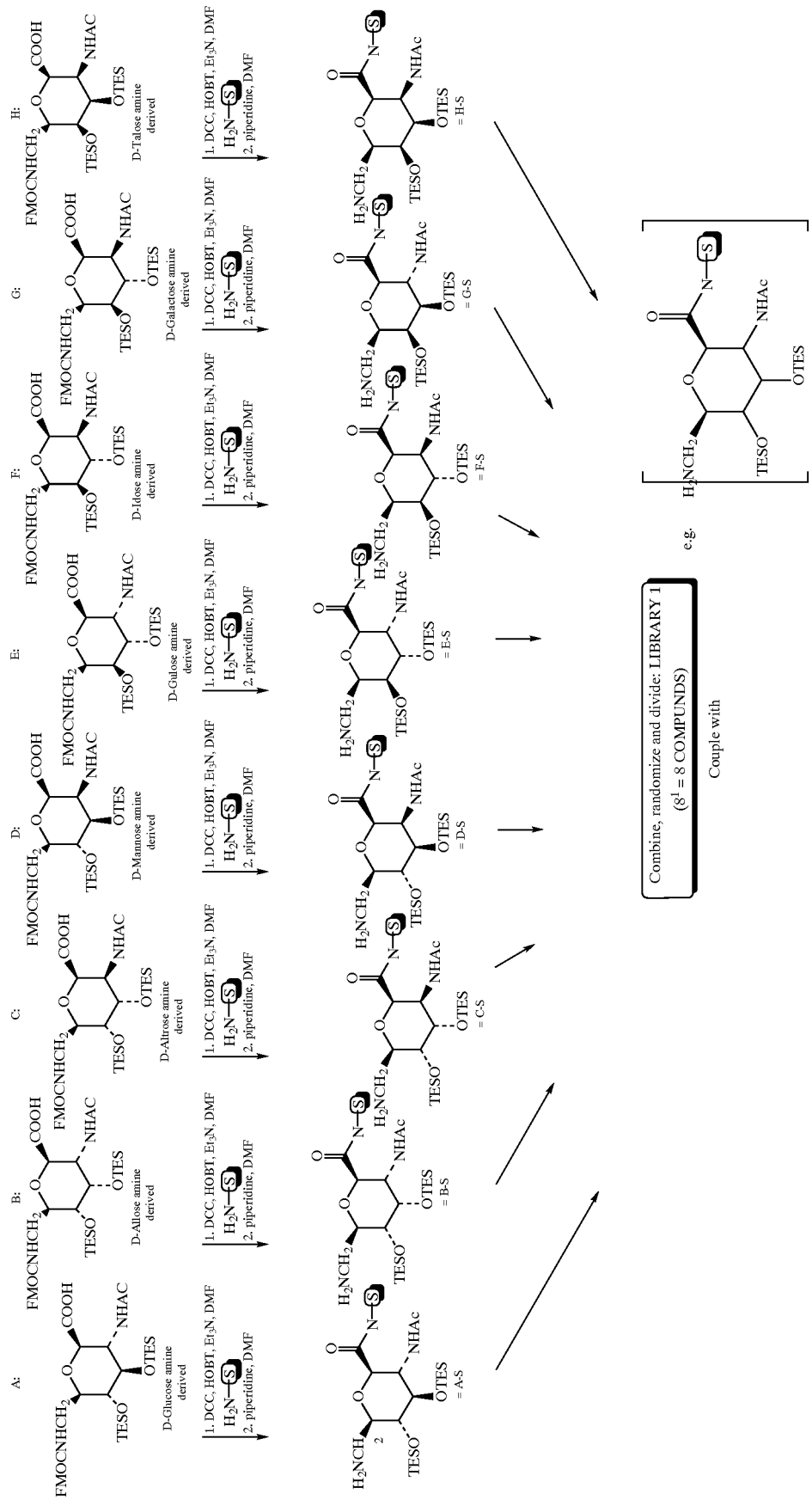

Scheme 500B

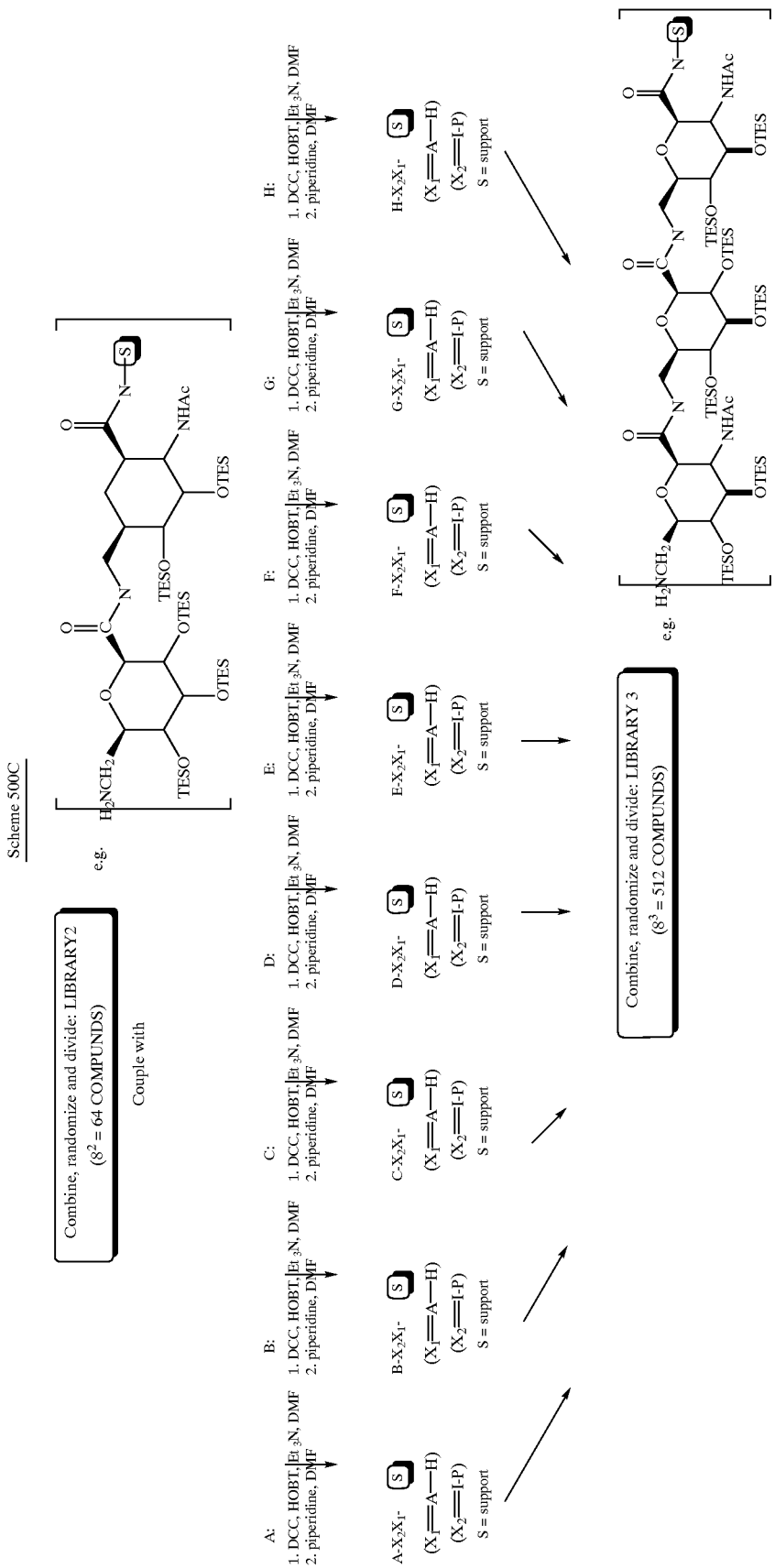

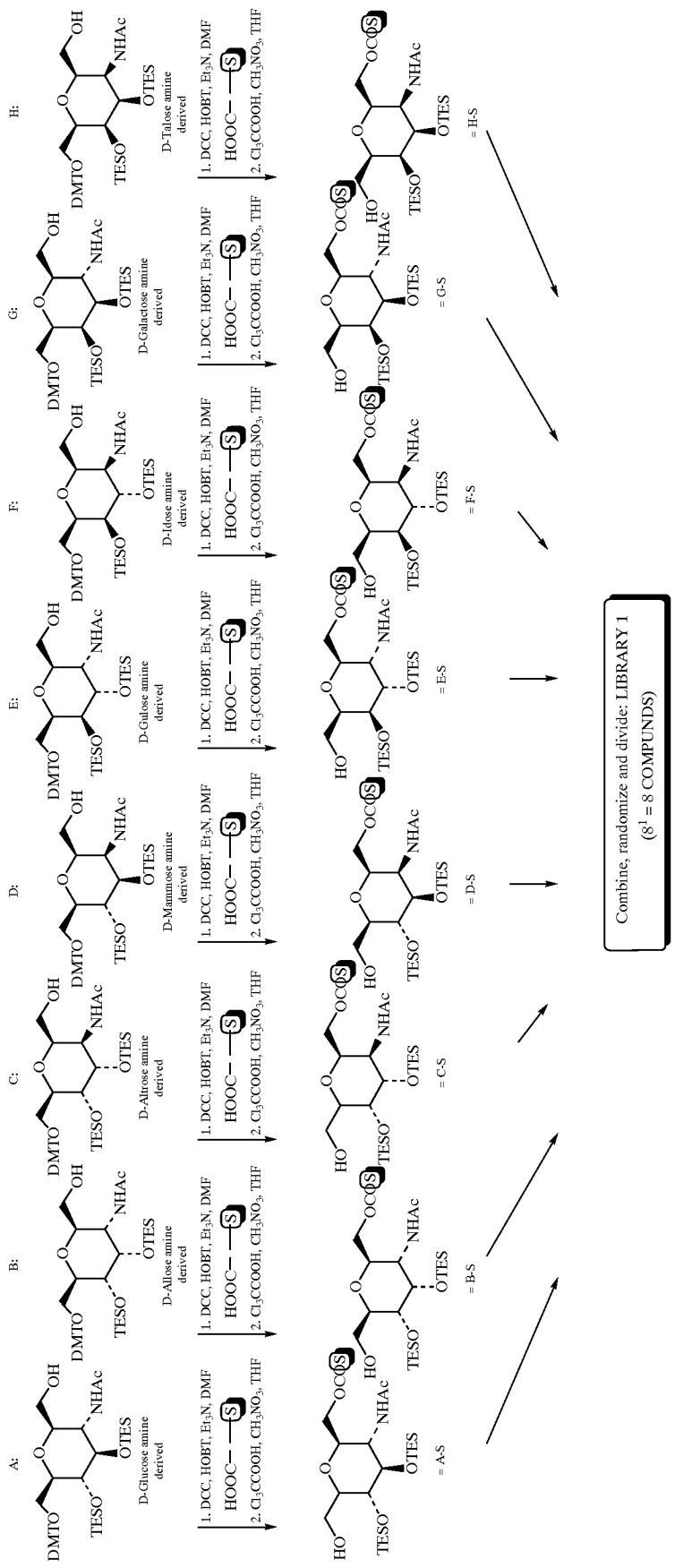

Scheme 550B

Scheme 550c

Preparation of Nucleotoid Combinatorial Libraries (Scheme 550)

A depiction of the generation of a combinatorial library for oligonucleotoid compounds is shown in scheme 550. The example uses an alphabet of eight D-aldose hexose sugars (other sugars groups such as the D/L ketoses and L-configurations of aldose hexoses, may be used) and carries the synthesis to a degree of three or 512 compounds. (The process can repeat itself to afford the library of desired size). Standard chemistry is shown and follows the reaction conditions as described above herein for carbonucleotoid synthesis. The solid support used is the standard N-(2-Aminoethyl)-3-amino-propyl glass support; amino-polystyrene resin; aminopropyl glass; isothiocyanato glass and others as purchased from Siagma company. All supports may be with or without a linker extending from the amino group on the support (eg. succinate linkage, amide, ether, alkyl chain with terminal carbon activated as free alcohol, bromide etc.).

Preparation of Compound 2000

To a solution of 76 (1.0 equiv) was added methylene chloride (0.1 M) and benzaldehyde (1.1 equiv), and the solution was exposed to ZnCl (1.1 equiv) at 25° C. and allowed to stir for 2.5 hour. The solution is then diluted with ether and then washed with a saturated solution of sodium bicarbonate (2x), water (2x), brine (1x) and then dried over MgSO$_4$. The compound is purified by flash column chromatography to yield the desired benzylidene.

1. Synthesis of a C-2 differentiated sugar

Scheme 2000a

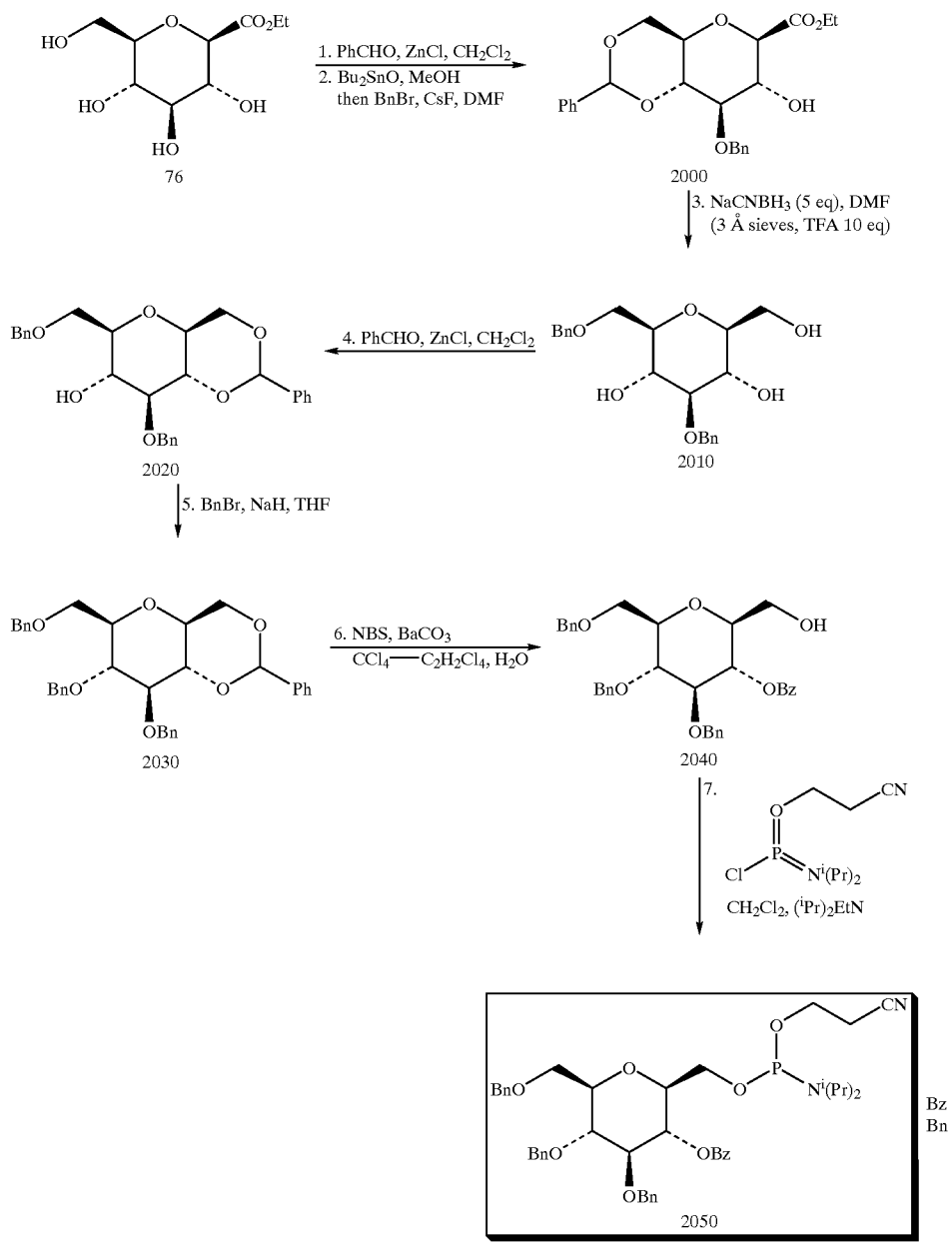

Bz = Benzoate
Bn = Benzyl ether

2. Connection of the C-2 differentiated sugar to a solid support

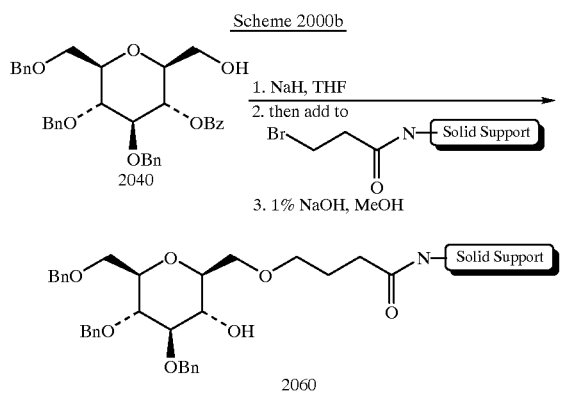

Scheme 2000b

The benzylidene is then azeotroped with benzene (2×100 mL) and then dried overnight under vacuum over $P_2O_5$. A mixture of benzylidene, dibutyl tin oxide (1.2 equiv.) and dry methanol (0.25 M) are heated at reflux for 4 h until the solution became clear and homogeneous. (An automatic stirring apparatus may be necessary.) The solvent is next removed in vacuo to give a foamy white tin complex which was then azeotroped with benzene (2×) and dried (2 h to overnight) under vacuum over $P_2O_5$. Next, anhydrous DMF (0.2 M) is added to redissolve the tin complex and then CsF (1.2 equiv.) and finally Benzyl bromide (1.5 equiv.) are added and then heated (40° C.) overnight. The clear solution is partially distilled under vacuum, (3.3 mm Hg, 75–100° C.) to obtain ⅕ the original volume of solvent. Reaction mixture was then diluted with ethyl acetate (2 L) and washed with a small amount of water (2×) to remove cesium salts. Aqueous layer is back extracted with ethyl acetate (3×) and then recombined with the organic layer which was then dried over $MgSO_4$ and evaporated. Purification by flash column chromatography yields the desired benzyl ether 2000. For related chemistry see Nagashima. N.; Ohno. M. *Chemistry Letters, Chem. Soc. of Japan* 1987. 141.

Preparation of Compound 2010

Procedure adopted from Johansson R.; Samuelsson; B. *J. Chem. Soc., Chem. Commun.*, 1984, 201. To a solution of the benzylidene acetal (1 equiv) and sodium cyanoborohydride (5 equiv.) in DMF (0.125 M) containing powedered 3 angtrsom molecular sieves is added trifluoroacetic acid (10 equiv) and the reaction is allowed to stir at 0° C. until no starting material remains. Reaction mixture is then diluted with ethyl acetate (2 L) and washed with a small amount of water (2×) and brine (2×). Aqueous layer is back extracted with ethyl acetate (3×) and then recombined with the organic layer which was then dried over $MgSO_4$ and evaporated. Purification by flash column chromatograhy yields the desired benzyl ether 2010.

Preparation of Compound 2020

To a solution of 2010 (1.0 equiv) was added methylene chloride (0.1 M) and benzaldehyde (1.1 equiv), and the solution was exposed to ZnCl (1.1 equiv) at 25° C. and allowed to stir for 2.5 hour. The solution is then diluted with ether and then washed with a saturated solution of sodium bicarbonate (2×), water (2×), brine (1×) and then dried over $MgSO_4$. The compound is purified by flash column chromatography to yield the desired benzylidene 2020.

Preparation of Compound 2030

To a solution of alcohol 2020 (22.0 g, 0.1068 mol, 1.0 equiv.) in THF (0.5 M) at 0° C., is added NaH (1.0 equiv., 35% dispersion in mineral oil) over several portions. The reaction mixture is warmed to room temperature and stirred 1 h. Next, the reaction iss cooled to 0° C. and treated with benzyl bromide (1.0 equiv.) and stirred for 1.5 h. A saturated solution of ammonium chloride (50 mL) is added dropwise to quench the reaction mixture at 0° C. and the mixture was diluted with ethyl acetate, washed with water (2×), brine (1×), dried over $MgSO_4$ and evaporated. Purification by flash column chromatography yields tribenzyl ether 2030.

Preparation of Compound 2040

Procedure as adopted from Hanessian S.; *Organic Syntheses* 1987, 243. To a suspension containing 1.0 equivalent of benzylidene 2030 in one molar carbon tetrachloride and 1,1.2.2-tetrachloroethane (1.5 equivalent) is added 1.2 equivalents of N-bromosuccinimide and 0.5 equivalents of barium carbonate. The resulting suspension is heated at the reflux temperature of the mixture with mechanical stirring for a period of 2.5 hour and filtered while hot. The solution is washed with water (3×). then dried over anhydrous sodium sulfate and evaporated. Purification by flash column chromatography yields tribenzyl ether 2040

Preparation of Compound 2050

To a solution of 2040 (1.0 equivalents) in methylene chloride (0.10 M), is added diisopropylethylamine (4.0 equivalents) at 25° C. The reaction is stirred for 5 minutes and then 2-cyanoethyl-N,N-diisopropyl-chlorophosphoramidite (1.5 equiv) is added, as prepared from the procedures of Sinha et al. *Nucl. Acids Res.* 1984, 12, 4539. After 15 minutes the reaction is Synthesis of a C1-C2-Phosophodiester oligomer using a solid support

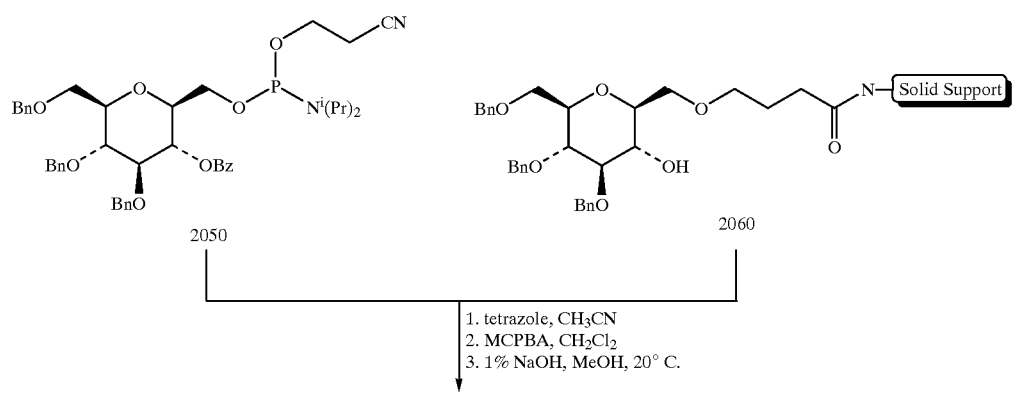

Scheme 2001

1. tetrazole, $CH_3CN$
2. MCPBA, $CH_2Cl_2$
3. 1% NaOH, MeOH, 20° C.

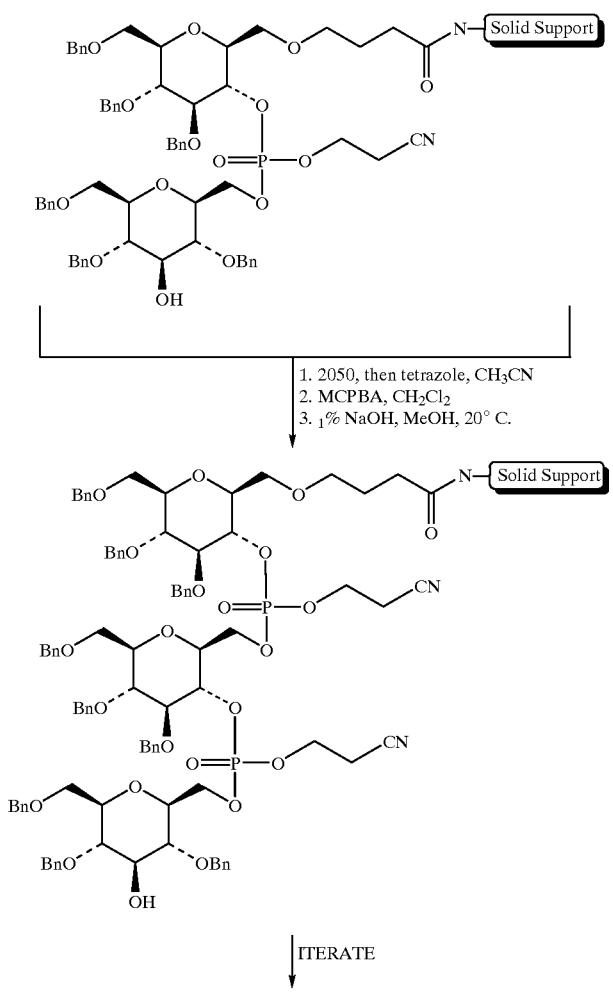

brine (1x) and is then dried (MgSO$_4$) and concentrated. Purification by flash column chromatography (silica, 30% ethyl acetate in petroleum ether) affords compound 2050 (as shown in scheme 2000).

Preparation of compound 2060

To a solution of alcohol 2040 (1.0 equiv.) in THF (0.5 M) at 0° C., is added NaH (1.0 equiv., 35% dispersion in mineral oil) over several portions. The reaction mixture is warmed to room temperature and stirred 1 h. Next, the reaction is cooled to 0° C. and exposed to the solid support functionalized with a bromide linker or any reasonable leaving group attached (1.0 equiv.) and stirred for 2 hours. A saturated solution of ammonium chloride (50 mL) is added dropwise to quench the reaction mixture at 0° C. and the support was washed with ethyl acetate, 1% NaOH in methanol (2x) to remove the benzoate and finally brine (1x) to give 2 0 6 0. The solid support used is the standard N-(2-Aminoethyl)-3-amino-propyl glass support; amino-polystyrene resin; aminopropyl) glass; isothiocyanato glass and others as purchased from Sigma company. All supports may be with or without a linker extending from the amino group on the support (eg. succinate linkage, amide, ether, alkyl chain with terminal carbon activated as free alcohol, bromide etc.).

1. Synthesis of a C-3 differentiated sugar

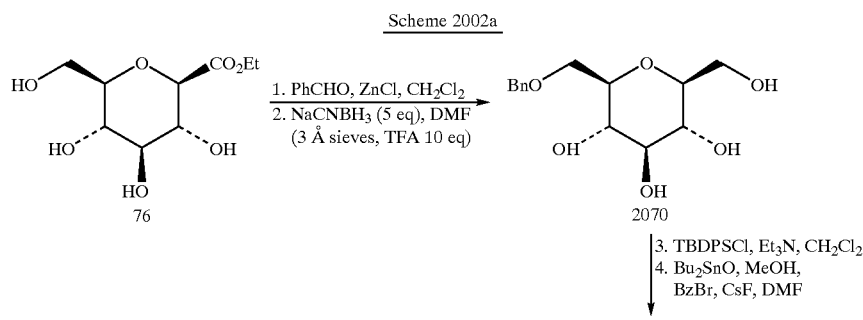

-continued

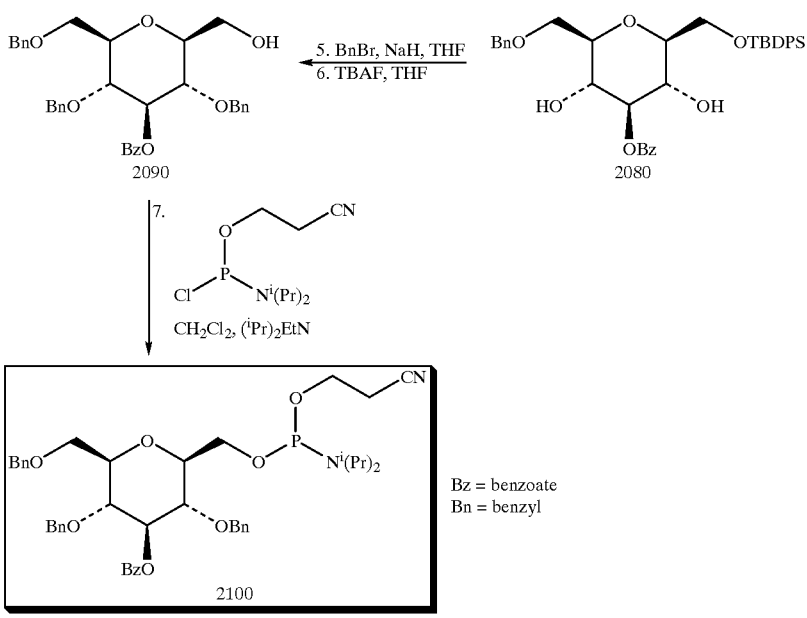

Bz = benzoate
Bn = benzyl

2. Connection of the C-3 differentiated sugar to a solid support

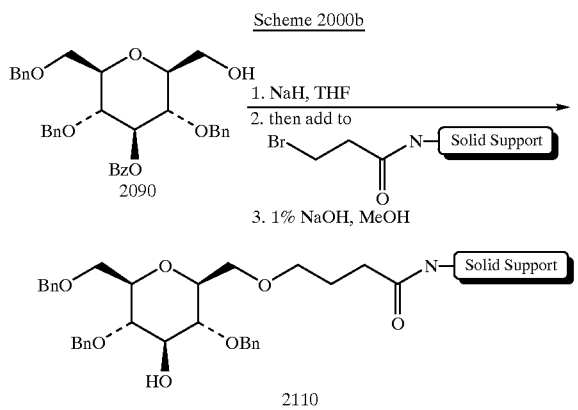

Preparation of Compound 2070

To a solution of 76 (1.0 equiv) was added methylene chloride (0.1 M) and benzaldehyde (1.1 equiv), and the solution was exposed to ZnCl (1.1 equiv) at 25° C. and allowed to stir for 2.5 hour. The solution is then diluted with ether and then washed with a saturated solution of sodium bicarbonate (2x), water (2x), brine (1x) and then dried over $MgSO_4$. The compound is purified by flash column chromatography to yield the desired benzylidene.

Procedure adopted from Johansson R.; Samuelsson; B. *J. Chem. Soc., Chem. Commun.*, 1984, 201. To a solution of the benzylidene acetal (1 equiv) and sodium cyanoborohydride (5 equiv.) in DMF (0.125 M) containing powedered 3 angtrsom molecular sieves is added trifluoroacetic acid (10 equiv) and the reaction is allowed to stir at 0° C. until no starting material remains. Reaction mixture is then diluted with ethyl acetate (2 L) and washed with a small amount of water (2x) and brine (2x). Aqueous layer is back extracted with ethyl acetate (3x) and then recombined with the organic layer which was then dried over $MgSO_4$ and evaporated. Purification by flash column chromatography yields the desired benzyl ether 2070.

Preparation of Compound 2080

To a solution of 2070 (1.0 equivalents) in methylene chloride (0.10 Molar), is added triethylamine (1.1 equivalents) at 0° C. Subsequent addition of tertbutyldiphenylsilylchloride (1.1 equivalents) is followed by stirring for 2 hours and then the reaction is diluted with diethylether and washed with ammonium chloride (2x), brine (1x) and then dried ($MgSO_4$) and concentrated. Purification by flash column chromatography affords the TBDPS ether which is subsequently carried on as follows:

The TBDPS ether is then azeotroped with benzene (2x100 mL) and then dried overnight under vacuum over $P_2O_5$. A mixture of benzylidene, dibutyl tin oxide (1.2 equiv.) and dry methanol (0.25 M) are heated at reflux for 4 h until the solution became clear and homogeneous. (An automatic stirring apparatus may be necessary.) The solvent is next removed in vacuo to give a foamy white tin complex which was then azeotroped with benzene (2x) and dried (2 h to overnight) under vacuum over $P_2O_5$. Next, anhydrous DMF (0.2 M) is added to redissolve the tin complex and then CsF (1.2 equiv.) and finally Benzoyl bromide for the benzoate formation, (1.5 equiv.) are added and then heated (40° C.) overnight. The clear solution is partially distilled under vacuum, (3.3 mm Hg, 75–100° C.) to obtain ⅕ the original volume of solvent. Reaction mixture was then diluted with ethyl acetate (2 L) and washed with a small amount of water (2x) to remove cesium salts. Aqueous layer is back extracted with ethyl acetate (3x) and then recombined with the organic layer which was then dried over $MgSO_4$ and evaporated. Purification by flash column chromatography yields the desired benzyl ether 2080. For related chemistry see Nagashima, N.; Ohno, M. *Chemistry Letters, Chem. Soc. of Japan* 1987, 141.

Preparation of Compound 2090

To a solution of alcohol 2080 (1.0 equiv.) in THF (0.5 M) at 0° C., is added NaH (1.0 equiv., 35% dispersion in mineral oil) over several portions. The reaction mixture is warmed to room temperature and stirred 1 h. Next, the reaction is cooled to 0° C. and treated with benzyl bromide (1.0 equiv.) and stirred for 1.5 h. The compound is then treated with tetrabutylammonium fluoride (2.0 equivalents) and allowed to stir for an additional 2 hours. A saturated solution of ammonium chloride (50 mL) is then added drop wise quench the reaction mixture at 0° C. and the mixture was diluted with ethyl acetate, washed with water (2×). brine (1×), dried over MgSO$_4$ and evaporated. Purification by flash column chromatography yields tribenzyl ether 2090.

Preparation of Compound 2100

To a solution of 2090 (1.0 equivalents) in methylene chloride (0.10 M), is added diisopropylethylamine (4.0 equivalents) at 25° C. The reaction is stirred for 5 minutes and then 2-cyanoethyl-N,N-diisopropyl-chlorophosphoramidite (1.5 equiv) is added, as prepared from the procedures of Sinha et al. *Nucl. Acids Res.* 1984, 12, 4539. After 15 minutes the reaction is complete and is next diluted with ether and next washed with brine (1×) and is then dried (MgSO$_4$) and concentrated. Purification by flash column chromatography (silica, 30% ethyl acetate in petroleum ether) affords compound 2100 (as shown in scheme 2002).

Synthesis of a C1-C3-Phosophodiester oligomer using a solid support

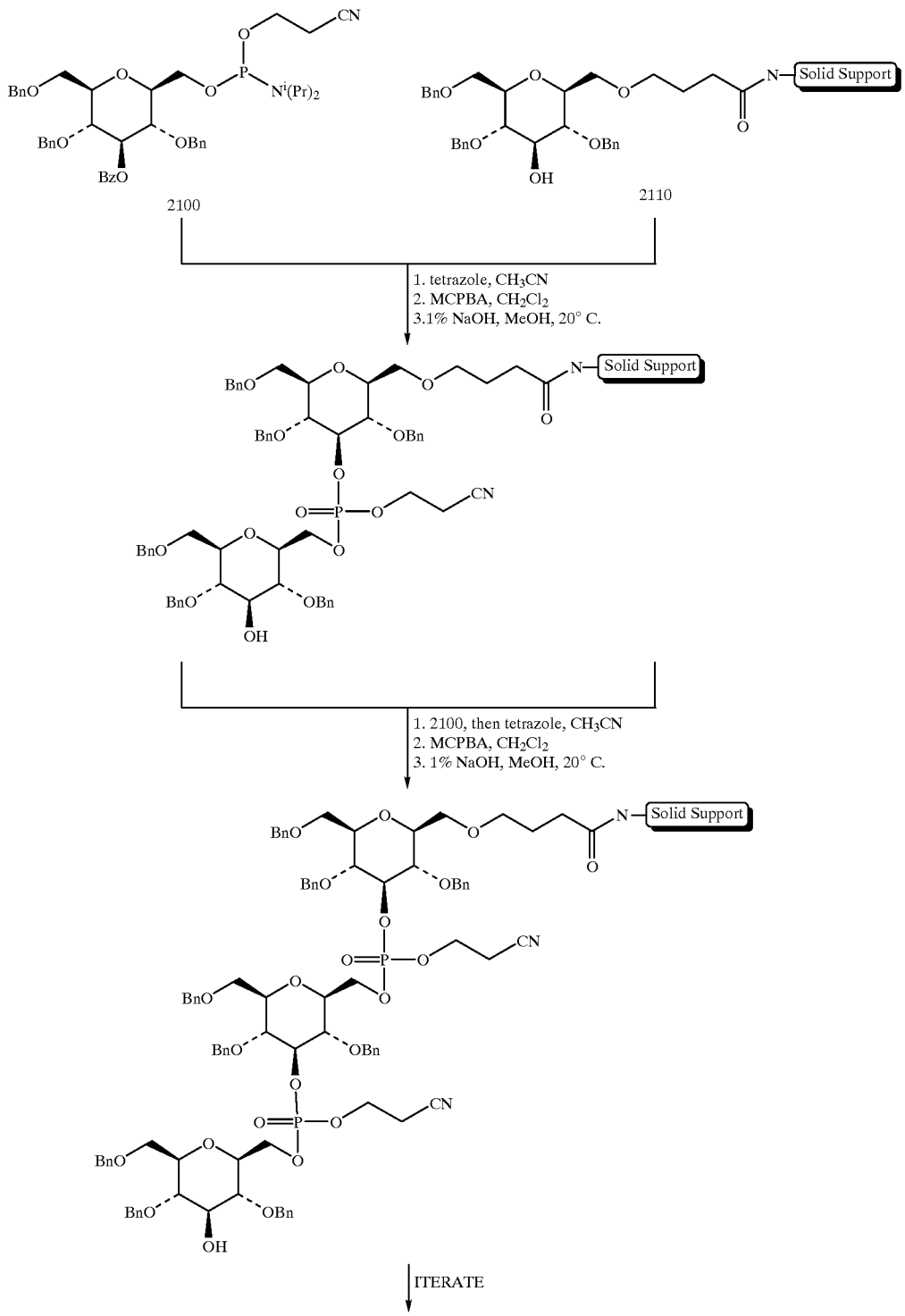

Preparation of Compound 2110

To a solution of alcohol 2090 (1.0 equiv.) in THF (0.5 M) at 0° C., is added NaH (1.0 equiv., 35% dispersion in mineral oil) over several portions. The reaction mixture is warmed to room temperature and stirred 1 h. Next, the reaction is cooled to 0° C. and exposed to the solid support functionalized with a bromide linker or any reasonable leaving group attached (1.0 equiv.) and stirred for 2 hours. A saturated solution of ammonium chloride (50 mL) is added dropwise to quench the reaction mixture at 0° C. and the support was washed with ethyl acetate, 1% NaOH in methanol (2×) to remove the benzoate and finally brine (1×) to give 2110. The solid support used is the standard N-(2-Aminoethyl)-3-amino-propyl glass support; amino-polystyrene resin; aminopropyl glass; isothiocyanato glass and others as purchased from Sigma company. All supports may be with or without a linker extending from the amino group on the support (eg. succinate linkage, amide, ether, alkyl chain with terminal carbon activated as free alcohol, bromide etc.).

Preparation of Compound 2120

To a solution of 76 (1.0 equiv) was added methylene chloride (0.1 M) and benzaldehyde (1.1 equiv), and the solution was exposed to ZnCl (1.1 equiv) at 25° C. and allowed to stir for 2.5 hour. The solution is then diluted with ether and then washed with a saturated solution of sodium bicarbonate (2×), water (2×), brine (1×) and then dried over $MgSO_4$. The compound is purified by flash column chromatography to yield the desired 1. Synthesis of a C-4 differentiated sugar

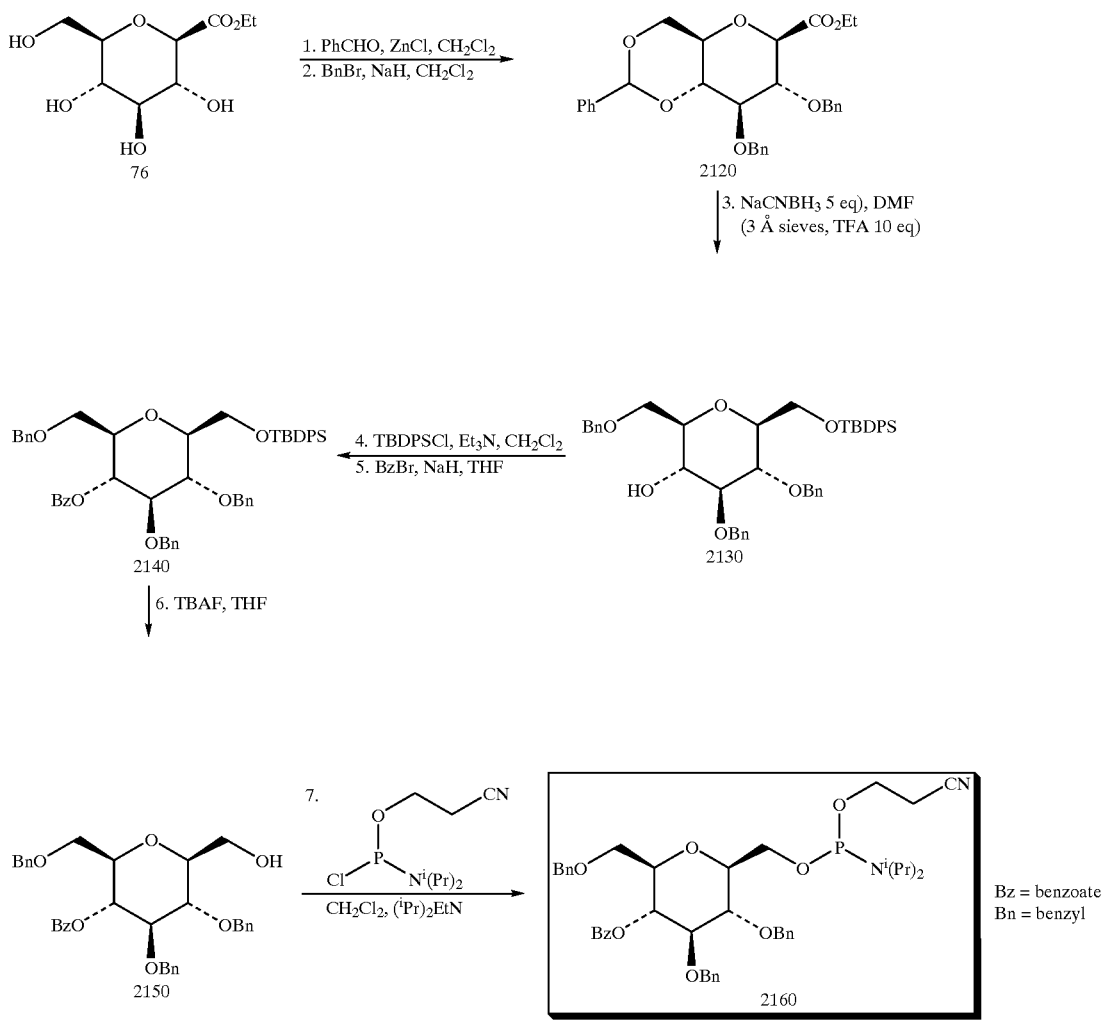

Scheme 2004a

Bz = benzoate
Bn = benzyl

2. Connection of the the C-4 differentiated sugar to a solid support

Scheme 2004b

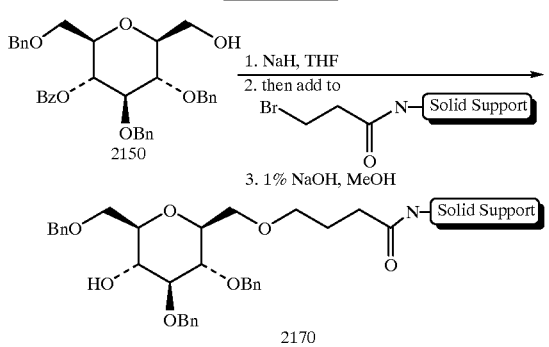

benzylidene and carried on as follows:

To a solution of benzylidene (1.0 equiv.) in THF (0.5 M) at 0° C., is added NaH (1.0 equiv., 35% dispersion in mineral oil) over several portions. The reaction mixture is warmed to room temperature and stirred 1 h. Next, the reaction is cooled to 0° C. and treated with benzyl bromide (1.0 equiv.) and stirred for 1.5 h. A saturated solution of ammonium chloride (50 mL) is then added dropwise to quench the reaction mixture at 0° C. and the mixture was diluted with ethyl acetate, washed with water (2x), brine (1x), dried over MgSO₄ and evaporated. Purification by flash column chromatography yields tribenzyl ether 2120.

Preparation of Compound 2130

Procedure adopted from Johansson R.; Samuelsson; B. *J. Chem. Soc., Chem. Commun.,* 1984, 201. To a solution of the benzylidene acetal 2120 (1 equiv) and sodium cyanoborohydride (5 equiv.) in DMF (0.125 M) containing powedered 3 angtrsom molecular sieves is added trifluoroacetic acid (10 equiv) and the reaction is allowed to stir at 0° C. until no starting material remains. Reaction mixture is then diluted with ethyl acetate (2 L) and washed with a small amount of water (2x) and brine (2x). Aqueous layer is back extracted with ethyl acetate (3x) and then recombined with the organic layer which was then dried over MgSO₄ and evaporated. Purification by flash column chromatography yields the desired benzyl ether 2130.

Preparation of Compound 2140

To a solution of 2130 (1.0 equivalents) in methylene chloride (0.10 Molar), is added triethylamine (1.1 equivalents) at 0° C. Subsequent addition of tertbutyldiphenylsilylchloride (1.1 equivalents) is followed by stirring for 2 hours and then the reaction is diluted with diethylether and washed with ammonium chloride (2x), brine (1x) and then dried (MgSO₄) and concentrated. Purification by flash column chromatography affords the TBDPS ether which is subsequently carried on as follows:

To a solution of TBDPS ether (1.0 equiv.) in THF (0.5 M) at 0° C., is added NaH (1.0 equiv., 35% dispersion in mineral oil) over several portions. The reaction mixture is warmed to room temperature and stirred 1 h. Next, the reaction is cooled to 0° C. and treated with benzoyl bromide to afford benzoate formation (1.0 equiv.) and stirred for 1.5 h. A saturated solution of ammonium chloride (50 mL) is then added dropwise to quench the reaction mixture at 0° C. and the mixture was diluted with ethyl acetate, washed with water (2x), brine (1x), dried over MgSO₄ and evaporated. Purification by flash column chromatography yields tribenzyl ether 2140.

Preparation of compound 2150

The compound 2140 is then treated with tetrabutylammonium fluoride (2.0 equivalents) in THF (0.1 Molar) and allowed to stir for an additional 2 hours at 25° C. A saturated solution of ammonium chloride (50 mL) is then added dropwise to quench the reaction mixture at 0° C. and the mixture was diluted with ethyl acetate, washed with water (2x), brine (1x), dried over MgSO₄ and evaporated. Purification by flash column chromatography yields tribenzyl ether 2150.

Preparation of Compound 2160

To a solution of 2150 (1.0 equivalents) in methylene chloride (0.10 M), is added diisopropylethylamine (4.0 equivalents) at 25° C. The reaction is stirred for 5 minutes and then 2-cyanoethyl-N,N-diisopropylchlorophosphoramidite (1.5 equiv) is added, as prepared from the procedures of Sinha et al. *Nucl. Acids Res.* 1984, 12, 4539. After 15 minutes the reaction is complete and is next diluted with ether and next washed with brine (1x) and is then dried (MgSO₄) and concentrated. Purification by flash column chromatography (silica, 30% ethyl acetate in petroleum ether) affords compound 2160 (as shown in scheme 2004).

Preparation of Compound 2170

To a solution of alcohol 2150 (1.0 equiv.) in THF (0.5 M) at 0° C., is added NaH (1.0 equiv., 35% dispersion in mineral oil) over several portions. The reaction mixture is warmed to room temperature and stirred 1 h. Next, the reaction is cooled to 0° C. and exposed to the solid support functionalized with a bromide linker or any reasonable leaving group attached (1.0 equiv.)

Synthesis of a C1-C4-Phosophodiester oligomer using a solid support

Scheme 2005

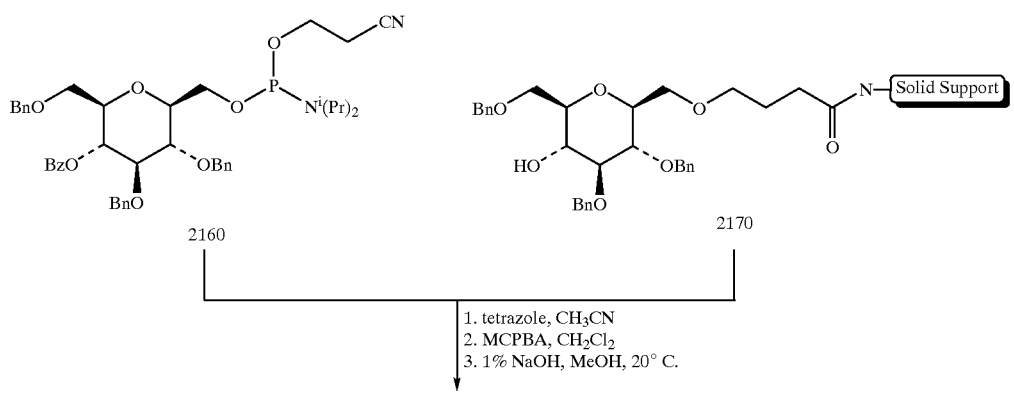

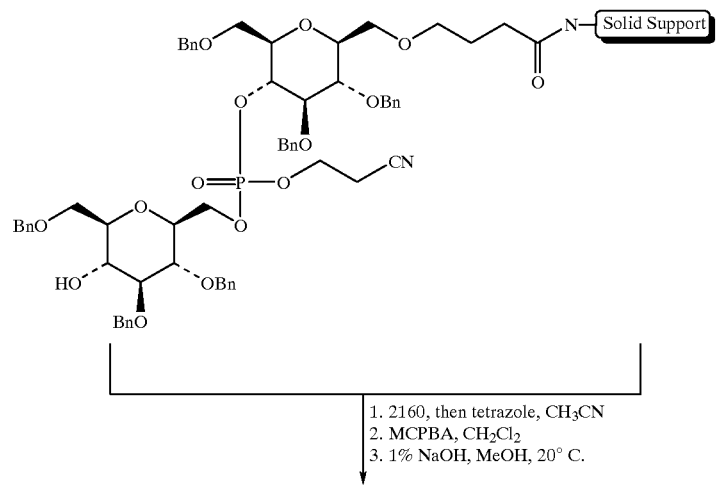

1. 2160, then tetrazole, $CH_3CN$
2. MCPBA, $CH_2Cl_2$
3. 1% NaOH, MeOH, 20° C.

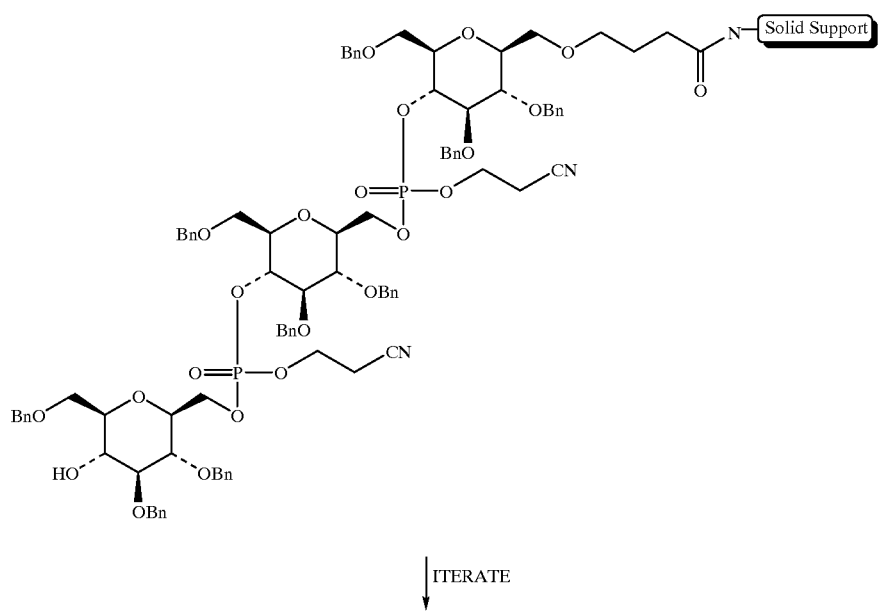

ITERATE and stirred for 2 hours. A saturated solution of ammonium chloride (50 mL) is added dropwise to quench the reaction mixture at 0° C. and the support was washed with ethyl acetate, 1% NaOH in methanol (2x) to remove the benzoate and finally brine (1x) to give 2170. The solid support used is the standard N-(2-Aminoethyl)-3-amino-propyl glass support; amino-polystyrene resin; aminopropyl glass; isothiocyanato glass and others as purchased from Sigma company. All supports may be with or without a linker extending from the amino group on the support (eg. succinate linkage, amide, ether, alkyl chain with terminal carbon activated as free alcohol, bromide etc.).

Preparation of Compound 3010

Procedure as described in Methods in Carbohydrate chemistry, Whistler, R., II, 1963 p. 327. A mixture of 80 g anhydrous D-glucosamine hydrochloride or D-galactosamine hydrochloride from Aldrich chemical company, in 200 mL. methanol and 20 g Dowex 50 (H+) acidic resin, is stirred at the boiling point in a round bottom flask. After 24-hr. reaction time, the resin is removed by filtration and ished three times with 20 ml. of methanol. The filrate and washings are combined and concentrated to about 125 ml by rotovap. The concentrate is allowed to cool to room temperature and the product crystallizes overnight and carried on as follows:

The methyl glycoside is dissolved in chloroform (0.5 M) and to it, is added phthalic anhydride (1.5 equiv.) and the reaction mixture is allowed to reflux at 70° C. for 4 h. The product Scheme 3000

1. C-2 differentiated amine derivative

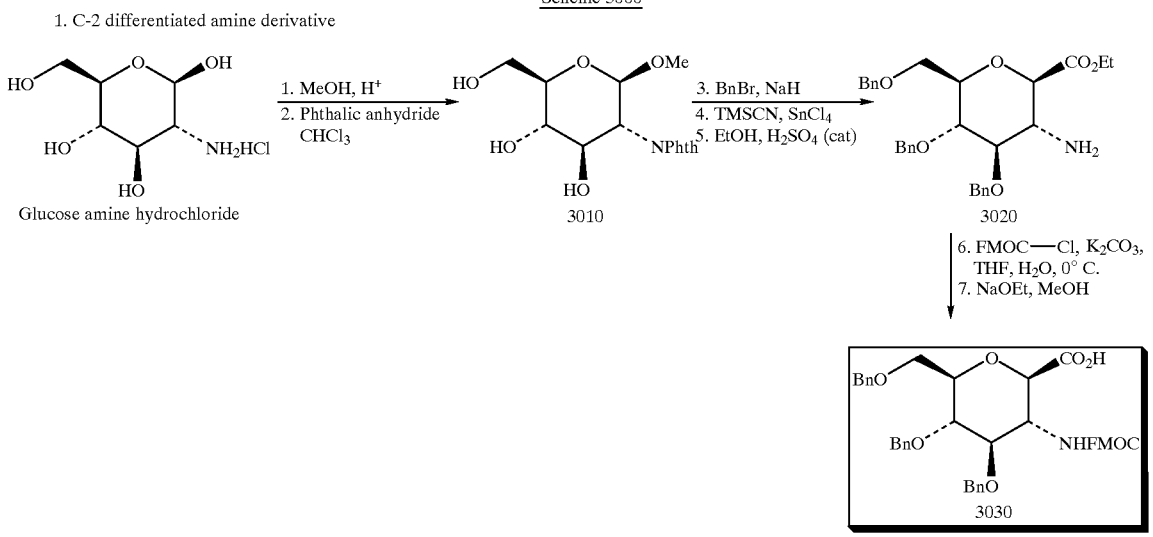

2. Connection of a C-2 differentiate amine sugar to a solid support

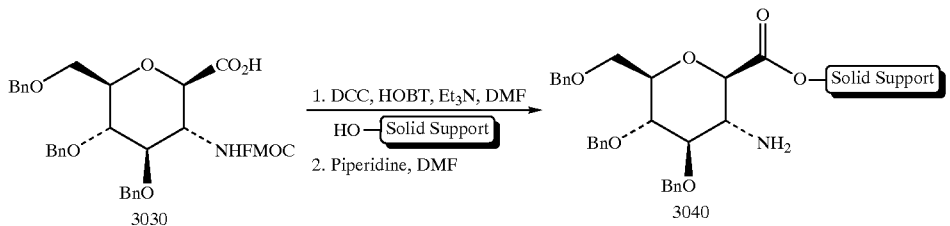

3010 is then crystallized and carried onto the next step.

Preparation of Compound 3020

To a solution of alcohol 3010 (1.0 equiv.) in THF (0.5 M) at 0° C., is added NaH (3.3 equiv., 35% dispersion in mineral oil) over several portions. The reaction mixture is warmed to room temperature and stirred 1 h. Next, the reaction is cooled to 0° C. and treated with benzyl bromide (3.3 equiv.) and stirred for 1.5 h. A saturated solution of ammonium chloride (50 mL) is then added dropwise to quench the reaction mixture at 0° C. and the mixture was diluted with ethyl acetate, washed with water (2×), brine (1×), dried over $MgSO_4$ and evaporated. Purification by flash column chromatography yields tribenzyl ether and is carried on as follows:

To a solution of tribenzyl ether in nitromethane is added trimethylsilyl cyanide (3.0 equivalents) and then $SnCl_4$ (0.02 equivalents). The mixture is stirred for one hour and then an aqueous solution of sodium acetate was added to hydrolyze the remaining trimethylsilyl cyanide. The mixture is evaporated and the remaining oil is resuspended in dichloromethane and washed with sodium acetate solution (1×), water (1×), brine (1×) and then dried over magnesium sulphate and concentrated. The crude solid is then recrystallized from methanol is next dissolved in ethanol (0.15 M) and then concentrated $H_2SO_4$ (0.01 equivalents-catalytic) is added. The reaction mixture is heated to 85° C. for eight hours. The solution is next concentrated in vacuo and purification by flash column chromatography affords compound 3020 scheme 3000.

Preparation of Compound 3030

To a solution of 3020 (1.0 equivalents) in methylene chloride (0.10 Molar), is added potassium carbonate (2.0 equivalents) at 0° C. Subsequent addition of 9-fluorenylmethyl chloroformate (FMOC-Cl, 1.2 equivalents) is followed by stirring for 2 hours and then the reaction is diluted with diethylether and washed with ammonium chloride (2×), brine (1×) and then dried ($MgSO_4$) and concentrated. Purification by flash column chromatography affords product which is carried on as follows:

To a solution of ester in ethanol (13 Molar), is added sodium ethoxide (0.3 equivalents) and the reaction mixture is stirred for two hours at room temperature. The solution is then concentrated in vacuo and purification by flash column chromatography affords compound 3030 scheme 3000.

Preparation of Compound 3040

To a stirred solution of the acid 3030 (1.0 equivalents) and the (1.1 equivalents) in dimethylformamide (0.10 Molar) at 25° C., is added 1-hydroxybenzotriazole (HOBT; 1.1 equivalents). Next dicyclohexylcarbodiimide (1.2 equivalents) is added and the reaction is stirred for 2 hours. The mixture is then exposed to the solid support and mixed for 24 hours. (The solid support used is the standard N-(2-Aminoethyl)-3-amino-propyl glass support; aminopolystyrene resin; aminopropyl glass; isothiocyanato glass and others as purchased from Sigma company. All supports may be with or without a linker extending from the amino group on the support (eg. succinate linkage, amide, ether, alkyl chain with terminal carbon activated as free alcohol, bromide etc.)). The mixture is then diluted with ether, washed with aqueous $NaHCO_3$ (2×), water (2×), and brine (2×). Next, the compound/support (1.0 equivalents) in dimethyl-formamide (0.10 Molar) at 25° C., is added piperidine (1.1 equivalents). The support is stirred or exposed for 1 hour and is then diluted with ether, and washed with aqueous $CuSO_4$ (2×), water (2×), and brine (2×). The final step affords compound 3040.

Scheme 3001
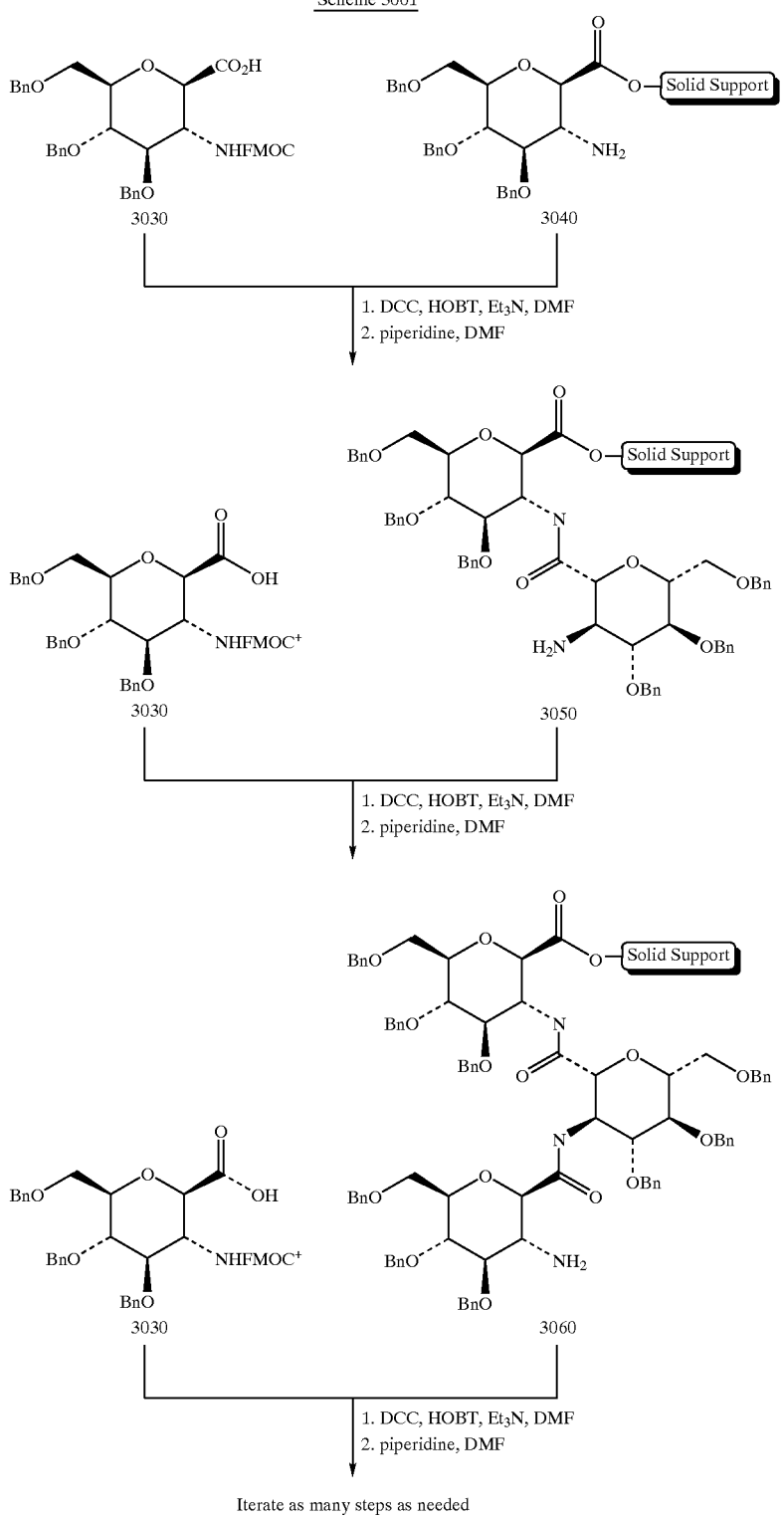
Physical Data For Scheme 9
Phosphoramidate 138 (2 diastereomers): IR, (neat) cm$^{-1}$: 3089, 2964, 2927, 2856, 2253, 1497, 1455, 1396, 1363, 1253, 1184, 1156, 1094, 1028, 978, 876, 836, 779, 735; $^1$H-NMR (400 MHz, $C_6D_6$): δ7.34 (m, 5H, Ph), 7.14 (m, 10H, Ph), 4.97 (m, 4H, $CH_2$Ph), 4.78 (m, 2H, $CH_2$Ph), 4.07–3.24 (m, 13H, OCH, $OCH_2$, $CH_2$CN), 1.81 (m, 2H, $CH(CH_3)_2$), 1.16 (m, 12H, $CH_3$CH), 1.03, 1.02 (2 s, 9H, $^t$BuSi), 0.20, 0.18, 0.16, 0.15, (4 s, 6H, $Me_2$Si) HRMS: $C_{43}H_{63}O_7N_2PSi$, Calc. (M+Cs$^+$): 911.3197; found: 911.3185.

Naphthoylester [136] IR, (neat) cm$^{-1}$: 3494, 3062, 2919, 1716, 1630, 1600, 1454, 1355, 1284, 1228, 1197, 1091, 779, 736; $^1$H-NMR (250 Mz, CDCl$_3$): δ8.58 (s, 1H, Ar), 8.00 (m, 2H, Ar), 7.89 (m, 2H, Ar), 7.59 (m, 2 H, Ar), 7.32 (m, 15H, Ph), 4.95 (m, 3H), 4.90 (d, J=4.5 Hz, 1H), 4.69 (m, 3H), 4.52 (dd, J=3.9, 12.0 Hz, 1H), 3.91 (d, J=2.6, 12.0, 1H), 3.83 (d, J=8.3, 1H), 3.70 (m, 4H), 3.96 (m, 1H), 2.25 (s, 1H, OH). HRMS: $C_{39}H_{38}O_7$ Calc. (M+Cs$^+$): 751.1672; found: 751.1668.

Dimer [142] IR, (neat) cm$^{-1}$: 3397, 3030, 2923, 2254, 1718, 1653, 1629, 1497, 1453, 1355, 1284, 1227, 1197, 1094, 1029, 780. $^1$H-NMR (400 MHz, C$_6$D$_6$): δ8.82 (s, 1H, Ar), 8.26 (d, 1H, Ar), 7.72 (m, 1H, Ar), 7.61 (m, 1 H, Ar), 7.48 (m, 1H, Ar), 7.37–6.95 (m, 32H, Ar, Ph), 4.89–4.18 (m, 21H, CH$_2$Ph, CH$_2$—Ar, —CH$_2$CH$_2$CN, CHCH$_2$—Ar and CH$_2$OH), 3.95–3.45 (m, 13H, CH— and CH$_2$-sugar), 1.71 (s, 1H, OH); HRMS: $C_{170}H_{72}O_5NP$ calc. (M+H$^+$): 1198.4718; found: 1198.4715.

Tetramer [150] IR, (neat) cm$^{-1}$: 3420, 3064, 2924, 2255, 1721, 1497, 1455, 1357, 1278, 1028, 737. $^1$H-NMR (400 MHz, CDCl$_3$): δ8.41 (s, 1H, Ar), 8.00 (m, 2H, Ar), 7.91 (m, 2H, Ar), 7.55 (m, 2H, Ar), 7.30 (m, 60H, Ph), 4.93–4.05 (m, 39H, CH$_2$Ph, CH$_2$—Ar, CH$_2$CH$_2$CN and CH$_2$OH), 3.88–3.27 (m, 23H, CH— and CH$_2$-sugar), 2.58 (s, 1H, OH). HRMS: $C_{132}H_{140}O_{31}N_3P_3$ Calc. (M+Cs$^+$): 2488.7738; found: 2488.7758

Tetramer [154] IR, (neat) cm$^{-1}$: 3376, 2934, 1450, 1244, 1110, 1088. $^1$H-NMR (400 MHz, D$_2$O): δ8.41 (s, 1H, Ar), 8.00 (m, 2H, Ar), 7.91 (m, 2H, Ar), 7.55 (m, 2 H, Ar), 4.93–4.05 (m, 4H, CH$_2$—Ar and CH$_2$OH), 3.88–3.27 (m, 32H, CH— and CH$_2$-sugar); HRMS: $C_{39}H_{59}O_{31}P_3$ Calc. (M+H$^+$): 1117.2331; found: 1117.2350.

What is claimed is:

1. A library of oligomeric carbopeptoid compounds employable for drug screening, each oligomeric carbopeptoid compound including at least two carbohydrate amino acid subunits (CA's) coupled to one another via an amide linkage having a carbonyl carbon and an amido nitrogen, said amide linkage being represented by the following formula:

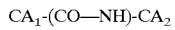

$CA_1$-(CO—NH)-$CA_2$ wherein:

$CA_1$ is a first carbohydrate amino acid subunit having an anomeric carbon bonded to the carbonyl carbon of said amide linkage for forming a C-glycosidic linkage therewith; and $CA_2$ is a second carbohydrate amino acid subunit having a non-anomeric carbon bonded to the amido nitrogen of said amide linkage.

2. A library of oligomeric carbonucleotoid molecules employable for drug screening, each oligomeric carbonucleotoid molecule including at least two carbohydrate C-glycoside subunits (CG's) coupled to one another by means of a phosphodiester linkage, said phosphodiester linkage being represented by a formula as follows:

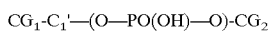

$CG_1$-$C_1$'—(O—PO(OH)—O)-$CG_2$ wherein:

(O—PO(OH)—O) is said phosphodiester linkage;

$CG_1$-$C_1$' is a first carbohydrate C-glycoside subunit having an anomeric carbon forming a C-glycosidic bond with a carbon $C_1$', said carbon $C_1$' being bonded to said phosphodiester linkage; and $CG_2$ is a second carbohydrate C-glycoside subunit having a non-anomeric carbon bonded to said phosphodiester linkage.

3. A derived carbohydrate C-glycoside having an anomeric carbon and non-anomeric carbons, said anomeric carbon forming a C-glycosidic bond with a carbon $C_1$', said carbon $C_1$' being bonded to an activated phosphite, each of said non-anomeric carbons being substituted with a radical selected from the group consisting of blocked hydroxyl, differentially protected hydroxyl, and hydrogen, with the proviso that at least one radical is a differentially protected hydroxyl.

4. A derived carbohydrate C-glycoside having an anomeric carbon and non-anomeric carbons, said anomeric carbon forming a C-glycosidic bond with a carbon $C_1$', said carbon $C_1$' being bonded to an activated phosphite, each of said non-anomeric carbons being substituted with a radical selected from the group consisting of blocked hydroxyl, unprotected hydroxyl, and hydrogen, with the proviso that at least one radical is an unprotected hydroxyl and at least one radical is a blocked hydroxyl.

* * * * *